US008829179B2

(12) United States Patent
Santel et al.

(10) Patent No.: US 8,829,179 B2
(45) Date of Patent: Sep. 9, 2014

(54) MEANS FOR INHIBITING THE EXPRESSION OF ANG2

(75) Inventors: Ansgar Santel, Berlin (DE); Jörg Kaufmann, Berlin (DE); Martin Witzenrath, Berlin (DE)

(73) Assignee: Silence Therapeutics GmbH, Berlin (DE)

( * ) Notice: Subject to any disclaimer, the term of this patent is extended or adjusted under 35 U.S.C. 154(b) by 13 days.

(21) Appl. No.: 13/201,917

(22) PCT Filed: Feb. 18, 2010

(86) PCT No.: PCT/EP2010/001036
§ 371 (c)(1), (2), (4) Date: Oct. 6, 2011

(87) PCT Pub. No.: WO2010/094491
PCT Pub. Date: Aug. 26, 2010

(65) Prior Publication Data

US 2012/0022138 A1 Jan. 26, 2012

(30) Foreign Application Priority Data

Feb. 18, 2009 (EP) .................................... 09002290
Jan. 22, 2010 (EP) .................................... 10000626

(51) Int. Cl.
*C07H 21/04* (2006.01)
*C07H 21/02* (2006.01)
*C12N 15/63* (2006.01)
*A61K 48/00* (2006.01)

(52) U.S. Cl.
USPC ......... 536/24.5; 536/23.1; 435/320.1; 514/44

(58) Field of Classification Search
CPC ........... A61K 2300/00; A61K 31/7105; C12N 2310/14; C12N 15/113
See application file for complete search history.

(56) References Cited

U.S. PATENT DOCUMENTS 7,452,987 B2 11/2008 Giese et al.
7,893,245 B2 2/2011 Giese et al.
8,017,804 B2 9/2011 Keil et al.
8,324,370 B2 12/2012 Giese et al.
8,357,722 B2 1/2013 Keil et al.
2004/0180351 A1 9/2004 Giese et al.
2008/0274116 A1 11/2008 Keil et al.
2009/0074852 A1 3/2009 Kaufmann et al.
2009/0186845 A1 7/2009 Giese et al.
2010/0062967 A1 3/2010 Keil et al.
2011/0118456 A1 5/2011 Giese et al.
2011/0294871 A1 12/2011 Keil et al.
2012/0065138 A1 3/2012 Keil et al.
2013/0102769 A1 4/2013 Giese et al.
2013/0165381 A1 6/2013 Keil et al.

FOREIGN PATENT DOCUMENTS

EP 02017601 8/2002
EP 03008383 4/2003
WO WO 2004/094606 11/2004
WO WO 2005/105152 11/2005
WO WO 2006/069782 7/2006
WO WO 2007/121947 11/2007
WO WO 2008/109488 9/2008
WO WO 2009/008990 1/2009
WO WO 2009/008990 A2 * 1/2009 .................. 536/24.5

OTHER PUBLICATIONS

Devroe et al. (BMC Biotechnology 2002, 2:15, pp. 1-5).*
Bhandari, V. et al. "Hyperoxia causes angiopietin 2-medicated acute lung injury and necrotic cell death" *Nature Medicine*, Nov. 2006, pp. 1286-1293, vol. 12, No. 11, XP-002580319.
Czauderna, F. et al. "Structural variations and stabilising modifications of synthetic siRNAs in mammalian cells" *Nucleic Acids Research*, 2003, pp. 2705-2716, vol. 31, No. 11, XP-002579231.
Santel, A. et al. "RNA interference in the mouse vascular endothelium by systemic administration of siRNA-lipoplexes for cancer therapy" *Gene Therapy*, 2006, pp. 1360-1370, vol. 13, XP-002443322.
Written Opinion in International Application No. PCT/EP2010/001036, Jul. 16, 2010, pp. 1-7.

* cited by examiner

*Primary Examiner* — Amy Bowman
(74) *Attorney, Agent, or Firm* — Saliwanchik, Lloyd & Eisenschenk

(57) ABSTRACT

The present invention is related to an siRNA comprising an antisense strand and a sense strand, wherein all or a portion of said antisense strand comprises an antisense duplex region, wherein all or a portion of said sense strand comprises a sense duplex region, wherein said antisense duplex region is at least partially complementary to said sense duplex region, wherein said siRNA comprises a duplex region consisting of said antisense duplex region and said sense duplex region, and wherein: a) said antisense strand comprises a nucleotide sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 68, 74, 76, 78, 80, 82, 84, 86, 88, 90, 92, 94, 96, 98, 100, 102 or 104; or b) said antisense strand comprises an antisense duplex region, all or a portion of which, is complementary to a portion of SEQ ID NO: 1 or 70.

24 Claims, 20 Drawing Sheets

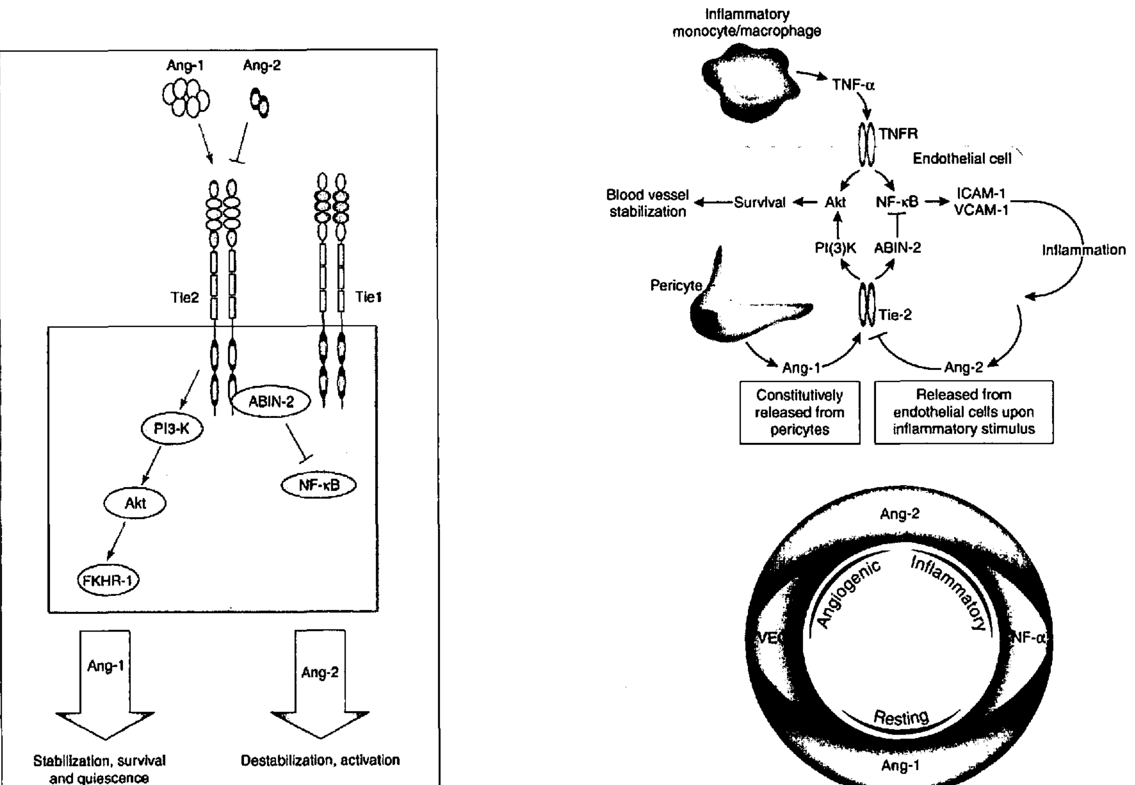
Fig. 1: Balance of powers showing grade influence of signals *Nature Medicine* 12, 171 - 172 (2006)
doi:10.1038/nm0206-171
Angiogenesis and inflammation face off
Beat A Imhof & Michel Aurrand-Lions
Ang2 promotes inflammation
Ang2 sensitizes endothelial cells to inflammatory stimuli
Ang2 upregulates the suboptimal resposne of endothelial cells to TNFa

Fig. 2: Ang2-19mer AtuRNAi

| siRNA Molecule # | SEQ ID NO: | Strand Designation | RNA-Sequence (5'->3') |
|---|---|---|---|
| 1 | 2 | A | uuaacuuccgcguuugcuc |
| | 3 | B | gagcaaacgcggaaguuaa |
| 2 | 4 | A | uacuugggcuuccacauca |
| | 5 | B | ugauguggaagcccaagua |
| 3 | 6 | A | uuguuuauuucacuggucu |
| | 7 | B | agaccagugaaauaaacaa |
| 4 | 8 | A | uccaugucacaguaggccu |
| | 9 | B | aggccuacugugacaugga |
| 5 | 10 | A | ucauacaaugaguaagccu |
| | 11 | B | aggcuuacucauuguauga |
| 6 | 12 | A | auccuuugugcuaaaauca |
| | 13 | B | ugauuuuagcacaaaggau |
| 7 | 14 | A | aguuggaaggaccacaugc |
| | 15 | B | gcaugugguccuuccaacu |
| 8 | 16 | A | aucaucaugguuguggccu |
| | 17 | B | aggccacaaccaugaugau |
| 9 | 18 | A | uagaaauagaauguuggag |
| | 19 | B | cuccaacauucuauuucua |
| 10 | 22 | A | aucuuaagcacguagcggu |
| | 23 | B | accgcuacgugcuuaagau |

Fig. 3: Screening for potent Ang2-siRNA molecules (AtuRNAi-19mers identified in Figure 2) in murine B16V and MS1 cells
(B16V/ MS1: 50.000 c/ 6well; siRNA: 40 nM, Lipid: atufect01, 1 μg/ ml; Lipoplex rinsed 4h post transfection; Lysis 48h post transfection)
mRNA levels determined by TaqMan realtime PCR
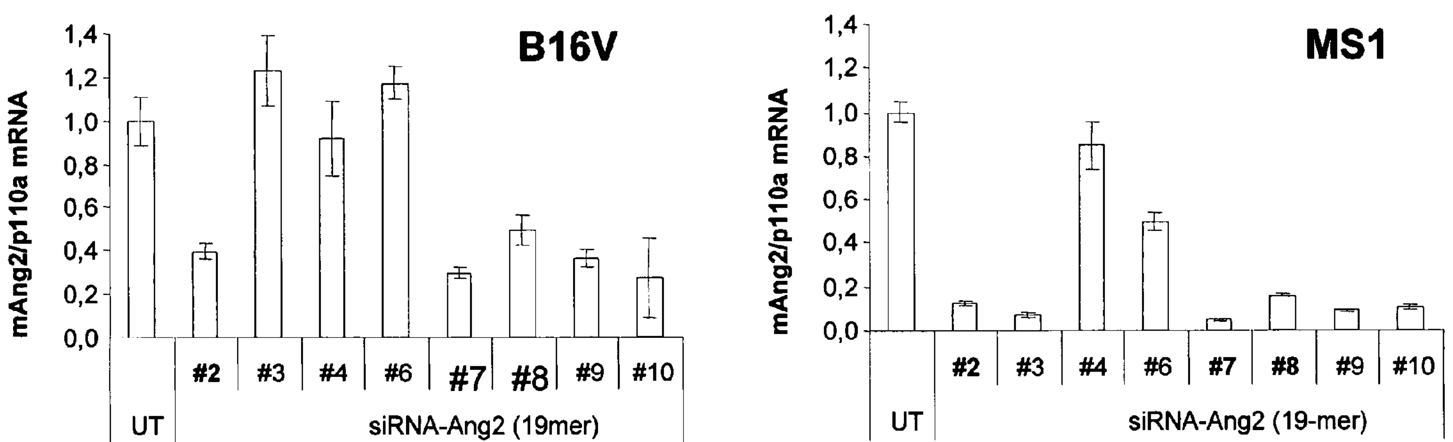
Ang2-siRNAs molecules #2-4, #6-8: hm; Ang2-siRNAs #9-10: m
siRNA #2: also matches Cynomolgus Ang2-predicted cDNA

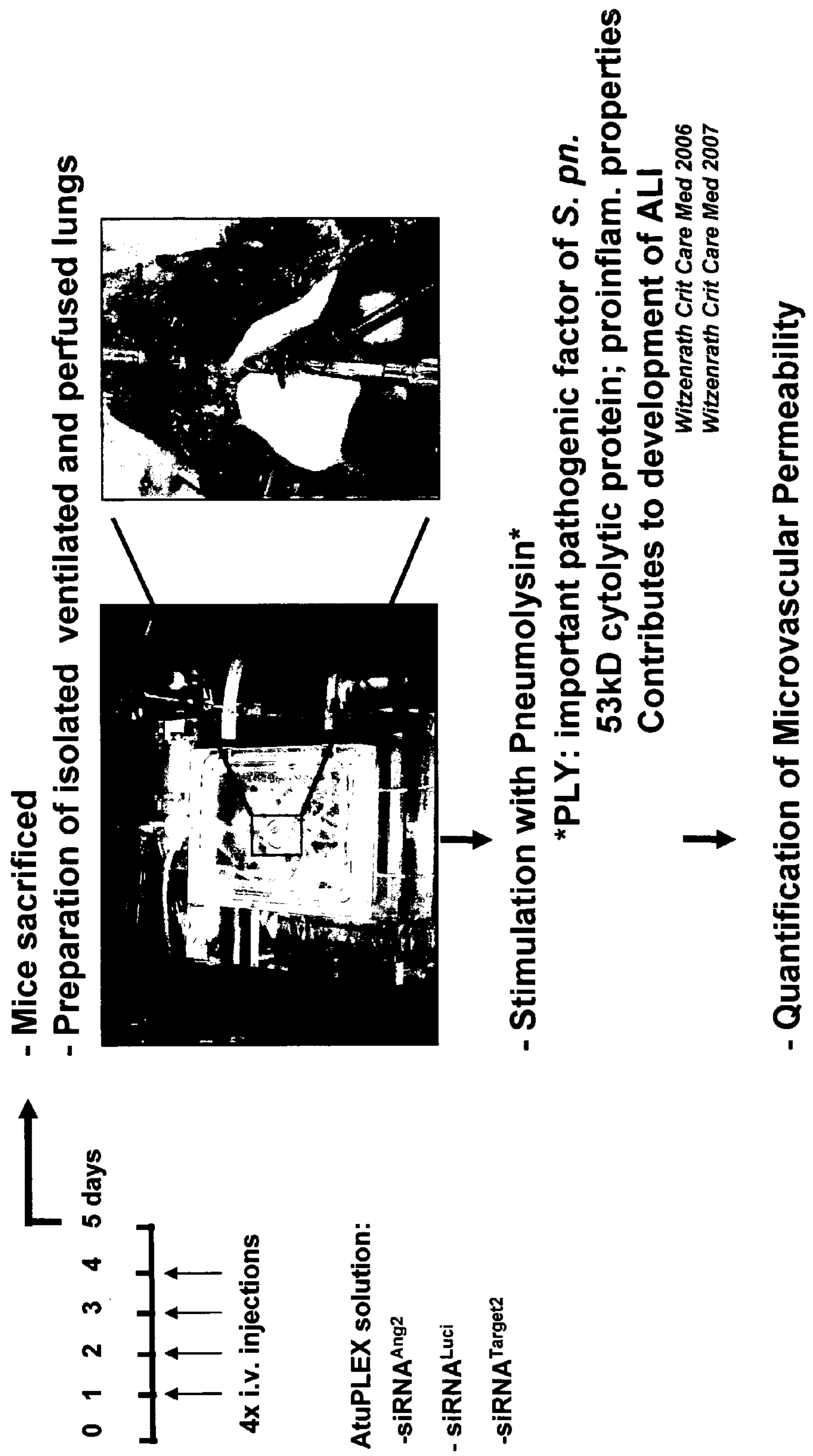
Fig. 4: Ang-2 knockdown attenuates PLY-induced permeability ex vivo
0 1 2 3 4 5 days
4x i.v. injections
AtuPLEX solution:
-siRNA^Ang2
-siRNA^Luci
-siRNA^Target2
- Mice sacrificed
- Preparation of isolated ventilated and perfused lungs
- Stimulation with Pneumolysin*
*PLY: important pathogenic factor of S. pn.
53kD cytolytic protein; proinflam. properties
Contributes to development of ALI
Witzenrath Crit Care Med 2006
Witzenrath Crit Care Med 2007
- Quantification of Microvascular Permeability

Fig. 5: Reduced vascular permeability in Pneumonia
siRNA Molecule #7 (19mer from Figure 2)
Lung vascular permeability
Protection assay (PLY-induced)
Lung permeability
Protection assay (Pneumonia infected)
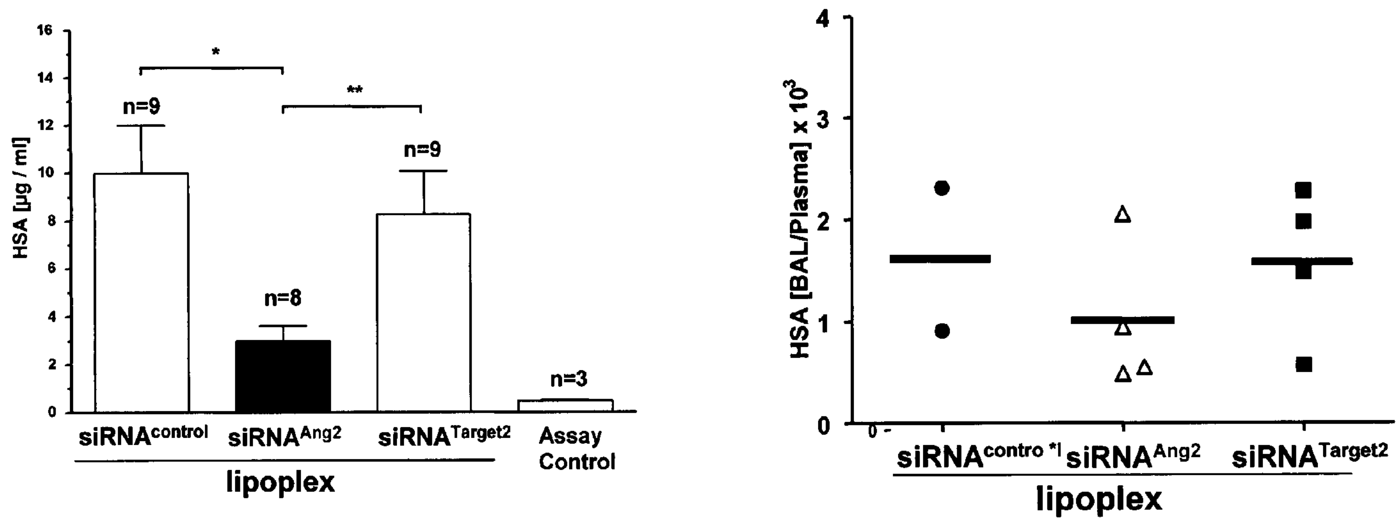
EX VIVO
IN VIVO

**Fig. 6: In vivo permeability assay with *S. pn.* Infected lungs 19-mers**
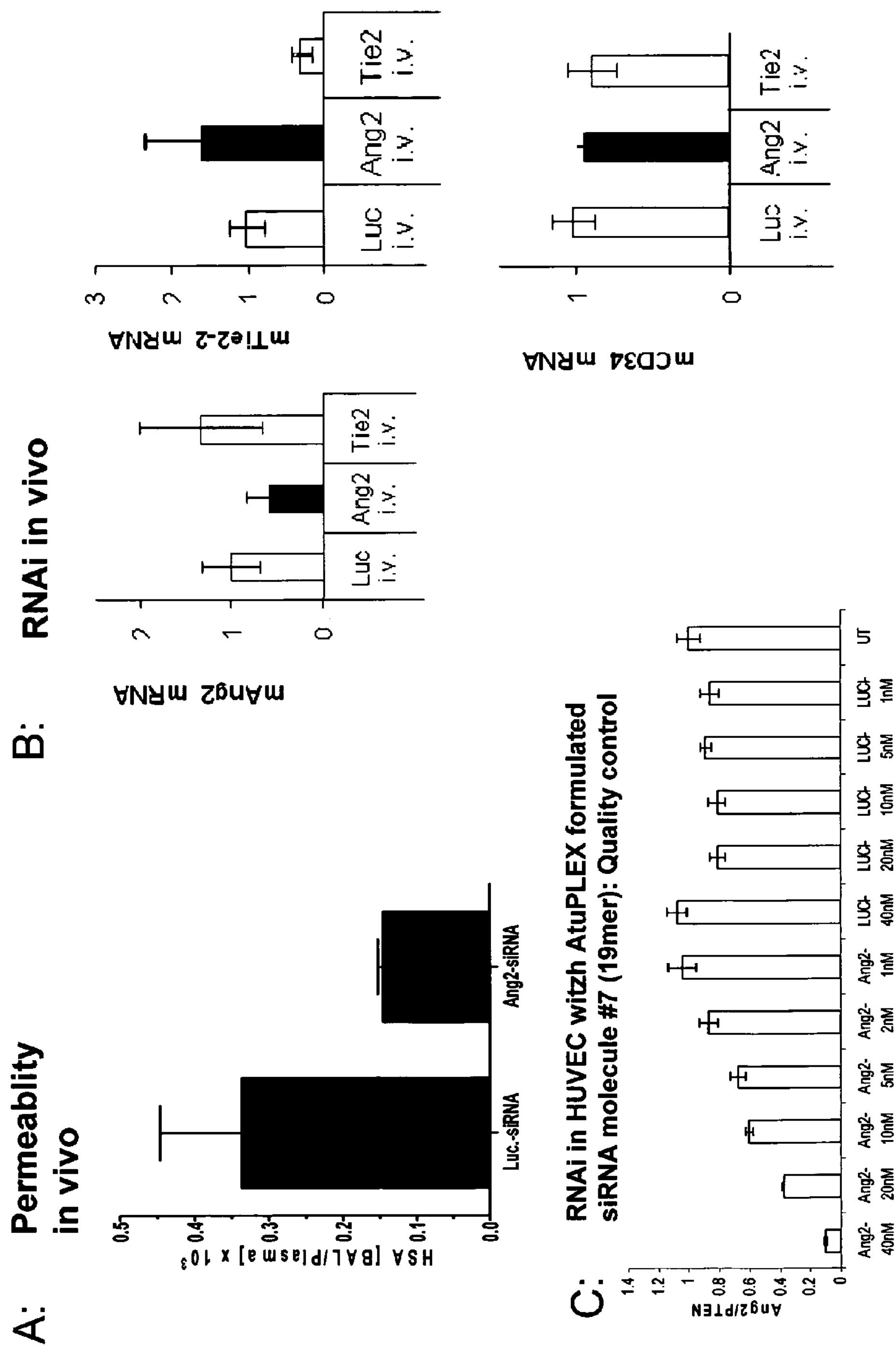

Fig. 7: Extension of siRNA-Ang2 – 19mer to 23-mer in B16V
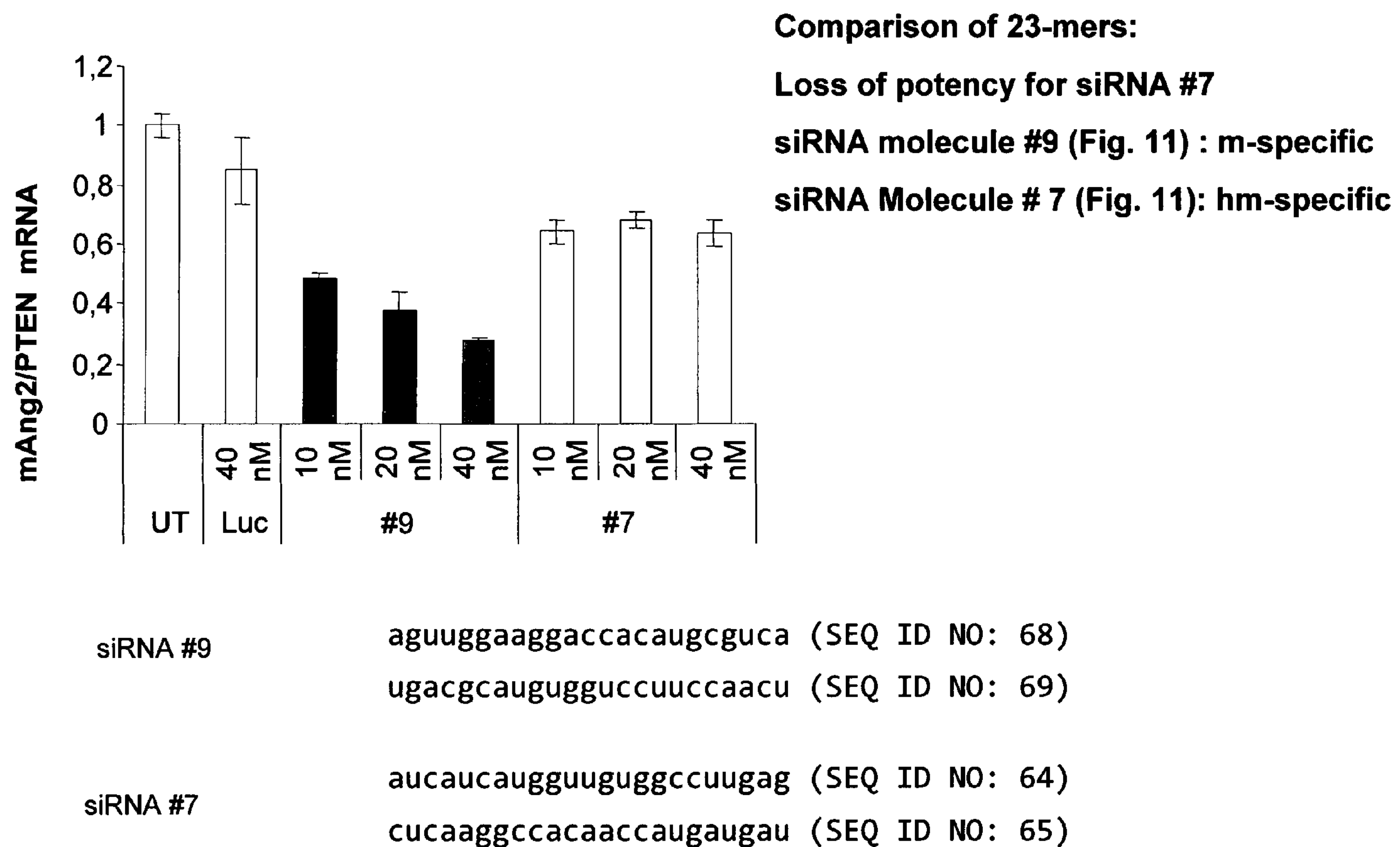
Comparison of 23-mers:
Loss of potency for siRNA #7
siRNA molecule #9 (Fig. 11) : m-specific
siRNA Molecule # 7 (Fig. 11): hm-specific
siRNA #9
aguuggaaggaccacaugcguca (SEQ ID NO: 68)
ugacgcaugugguccuuccaacu (SEQ ID NO: 69)
siRNA #7
aucaucaugguuguggccuugag (SEQ ID NO: 64)
cucaaggccacaaccaugaugau (SEQ ID NO: 65)

Fig. 8: Reduced vascular permeability in ex vivo Pneumonia model
Lung vascular permeability Protection assay (PLY-induced)
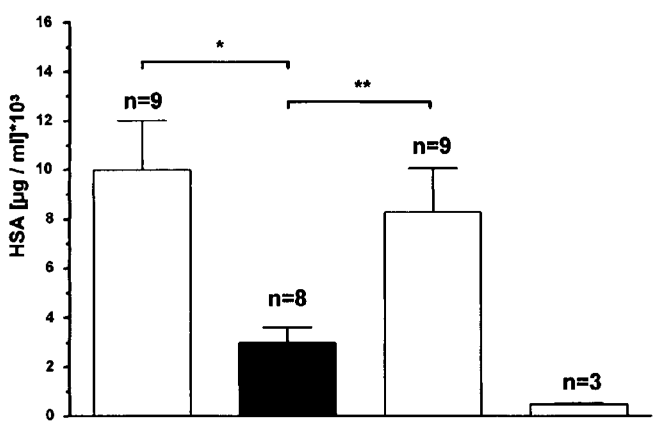
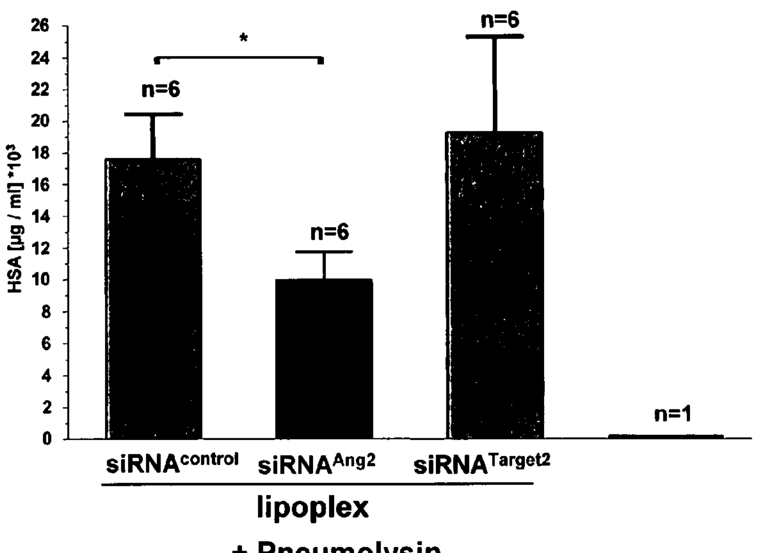
aguuggaaggaccacaugc (SEQ ID NO: 14)
gcaugugguccuuccaacu (SEQ ID NO: 15)
SEQ ID NO: 68 aguuggaaggaccacaugcguca
SEQ ID NO: 69 ugacgcauguggccuuccaacu

Fig. 9: Comparison of AtuRNAi – molecule #9 (Figure 11) to published* siRNAs, analyzed by transfection in murine B16V 1 siRNA #9 (Figure 11)- Silence Therapeutics, 23mer 2 Ang2-Bhandari *Sequence from Nat Med. 2006 Nov;12(11):1286-93 ), 21mer- Alynlam, w/ TT overhangs 3 Ang2-Bhandari 3 "Bhandari sequence" as 23mer, blunt (Extension from 3'-end)

4 Ang2-Bhandari Atu23 "Bhandari sequence" AtuRNAi 23-mer extended from 5'-end

Ang2_Bhandari_A3
5-AUUUACUGCUGAACUCCCACGGA-3′ (antisense) (SEQ ID NO: 105)
Ang2_Bhandari_B3
5'-UCCGUGGGAGUUCAGCAGUAAAU-3' (sense) (SEQ ID NO: 106)

As described w/o 2′-OM mit TT desoxy Overhangs:
Ang2_Bhandari_A
5'-AUUUACUGCUGAACUCCCATT-3' (antisense) (SEQ ID NO: 107)
Ang2_Bhandari_B
5'-UGGGAGUUCAGCAGUAAAUTT-3' (sense) (SEQ ID NO: 108)

AtuRNAi (23-mer, 2′-OM as usual):
Ang2_Bhandari_Atu23_A
5′-AGUUAUUUACUGCUGAACUCCCA-3′ (ANTI) (SEQ ID NO: 109)
Ang2_Bhandari_Atu23_B
5′-UGGGAGUUCAGCAGUAAAUAACU-3′ (SEQ ID NO: 110)

* Bhandari et al., Nat Med. 2006 Nov;12(11):1286-93: this molecules are not composed of Alnylam chemistry, as used in the paper Fig. 10: Ang2-siRNAs in B16V in efficacy comparison: TaqMan analysis
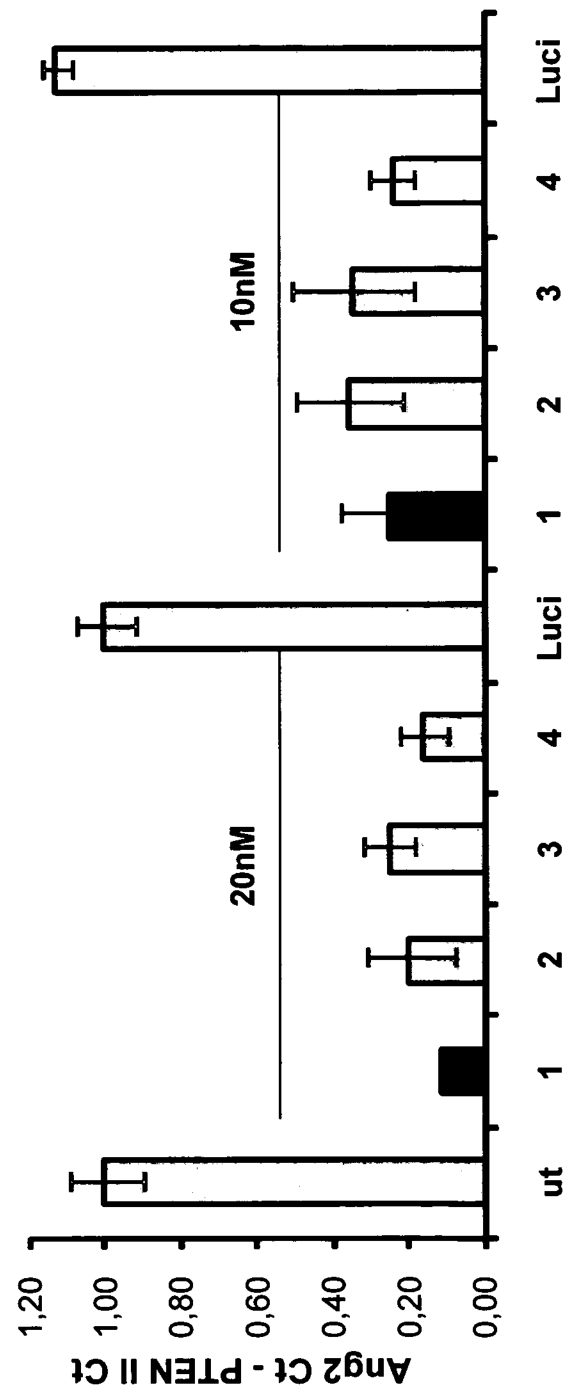

Fig. 11: Alternative Ang2-23merAtuRNAi for screening

| siRNA Molecule # | SEQ ID NO: | Strand Designation | siRNA sequence |
|---|---|---|---|
| 1 (m) | 52 | A | auauuuaacagccaggaagaaaa |
| | 53 | B | uuuucuuccuggcuguuaaauau |
| 2 (m) | 54 | A | uuauuuacugcugaacucccacg |
| | 55 | B | cgugggaguucagcaguaaauaa |
| 3 (m) | 56 | A | auauaguaaauaguagccagcca |
| | 57 | B | uggcuggcuacuauuuacuauau |
| 4 (hmr) | 58 | A | uauuuaauuacuaaaaauaccuu |
| | 59 | B | aagguauuuuuaguaauuaaaua |
| 5 (m) | 60 | A | uuucaaaugaacauguaaagcac |
| | 61 | B | gugcuuuacauguucauuugaaa |
| 6 (m) | 62 | A | aaaaguuaggaaaaugaucugcc |
| | 63 | B | ggcagaucauuuuccuaacuuuu |
| 7 (hm) | 64 | A | aucaucagguuguggccuugag |
| | 65 | B | cucaaggccacaaccaugaugau |
| 8 (hmr) | 66 | A | uucaaguuggaaggaccacaugc |
| | 67 | B | gcaugugguccuuccaacuugaa |
| 9 (m) | 68 | A | aguuggaaggaccacaugcguca |
| | 69 | B | ugacgcaugugguccuuccaacu |

Fig. 12: Screening of siRNA molecules from Fig. 11 in B16V
(B16V: 300.000 c/ 10cm - petridish; siRNA: 20 nM, Lipid: atufect01, 2 µg/ ml; Lipoplex after 4h removed; Lysis 48h post transfection; Taqman PCR )
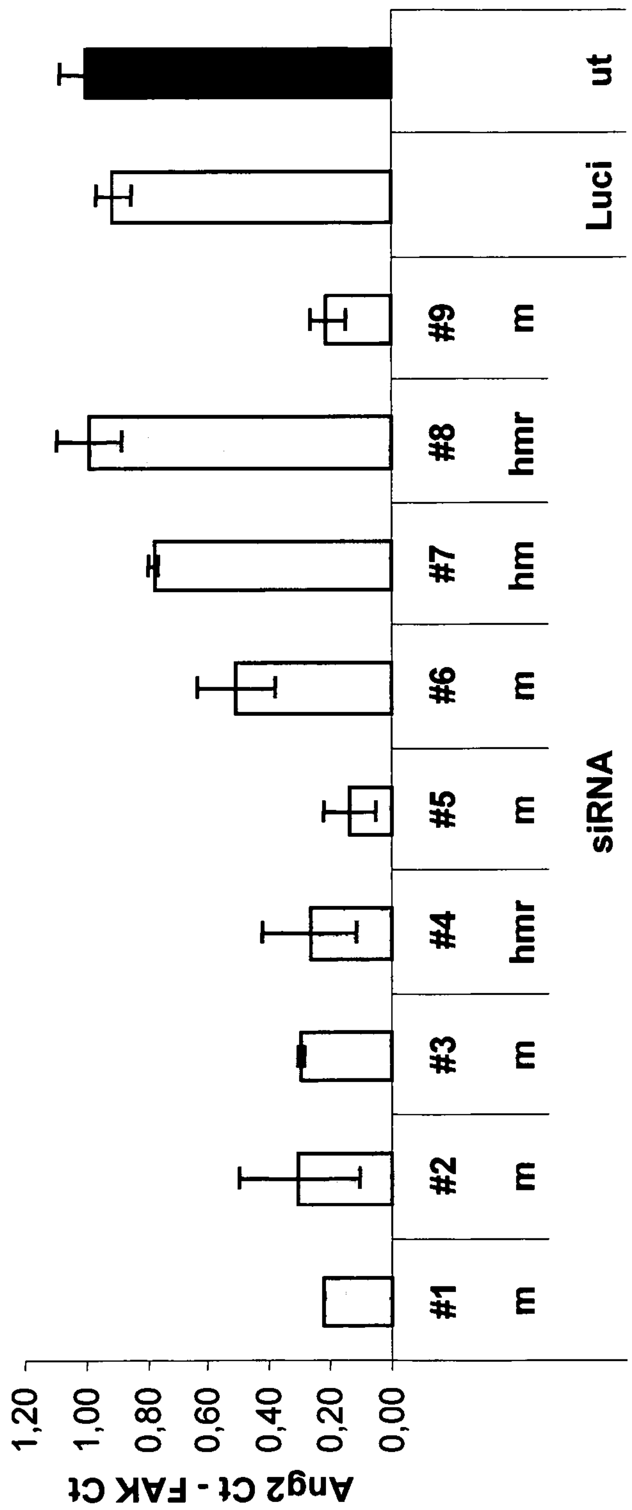

Fig. 13: Characterization of ANGPT2 siRNA in B16V
Comparison of siRNA molecules of Figure 11 in tissue culture
(B16V: 60.000 c/ 6well; siRNA – 20 … 1 nM, atufect01 – 2 µg/ ml at 20 nM siRNA; Lipoplex after 4h removed; Lysis 48h post transfection; mRNA levels measured by TaqMan PCR)
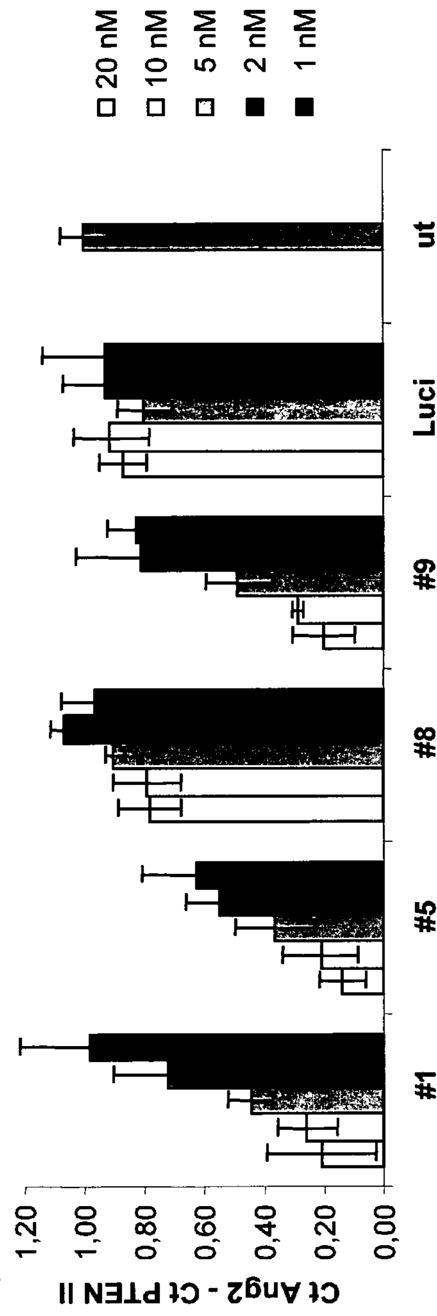
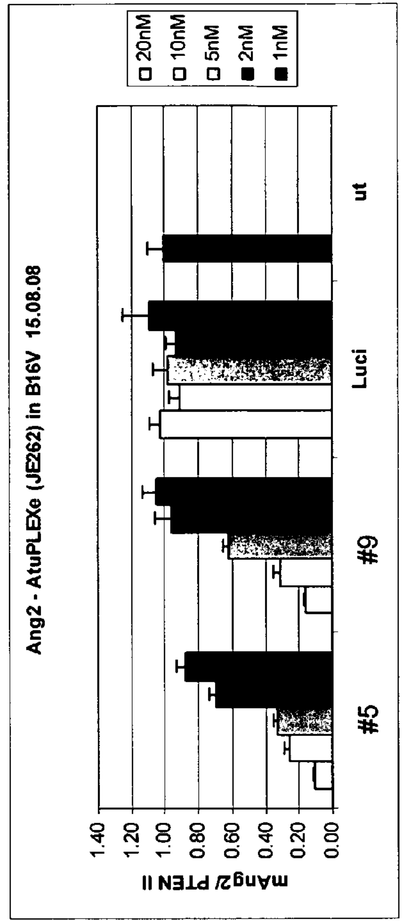
Direct efficacy comparison of AtuPLEX formulation for siRNA in vitro

Fig. 14: RNAi with extended 23-mer siRNA in murine B16V cells
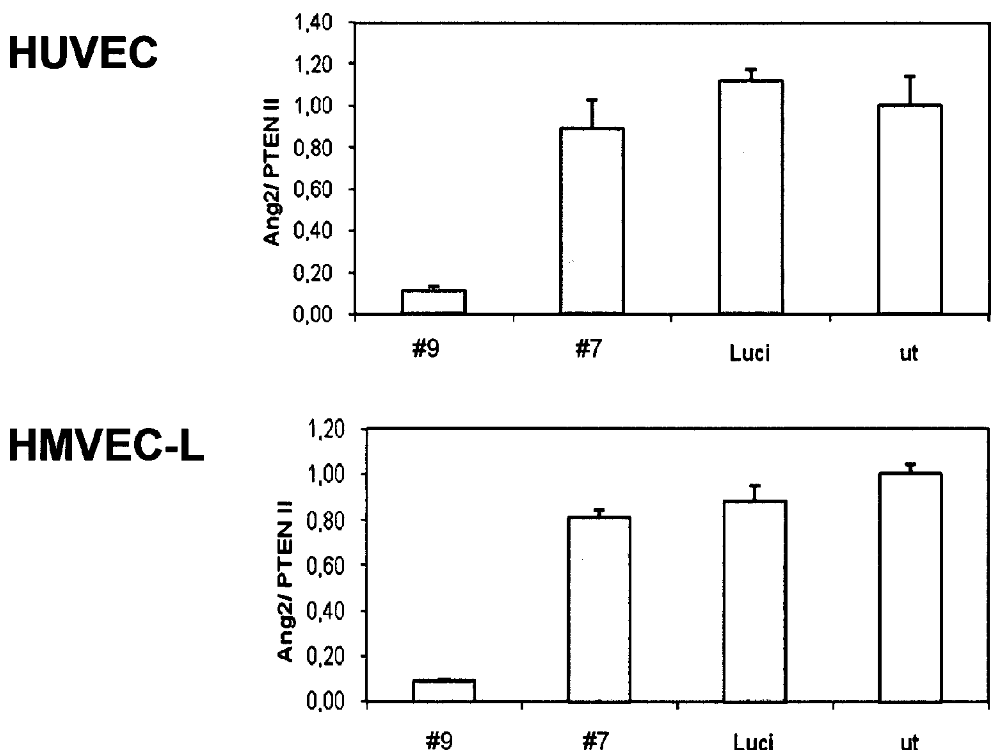
siRNA #9 (mouse-specific; 1 missmatch to human))
siRNA #7 (human, mouse, rat)
Luci: siRNA formed by sequences Luc-23-2A and Luc-23-2B
ut: untreated

Fig. 15: Comparision of two Ang2 – siRNA leads in human HUVEC Different specificity of 19mer vs 23mer variant
(HUVEC: 80.000 c/ 6well; siRNA – 20 … 1nM, atufect01 – 2 µg/ ml at 20nM; Lipoplex rinsed off 4h after transfection; lysis 48h post transfection)
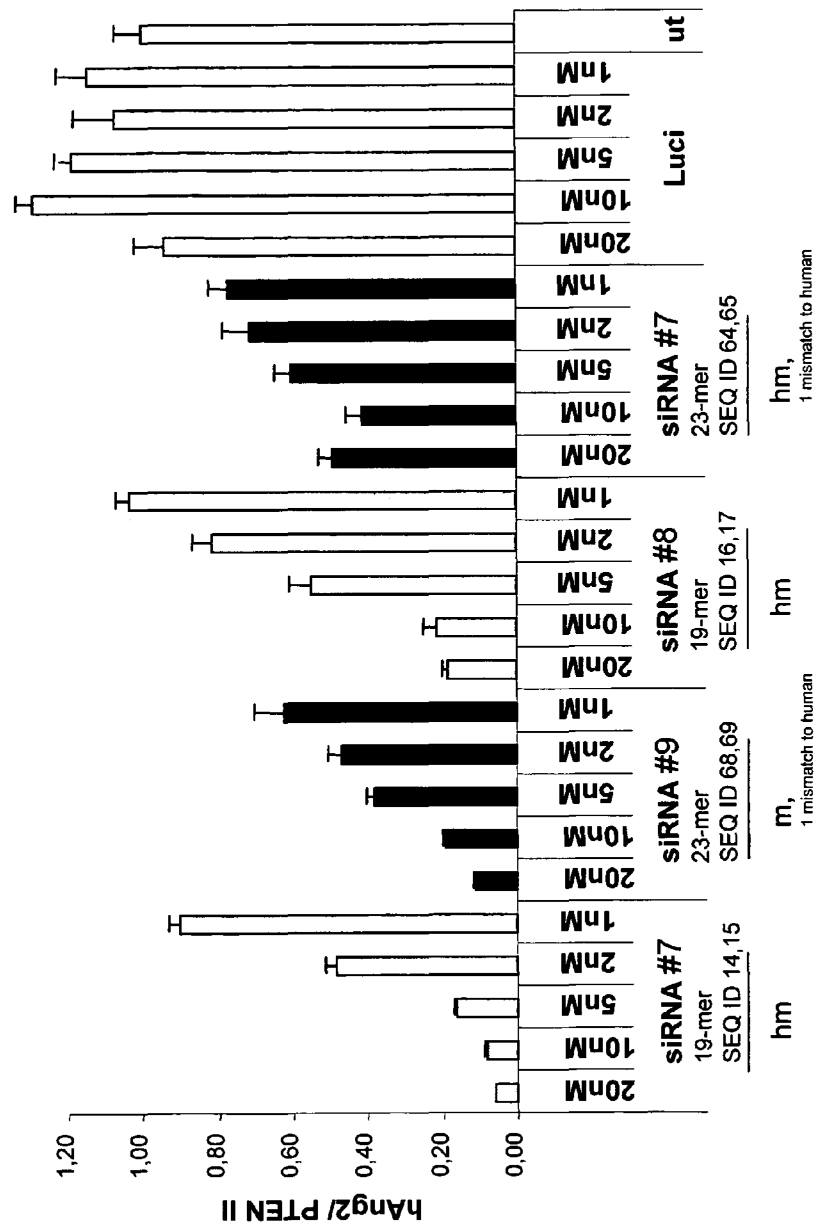

Fig. 16: Alternative Ang2-23mer AtuRNAi for screening

| siRNA molecule No. | SEQ. ID No. | Strand designation | Sequence |
|---|---|---|---|
| 11 (h) | 73 | A | uguuugucgagagggaguguucc |
| | 74 | B | ggaacacucccucucgacaaaca |
| 12 (h) | 75 | A | augaguaagccucauucccuucc |
| | 76 | B | ggaagggaaugaggcuuacucau |
| 13 (h) | 77 | A | ucaguaaguuauuaacugucucc |
| | 78 | B | ggagacaguuaauaacuuacuga |
| 14 (h) | 79 | A | cguguagaugccauucguggugu |
| | 80 | B | acaccacgaauggcaucuacacg |
| 15 (h) | 81 | A | ucccagucuuuaagguguauuuu |
| | 82 | B | aaaauacaccuuaaagacuggga |
| 16 (h) | 83 | A | ccuugagcgaauagccugagccu |
| | 84 | B | aggcucaggcuauucgcucaagg |
| 17 (h) | 85 | A | ucggaucaucaugguuguggccu |
| | 86 | B | aggccacaaccaugaugauccga |
| 18 (h) | 87 | A | gcacagcauuggacacguagggg |
| | 88 | B | ccccuacguguccaaugcugugc |
| 19 (h) | 89 | A | uuuuucuaguucuucaaugaugg |
| | 90 | B | ccaucauugaagaacuagaaaaa |
| 20 (h) | 91 | A | auuugaauacuucagcacagucu |
| | 92 | B | agacugugcugaaguauucaaau |
| 21 (h) | 93 | A | auuuguuuauuucacuggucugg |
| | 94 | B | ccagaccagugaaauaaacaaau |
| 22 (h) | 95 | A | cauuuaaugccguugaacuuauu |
| | 96 | B | aauaaguucaacggcauuaaaug |
| 23 (h) | 97 | A | acuuuauauucuuuccaaguccu |
| | 98 | B | aggacuuggaaagaauauaaagu |
| 24 (h) | 99 | A | uagaauuagggaauguuaacgug |
| | 100 | B | cacguuaacauucccuaauucua |
| 25 (h) | 101 | A | auguuuagaaaucugcuggucgg |
| | 102 | B | ccgaccagcagauuucuaaacau |
| 26 (h) | 103 | A | aguuggaaggaccacaugcauca |
| | 104 | B | ugaugcaugugguccuuccaacu |

Fig. 17: Screening human siRNA Ang2- 23mer in HUVEC
(HUVEC: 40.000 c/ 6well; siRNA: 20 nM, Lipid: atufect01, 2 µg/ ml; Lipoplex rinsed after 4h transfection; Lysis 48h post transfection)
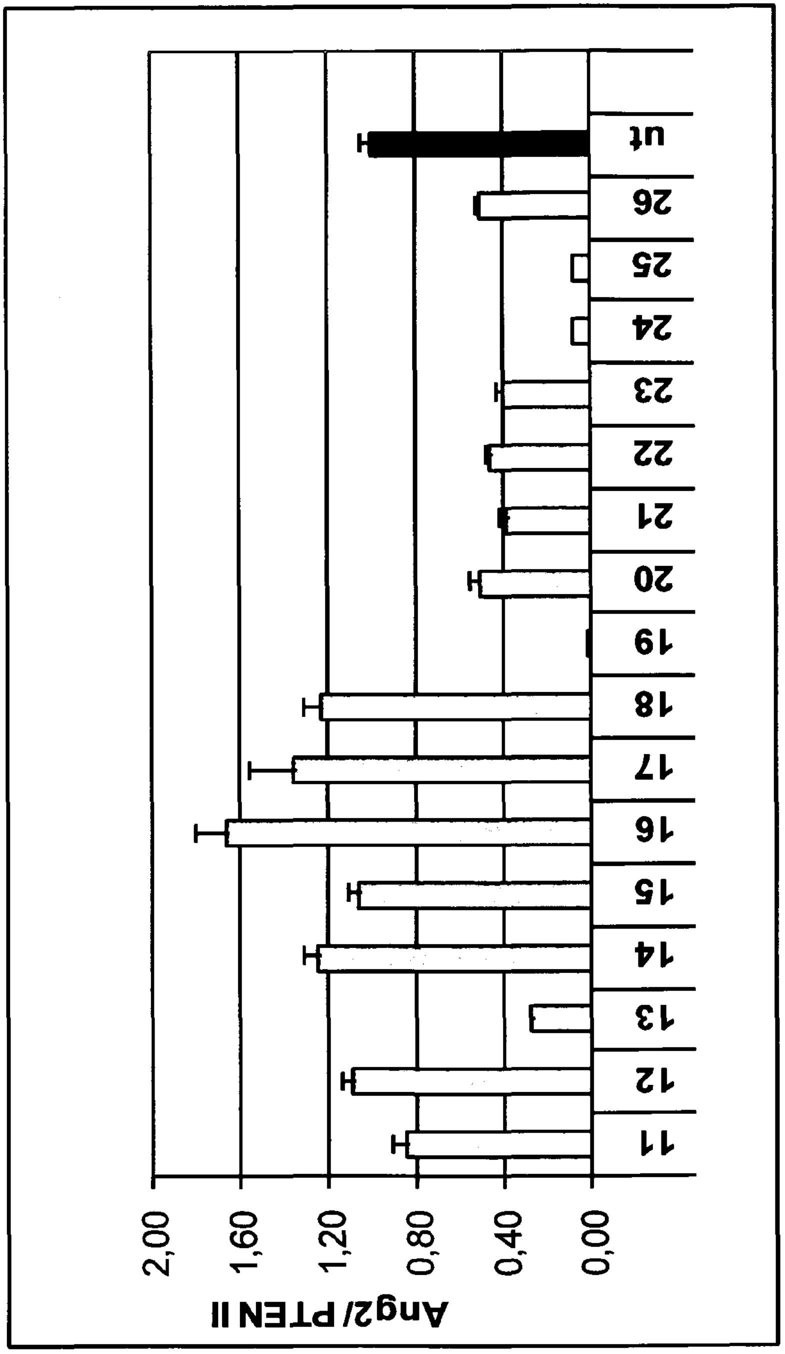
No. 26: humanized 23-mer siRNA #9
No.19: showed sample specific toxicity

Fig. 18: Characterization of human-specific Ang2-leads in HUVEC (partially crossover to cynomolgus): comparative efficacy study

(HUVEC: 40.000 c/ 6well; siRNA: 20 nM, Lipid: atufect01, 2 µg/ ml; Lipoplex rinsed off after 4h transfection; Lysis 48h post transfection)

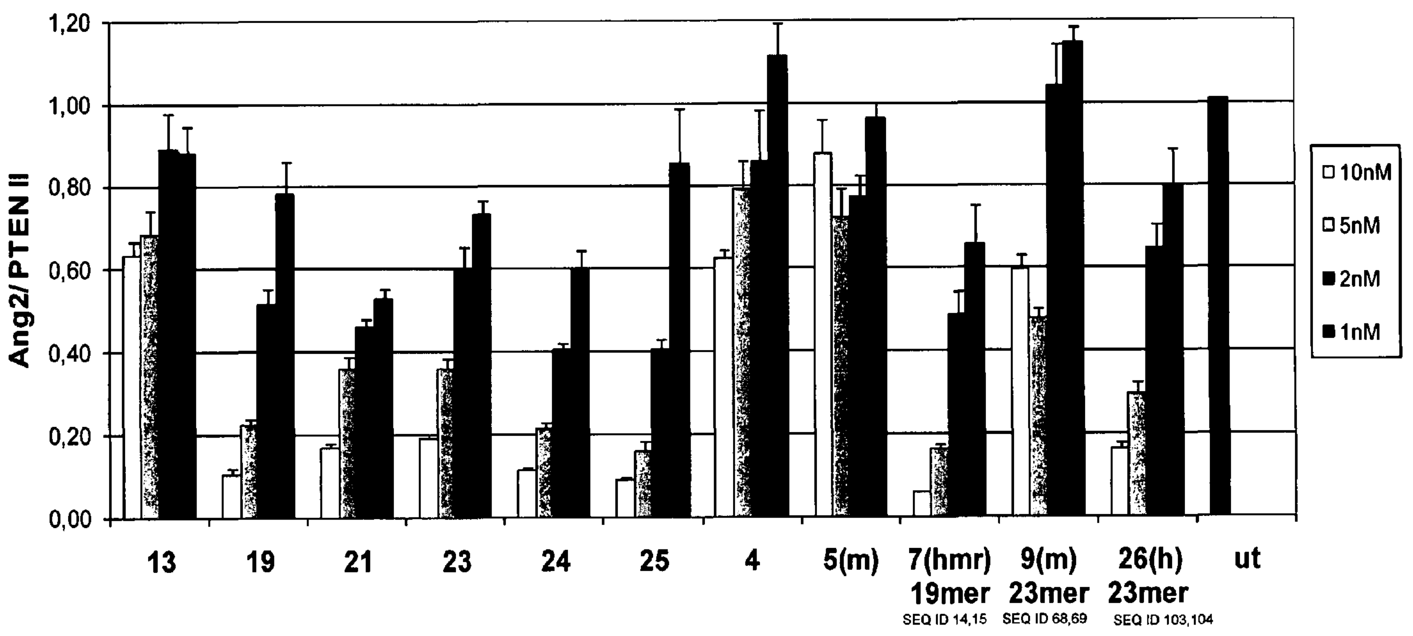

- siRNA 13, -19, -21, -23, -4, -7(hmr) 23mer, - 26(h) 23mers: match *Macaca fascicularis* predicted Ang2- cDNA
- siRNA-5: mouse-specific; see Fig.12
- siRNA-25: 2 mismatches to Maca fasc.
- siRNA-24: 15mer homologous stretch to M. fasc.

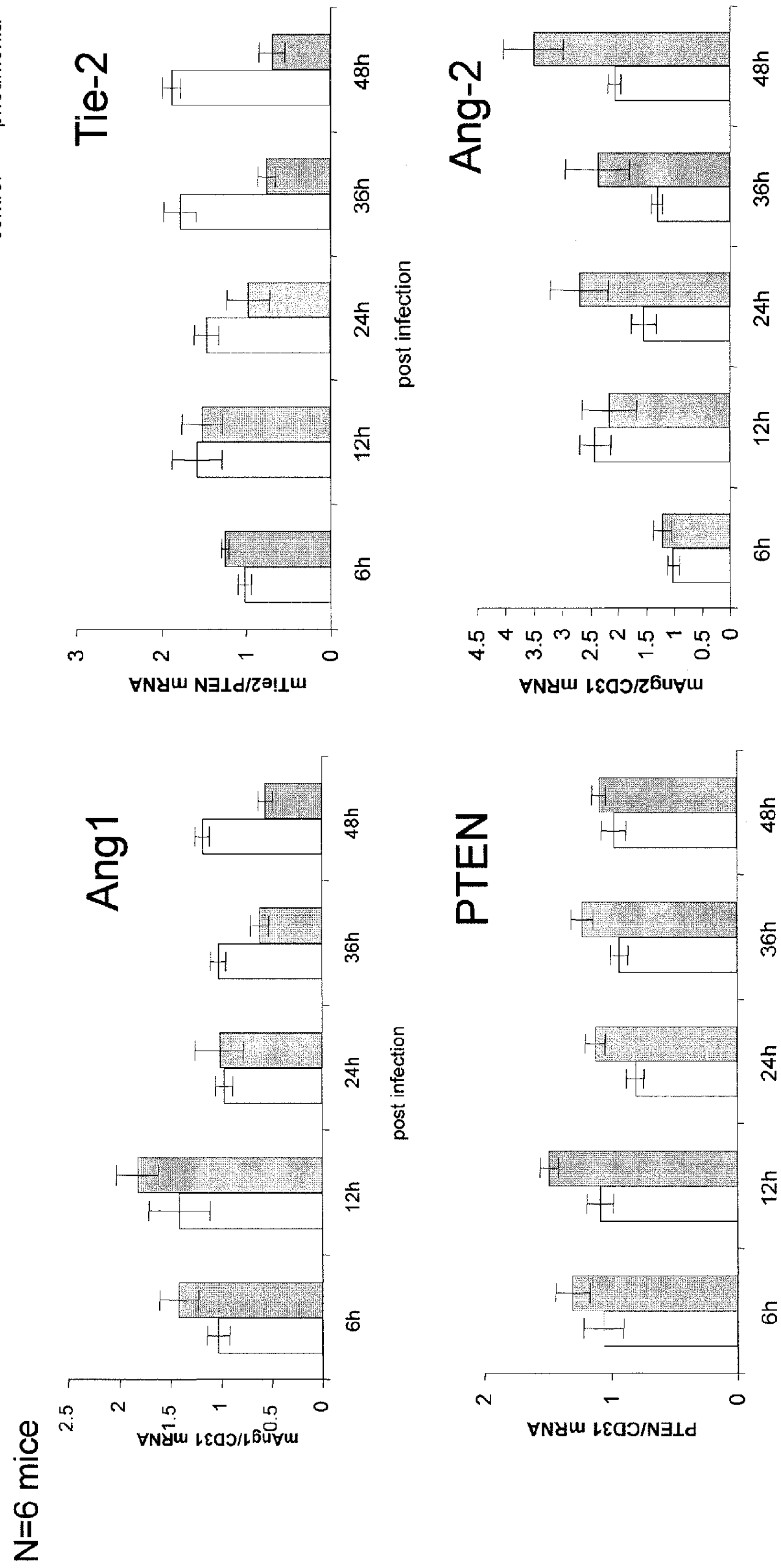
Fig. 19 A: Pneumonia infection impairs balance of Tie-2/Ang-signalling molecule expression
N=6 mice
□ control ▒ pneumonia
Ang1
mAng1/CD31 mRNA
0
0.5
1
1.5
2
2.5
6h
12h
24h
36h
48h
post infection
Tie-2
mTie2/PTEN mRNA
0
1
2
3
6h
12h
24h
36h
48h
post infection
PTEN
PTEN/CD31 mRNA
0
1
2
6h
12h
24h
36h
48h
Ang-2
mAng2/CD31 mRNA
0
0.5
1
1.5
2
2.5
3
3.5
4
4.5
6h
12h
24h
36h
48h

MEANS FOR INHIBITING THE EXPRESSION OF ANG2

CROSS-REFERENCE TO RELATED APPLICATION

This application is the U.S. national stage application of International Patent Application No. PCT/EP2010/001036, filed Feb. 18, 2010.

The Sequence Listing for this application is labeled "Seq-List-replace.txt" which was created on Aug. 19, 2013 and is 39 KB. The entire contents of the sequence listing is incorporated herein by reference in its entirety.

FIELD OF THE INVENTION

The present invention is related to a double-stranded nucleic acid suitable to inhibit the expression of ANG2 and uses thereof.

BACKGROUND OF INVENTION

The receptor tyrosine kinase Tie2 is required for vascular development and two ligands Angiopoietin (ANG1 and ANG2) have been well characterized (Fiedler and Augustin, 2006). ANG1 is expressed by perivascular cells and is an activator of Tie2. ANG1 is also required for blood vessel stabilization and maturation during development. ANG2, however, does not activate Tie2 on cultured endothelial cells (with certain exceptions). ANG2 is suggested to be selectively expressed in the endothelial cells of actively remodeling blood vessels.

There is an ongoing need in the art for means of silencing or knocking down the expression levels of ANG2 in vitro and in vivo, including the use of siRNA for the treatment of inflammatory diseases or decreasing inflammation. The present invention addresses these unmet needs through discovery of compositions, methods of using and processes of making siRNA directed to ANG2.

SUMMARY OF THE INVENTION

The present invention relates to compositions comprising short interfering RNA (siRNA) directed to an expressed RNA transcript of ANG2 (sometimes referred to as a "target nucleic acid" herein) and compositions thereof. These siRNA molecules can be used in the treatment of a variety of diseases and disorders where reduced expression of ANG2 gene product is desirable.

BRIEF DESCRIPTION OF DRAWINGS

Further features, embodiments and advantages may be taken from the following figures:

FIG. 1: Balance of powers showing grade influence of signals for the Tie2/Ang (1,2). signaling pathway.

FIG. 2: Sequences of Ang2-19mer AtuRNAi molecules designed for in vitro screening. Bolded nucleotides have been modified at the 2' position with an O-methyl group.

FIG. 3: Screening for potent Ang2-siRNA molecules (AtuRNAi-19mers) in murine B16V and MS1 cells. The siRNA-Ang2 19mers tested are as identified in FIG. 2. The designations regarding the specificity of any siRNA molecule disclosed herein is as follows: "h": human; "m": murine; "r": rat; "hm" human and murine; "hr": human and rat; "mr": murine and rat; and "hmr": human, murine and rat specific.

FIG. 4: Experimental outline for PLY-induced vascular permeability ex vivo measurement and the use of the IPML (Isolated perfused mouse lung) model.

FIG. 5: Reduced vascular permeability after treatment of siRNA$^{Ang2}$-lipoplexes as revealed by IPML (ex vivo) and Pneumonia infection (in vivo) assays. siRNA molecule #7, as identified in FIG. 2, was used in these assays.

FIG. 6: Effect of siRNA$^{Ang2}$-lipoplex treatment on in vivo permeability assay with *S. pneumoniae*. infected lungs (A). Knockdown of Ang2 and Tie2 mRNA in lungs from corresponding treatment groups (B). RNAi mediated suppression of Ang2-mRNA expression in HUVEC transfected with siRNAAng2- and siRNALuc-lipoplexes at indicated siRNA concentration (C). siRNA molecule #7, as identified in FIG. 2, was used in these assays.

FIG. 7: Extension of an ANG2 siRNA 19mer to 23-mer in B16V: The activity of siRNA #9 (FIG. 11) is compared the activity of siRNA #7; FIG. 11. The test establishes that siRNA molecule #9, as identified in FIG. 11, is a potent siRNA molecule for suppression of Ang2 mRNA expression.

FIG. 8: Reduced vascular permeability in lungs from mice i.v. treated with 19-mer or 23-mer siRNAAng2-lipoplexes. siRNA Molecule #7 (FIG. 2) and siRNA molecule #9 (FIG. 11) are compared in panels A and B respectively.

FIG. 9: Comparison of AtuRNAi molecule #9 (FIG. 11) with published siRNAs (Bhandari et al., 2006) and derivatives thereof, studied in transfection experiments.

FIG. 10: Comparison of RNAi efficacy for Ang2-siRNAs in B16V: 2 experiments at different concentrations of siRNA. Legend: 1—siRNA #9 (FIG. 11); 2—Ang2-Bhandari *Sequenz aus Nat. Med. 2006 November; 12(11):1286-93), 21mer-Alnylam, w/TT overhangs; 3—Ang2-Bhandari 3 "Bhandari-Sequenz" as 23mer, blunt (Extension from 3'-end); and 4—Ang2-Bhandari Atu23 "Bhandari-Sequenz" AtuRNAi 23-mer extended from 5'-end.

FIG. 11: Alternative Ang2-23mer AtuRNAi for screening. Nine different siRNA molecules are depicted. Bolded nucleotides have been modified at the 2' position with an O-methyl group.

FIG. 12: Screening of additional Ang2-23mers (depicted in FIG. 11) in B16V and efficacy testing.

FIGS. 13-14: Characterization of the various Ang2 siRNA molecules of FIG. 11 in B16V and in tissue culture.

FIG. 15: Efficacy testing of Ang2 lead siRNA 19-mers and corresponding 23-mers in HUVEC.

FIGS. 16-18: Alternative Ang2-23mer AtuRNAi designed for screening potent molecules against human ANG2. 16 different siRNA molecules are depicted. Potency for inhibition of ANG2 gene expression was revealed by transfection experiments in HUVEC.

BRIEF DESCRIPTION OF THE SEQUENCES

Figure 19:
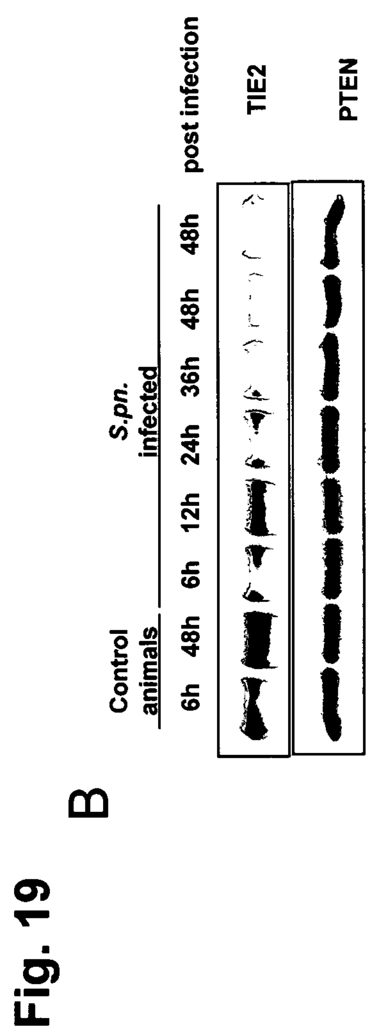
FIG. 19A: Changes in the expression levels of the components for the Tie2-Ang system observed during development of pneumonia in mice after infection with *Streptococcus pneumoniae*. Total RNA from respective samples were isolated and analyzed by TaqMan PCR in order to determine mRNA levels of Tie2, Ang1, Ang2, and PTEN in corresponding samples. The mean value for each group was plotted over time, demonstrating a decrease of mRNA levels for Ang1and Tie2 in infected mice when compared to non-infected mice over time.
FIG. 19B: Tie-2 protein levels decreased over time as shown by Western blot with protein extracts from indicated mice.

SEQ ID NO: 1 is the mRNA sequence encoding human ANG2. This sequence has been converted from the cDNA sequence provided in GenBank Accession No. NM_001147.2, which is hereby incorporated by reference in its entirety.

SEQ ID NOs: 2-69 and 73-104 are exemplary sense and antisense siRNA sequences.

SEQ ID NO: 70 is the mRNA sequence encoding murine ANG2. This sequence has been converted from the cDNA sequence provided in GenBank Accession No. NM_007426.3, which is hereby incorporated by reference in its entirety.

SEQ ID NOs: 71-72 are the mRNA sequences for variants of human ANG2. These sequences have been converted from the cDNA sequences provided in GenBank Accession Nos. NM_001118887.1 and NM_001118888.1, respectively. Each of these GenBank Accession Nos. is hereby incorporated by reference in its entirety.

DETAILED DESCRIPTION

The present invention relates to compositions comprising short interfering RNA (siRNA) directed to an expressed RNA transcript of ANG2 (sometimes referred to as a "target nucleic acid" herein). The siRNA of the invention are nucleic acid molecules comprising a double stranded or duplex region. The present invention further relates to methods of using the siRNA compositions to reduce the expression level of ANG2. As used herein, the terms "silence" or "knock-down" when referring to gene expression means a reduction in gene expression. The present invention further relates to processes for making the siRNA.

In one aspect, the target nucleic acid is an RNA expressed from a mammalian ANG2 gene. In one embodiment, the target nucleic acid is an RNA expressed from mouse ANG2. In another embodiment, the target nucleic acid is an RNA expressed from human ANG2. In another embodiment, the target nucleic acid is a human ANG2 mRNA. In another embodiment, the target nucleic acid is a human ANG2 mRNA. In another embodiment, the target nucleic acid is an mRNA comprising the sequence of SEQ ID NO: 1, 70, 71 or 72.

The siRNA of the present invention are suitable to inhibit the expression of ANG2. The siRNA according to the present invention is, thus, suitable to trigger the RNA interference response resulting in the reduction of the ANG2 mRNA in a mammalian cell. The siRNA according to the present invention are further suitable to decrease the expression of ANG2 protein by decreasing gene expression at the level of mRNA.

siRNA Design:

An siRNA of the present invention comprises two strands of a nucleic acid, a first, antisense strand and a second, sense strand. The nucleic acid normally consists of ribonucleotides or modified ribonucleotides however; the nucleic acid may comprise deoxynucleotides (DNA) as described herein. The siRNA further comprises a double-stranded nucleic acid portion or duplex region formed by all or a portion of the antisense strand and all or a portion of the sense strand. The portion of the antisense strand forming the duplex region with the sense strand is the antisense strand duplex region or simply, the antisense duplex region, and the portion of the sense strand forming the duplex region with the antisense strand is the sense strand duplex region or simply, the sense duplex region. The duplex region is defined as beginning with the first base pair formed between the antisense strand and the sense strand and ending with the last base pair formed between the antisense strand and the sense strand, inclusive. The portion of the siRNA on either side of the duplex region is the flanking regions. The portion of the antisense strand on either side of the antisense duplex region is the antisense flanking regions. The portion of the antisense strand 5' to the antisense duplex region is the antisense 5' flanking region. The portion of the antisense strand 5' to the antisense duplex region is the antisense 3' flanking region. The portion of the sense strand on either side of the sense duplex region is the sense flanking regions. The portion of the sense strand 5' to the sense duplex region is the sense 5' flanking region. The portion of the sense strand 5' to the sense duplex region is the sense 3' flanking region.

Complementarity:

In one aspect, the antisense duplex region and the sense duplex region may be fully complementary and are at least partially complementary to each other. Such complementarity is based on Watson-Crick base pairing (i.e., A:U and G:C base pairing). Depending on the length of a siRNA a perfect match in terms of base complementarity between the antisense and sense duplex regions is not necessarily required however, the antisense and sense strands must be able to hybridize under physiological conditions.

In one embodiment, the complementarity between the antisense strand and sense strand is perfect (no nucleotide mismatches or additional/deleted nucleotides in either strand).

In one embodiment, the complementarity between the antisense duplex region and sense duplex region is perfect (no nucleotide mismatches or additional/deleted nucleotides in the duplex region of either strand).

In another embodiment, the complementarity between the antisense duplex region and the sense duplex region is not perfect. In one embodiment, the identity between the antisense duplex region and the complementary sequence of the sense duplex region is selected from the group consisting of at least 75%, 80%, 85%, 90% and 95%; wherein a siRNA comprising the antisense duplex region and the sense duplex region is suitable for reducing expression of ANG2. In another embodiment, the siRNA, wherein the identity between the antisense duplex region and complementary sequence of the sense duplex region is selected from the group consisting of at least 75%, 80%, 85%, 90% and 95%, is able to reduce expression of ANG2 by at least 25%, 50% or 75% of a comparative siRNA having a duplex region with perfect identity between the antisense duplex region and the sense duplex region. As used herein the term "comparative siRNA" is a siRNA that is identical to the siRNA to which it is being compared, except for the specified difference, and which is tested under identical conditions.

RNAi using siRNA involves the formation of a duplex region between all or a portion of the antisense strand and a portion of the target nucleic acid. The portion of the target nucleic acid that forms a duplex region with the antisense strand, defined as beginning with the first base pair formed between the antisense strand and the target sequence and ending with the last base pair formed between the antisense strand and the target sequence, inclusive, is the target nucleic acid sequence or simply, target sequence. The duplex region formed between the antisense strand and the sense strand may, but need not be the same as the duplex region formed between the antisense strand and the target sequence. That is, the sense strand may have a sequence different from the target sequence however; the antisense strand must be able to form a duplex structure with both the sense strand and the target sequence.

In one embodiment, the complementarity between the antisense strand and the target sequence is perfect (no nucleotide mismatches or additional/deleted nucleotides in either nucleic acid).

In one embodiment, the complementarity between the antisense duplex region (the portion of the antisense strand forming a duplex region with the sense strand) and the target sequence is perfect (no nucleotide mismatches or additional/deleted nucleotides in either nucleic acid).

In another embodiment, the complementarity between the antisense duplex region and the target sequence is not perfect. In one embodiment, the identity between the antisense duplex region and the complementary sequence of the target sequence is selected from the group consisting of at least 75%, 80%, 85%, 90% or 95%, wherein a siRNA comprising the antisense duplex region is suitable for reducing expression of ANG2. In another embodiment, the siRNA, wherein the identity between the antisense duplex region and complementary sequence of the target sequence is selected from the group consisting of at least 75%, 80%, 85%, 90% and 95%, is able to reduce expression of ANG2 by at least 25%, 50% or 75% of a comparative siRNA with perfect identity to the antisense strand and target sequence.

In another embodiment, the siRNA of the invention comprises a duplex region wherein the antisense duplex region has a number of nucleotides selected from the group consisting of 1, 2, 3, 4 and 5 that are not base-paired to a nucleotide in the sense duplex region, and wherein said siRNA is suitable for reducing expression of ANG2. Lack of base-pairing is due to either lack of complementarity between bases (i.e., no Watson-Crick base pairing) or because there is no corresponding nucleotide on either the antisense duplex region or the sense duplex region such that a bulge is created. In one embodiment, a siRNA comprising an antisense duplex region having a number of nucleotides selected from the group consisting of 1, 2, 3, 4 and 5 that are not base-paired to the sense duplex region, is able to reduce expression of ANG2 by at least 25%, 50%, 75% of a comparative siRNA wherein all nucleotides of said antisense duplex region are base paired with all nucleotides of said sense duplex region.

In another embodiment, the antisense strand has a number of nucleotides selected from 1, 2, 3, 4, 5, 6, 7, 8, 9 or 10 that do not base-pair to the sense strand, and wherein a siRNA comprising said antisense strand is suitable for reducing expression of ANG2. Lack of complementarity is due to either lack of complementarity between bases or because there is no corresponding nucleotide on either the antisense strand or the sense strand. The lack of a corresponding nucleotide results in either a single-stranded overhang or a bulge (if in the duplex region), in either the antisense strand or the sense strand. In one embodiment, a siRNA comprising an antisense strand having a number of nucleotides selected from 1, 2, 3, 4, 5, 6, 7, 8, 9 or 10 that do not base pair to the sense strand, is able to reduce expression of ANG2 by at least 25%, 50%, 75% of a comparative siRNA wherein all nucleotides of said antisense strand are complementary to all nucleotides of the sense strand. In one embodiment, a siRNA comprising an antisense strand having a number of nucleotides selected from 1, 2, 3, 4, 5, 6, 7, 8, 9 or 10 that are mismatched to the target sequence, is able to reduce expression of ANG2 by at least 25%, 50%, 75% of a comparative siRNA wherein all nucleotides of said antisense strand are complementary to all nucleotides of said sense strand. In another embodiment, all of the mismatched nucleotides are outside the duplex region.

In another embodiment, the antisense duplex region has a number of nucleotides selected from 1, 2, 3, 4 or 5 that do not base-pair to the sense duplex region, and wherein a siRNA comprising said antisense duplex region is suitable for reducing expression of ANG2. Lack of complementarity is due to either lack of complementarity between bases or because there is no corresponding nucleotide on either the antisense duplex region or the sense duplex region such that a bulge in created in either the antisense duplex region or the sense duplex region. In one embodiment, a siRNA comprising an antisense duplex region having a number of nucleotides selected from the group consisting of 1, 2, 3, 4 and 5 that do not base pair to the sense duplex region, is able to reduce expression of ANG2 by at least 25%, 50%, 75% of a comparative siRNA wherein all nucleotides of said antisense duplex region are complementary to all of the nucleotides of said sense duplex region.

In another embodiment, the antisense strand has a number of nucleotides selected from 1, 2, 3, 4, 5, 6, 7, 8, 9 or 10 that do not base-pair to the target sequence, and wherein a siRNA comprising said antisense strand is suitable for reducing expression of ANG2. Lack of complementarity is due to either lack of complementarity between bases or because there is no corresponding nucleotide on either the antisense strand or the target sequence. The lack of a corresponding nucleotide results in a bulge in either the antisense strand or the target sequence. In one embodiment, a siRNA comprising an antisense strand having a number of nucleotides selected from 1, 2, 3, 4, 5, 6, 7, 8, 9 or 10 do not base pair to the target sequence, is able to reduce expression of ANG2 by at least 25%, 50%, 75% of a comparative siRNA wherein all nucleotides of said antisense strand are complementary to all nucleotides of said target sequence. In one embodiment, a siRNA comprising an antisense strand having a number of nucleotides selected from 1, 2, 3, 4, 5, 6, 7, 8, 9 or 10 that are mismatched to the target sequence, is able to reduce expression of ANG2 by at least 25%, 50% or 75% of a comparative siRNA wherein all nucleotides of said antisense strand are complementary to all nucleotides of said target sequence.

In another embodiment, the complementarity between an antisense duplex region and both a sense duplex region and a target sequence of an siRNA is such that the antisense duplex region and the sense duplex region or the target sequence hybridize to one another under physiological conditions (37° C. in a physiological buffer) and the siRNA is suitable for reducing expression of ANG2. In one embodiment, the siRNA comprising an antisense duplex region that hybridizes to a sense duplex region and a target sequence under physiological conditions, is able to reduce expression of ANG2 by at least 25%, 50%, 75% of a comparative siRNA with perfect complementarity between the antisense strand and target sequence.

In another aspect, the complementarity between an antisense duplex region and a sense duplex region of a siRNA is such that the antisense duplex region and sense duplex region hybridize under the following conditions: 400 mM NaCl, 40 mM PIPES pH 6.4, 1 mM EDTA, 70° C., and is suitable for reducing expression of ANG2. In one embodiment, the siRNA comprising an antisense duplex region and a sense duplex region that hybridize to one another under the conditions 400 mM NaCl, 40 mM PIPES pH 6.4, 1 mM EDTA, 70° C., is able to reduce expression of ANG2 by at least 25%, 50%, 75% of a comparative siRNA with perfect complementarity between the antisense duplex region and sense duplex region.

In another embodiment, the complementarity between an antisense strand of a siRNA and a target sequence is such that the antisense strand and target sequence hybridize under the following conditions: 400 mM NaCl, 40 mM PIPES pH 6.4, 1 mM EDTA, 70° C. and wherein the siRNA is suitable for reducing expression of ANG2. In one embodiment, the siRNA comprising an antisense strand that hybridizes to the target sequence under the following conditions: 400 mM NaCl, 40 mM PIPES pH 6.4, 1 mM EDTA, 70° C., is able to reduce expression of ANG2 by at least 25%, 50%, 75% of a comparative siRNA with perfect complementarity between the antisense strand and the target sequence.

Length:

RNA interference is observed using long nucleic acid molecules comprising several dozen or hundreds of base pairs, although shorter RNAi molecules are generally preferred.

In one embodiment, the length of the siRNA duplex region is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 base pairs. In one embodiment, the length of the siRNA duplex region is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 consecutive base pairs. In another embodiment, the length of the siRNA duplex region is selected from the group consisting of 16, 17, 18, 19, 20, 21, 22, 23, 24, 25, 26, 27, 28, 29, 30, 31, 32, 33, 34 and 35 base pairs. In another embodiment, the length of the siRNA duplex region is selected from the group consisting of 16, 17, 18, 19, 20, 21, 22, 23, 24, 25, 26, 27, 28, 29, 30, 31, 32, 33, 34 and 35 consecutive base pairs.

In one embodiment, the length of the antisense strand is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense stand is selected from the group consisting of 16, 17, 18, 19, 20, 21, 22, 23, 24, 25, 26, 27, 28, 29, 30, 31, 32, 33, 34 and 35 nucleotides.

In one embodiment, the length of the sense strand is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the sense stand is selected from the group consisting of 16, 17, 18, 19, 20, 21, 22, 23, 24, 25, 26, 27, 28, 29, 30, 31, 32, 33, 34 and 35 nucleotides.

In one embodiment, the length of the antisense strand and the length of the sense strand are independently selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides. In one embodiment, the length of the antisense strand and the length of the sense stand are independently selected from the group consisting of 16, 17, 18, 19, 20, 21, 22, 23, 24, 25, 26, 27, 28, 29, 30, 31, 32, 33, 34 and 35 nucleotides. In one embodiment, the antisense strand and the sense strand are equal in length. In another embodiment, the antisense strand and the sense stand are equal in length, wherein the length is selected from the group consisting of 16, 17, 18, 19, 20, 21, 22, 23, 24, 25, 26, 27, 28, 29, 30, 31, 32, 33, 34 and 35 nucleotides.

In one embodiment, the length of the antisense strand is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand comprises the nucleotide sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68.

In one embodiment, the length of the antisense strand is selected from the group consisting of about 16, 17, 18, 19, 20, 21, 22, 23, 24, 25, 26, 27, 28, 29, 30, 31, 32, 33, 34 and 35 nucleotides, wherein the antisense strand comprises the nucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68.

In one embodiment, the length of the sense strand is selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In one embodiment, the length of the sense strand is selected from the group consisting of about 16, 17, 18, 19, 20, 21, 22, 23, 24, 25, 26, 27, 28, 29, 30, 31, 32, 33, 34 and 35 nucleotides, wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In one embodiment, the length of the antisense strand and the length of the sense strand are independently selected from the group consisting of about 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand comprises the nucleotide sequence of SEQ ID NO. NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68, and wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In one embodiment, the length of the antisense strand and the length of the sense stand are independently selected from the group consisting of 16, 17, 18, 19, 20, 21, 22, 23, 24, 25, 26, 27, 28, 29, 30, 31, 32, 33, 34 and 35 nucleotides, wherein the antisense strand comprises the nucleotide sequence of SEQ ID NO. NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68, and wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In one embodiment, the antisense strand and the sense strand are equal in length, wherein the antisense strand comprises the nucleotide sequence of SEQ ID NO. NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68, and wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In another embodiment, the antisense strand and the sense stand are equal in length, wherein the length is selected from the group consisting of 16 to 35, 16 to 30, 17 to 35, 17 to 30, 17 to 25, 17 to 24, 18 to 29, 18 to 25, 18 to 24, 18 to 23, 19 to 25, 19 to 24, 19 to 23, 20 to 25, 20 to 24, 21 to 25 and 21 to 24 nucleotides, wherein the antisense strand comprises the nucleotide sequence of SEQ ID NO. NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68, and wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

In another embodiment, the antisense strand and the sense stand are equal in length, wherein the length is selected from the group consisting of 16, 17, 18, 19, 20, 21, 22, 23, 24, 25, 26, 27, 28, 29, 30, 31, 32, 33, 34 and 35 nucleotides, wherein the antisense strand comprises the nucleotide sequence of SEQ ID NO. NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64 or 68, and wherein the sense strand comprises the nucleotide sequence of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

Certain embodiments provide for antisense and sense strand combinations (identified by SEQ ID NO:): 2 and 3; 4 and 5; 6 and 7; 8 and 9; 10 and 11; 12 and 13; 14 and 15; 16 and 17; 18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44 and 45; 46 and 47; 48 and 49; 50 and 51; 52 and 53; 54 and 55; 56 and 57; 58 and 59; 60 and 61; 62 and 63; 64 and 65; 66 and 67; and 68 and 69.

Ends (Overhangs and Blunt Ends):

The siRNA of the present invention may comprise an overhang or be blunt ended. An "overhang" as used herein has its normal and customary meaning in the art, i.e., a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base paired. In one embodiment, the terminal nucleotide of an antisense strand and a sense strand at a blunt end are base paired. In another embodiment, the terminal nucleotide of an antisense strand and a sense strand at a blunt end are not paired. In another embodiment, the terminal two nucleotides of an antisense strand and a sense strand at a blunt end are base paired. In another embodiment, the terminal two nucleotides of an antisense strand and a sense strand at a blunt end are not paired.

In one embodiment, the siRNA has an overhang at one end and a blunt end at the other. In another embodiment, the siRNA has an overhang at both ends. In another embodiment, the siRNA is blunt ended at both ends. In one embodiment, the siRNA is blunt ended at one end. In another embodiment, the siRNA is blunt ended at the end with the 5'-end of the antisense strand and the 3'-end of the sense strand. In another embodiment, the siRNA is blunt ended at the end with the 3'-end of the antisense strand and the 5'-end of the sense strand. In another embodiment, the siRNA is blunt ended at both ends.

In another embodiment, the siRNA comprises a overhang at a 3'- or 5'-end. In one embodiment, the siRNA has a 3'-overhang on the antisense strand. In another embodiment, the siRNA has a 3'-overhang on the sense strand. In another embodiment, the siRNA has a 5'-overhang on the antisense strand. In another embodiment, the siRNA has a 5'-overhang on the sense strand. In another embodiment, the siRNA has an overhang at both the 5'-end and 3'-end of the antisense stand. In another embodiment, the siRNA has an overhang at both the 5'-end and 3'-end of the sense stand. In another embodiment, the siRNA has a 5' overhang on the antisense stand and a 3' overhang on the sense strand. In another embodiment, the siRNA has a 3' overhang on the antisense stand and a 5' overhang on the sense strand. In another embodiment, the siRNA has a 3' overhang on the antisense stand and a 3' overhang on the sense strand. In another embodiment, the siRNA has a 5' overhang on the antisense stand and a 5' overhang on the sense strand.

In one embodiment, the overhang at the 3'-end of the antisense strand has a length selected from the group consisting of 1, 2, 3, 4 and 5 nucleotides. In one embodiment, the overhang at the 3'-end of the sense strand has a length selected from the group consisting of 1, 2, 3, 4 and 5 nucleotides. In one embodiment, the overhang at the 5'-end of the antisense strand has a length selected from the group consisting of 1, 2, 3, 4 and 5 nucleotides. In one embodiment, the overhang at the 5'-end of the sense strand has a length selected from the group consisting of 1, 2, 3, 4 and 5 nucleotides.

Modification:

Another aspect relates to modifications of the siRNA. The siRNA according to the invention are a ribonucleic acid or a modified ribonucleic acid. Chemical modifications of the siRNA of the present invention provides a powerful tool in overcoming potential limitations including, but not limited to, in vitro and in vivo stability and bioavailability inherent to native RNA molecules. Chemically-modified siRNA can also minimize the possibility of activating interferon activity in humans. Chemical modification can further enhance the functional delivery of a siRNA to a target cell. The modified siRNA of the present invention may comprise one or more chemically modified ribonucleotides of either or both of the antisense strand or the sense strand. A ribonucleotide may comprise a chemical modification of the base, sugar or phosphate moieties.

Modifications to Base Moiety:

A secondary aspect relates to modifications to a base moiety. One or more nucleotides of a siRNA of the present invention may comprise a modified base. A "modified base" means a nucleotide base other than an adenine, guanine, cytosine or uracil at the 1' position.

In one aspect, the siRNA comprises at least one nucleotide comprising a modified base. In one embodiment, the modified base in on the antisense strand. In another embodiment, the modified base in on the sense strand. In another embodiment, the modified base is in the duplex region. In another embodiment, the modified base is outside the duplex region, i.e., in a single stranded region. In another embodiment, the modified base is on the antisense strand and is outside the duplex region. In another embodiment, the modified base is on the sense strand and is outside the duplex region. In another embodiment, the 3'-terminal nucleotide of the antisense strand is a nucleotide with a modified base. In another embodiment, the 3'-terminal nucleotide of the sense strand is nucleotide with a modified base. In another embodiment, the 5'-terminal nucleotide of the antisense strand is nucleotide with a modified base. In another embodiment, the 5'-terminal nucleotide of the sense strand is nucleotide with a modified base.

In one embodiment, a siRNA has 1 modified base. In another embodiment, a siRNA has about 2-4 modified bases. In another embodiment, a siRNA has about 4-6 modified bases. In another embodiment, a siRNA has about 6-8 modified bases. In another embodiment, a siRNA has about 8-10 modified bases. In another embodiment, a siRNA has about 10-12 modified bases. In another embodiment, a siRNA has about 12-14 modified bases. In another embodiment, a siRNA has about 14-16 modified bases. In another embodiment, a siRNA has about 16-18 modified bases. In another embodiment, a siRNA has about 18-20 modified bases. In another embodiment, a siRNA has about 20-22 modified bases. In another embodiment, a siRNA has about 22-24 modified bases. In another embodiment, a siRNA has about 24-26 modified bases. In another embodiment, a siRNA has about 26-28 modified bases. In each case the siRNA comprising said modified bases retains at least 50% of its activity as compared to the same siRNA but without said modified bases.

In one embodiment, the modified base is a purine. In another embodiment, the modified base is a pyrimidine. In another embodiment, at least half of the purines are modified. In another embodiment, at least half of the pyrimidines are modified. In another embodiment, all of the purines are modified. In another embodiment, all of the pyrimidines are modified.

In another embodiment, the siRNA comprises a nucleotide comprising a modified base, wherein the base is selected from the group consisting of 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

In another aspect, a siRNA of the present invention comprises an abasic nucleotide. The term "abasic" as used herein, refers to moieties lacking a base or having other chemical groups in place of a base at the 1' position, for example a 3',3'-linked or 5',5'-linked deoxyabasic ribose derivative. As used herein, a nucleotide with a modified base does not include abasic nucleotides. In one aspect, the siRNA comprises at least one abasic nucleotide. In one embodiment, the abasic nucleotide is on the antisense strand. In another embodiment, the abasic nucleotide is on the sense strand. In another embodiment, the abasic nucleotide is in the duplex region. In another embodiment, the abasic nucleotide is outside the duplex region. In another embodiment, the abasic nucleotide is on the antisense strand and is outside the duplex region. In another embodiment, the abasic nucleotide is on the sense strand and is outside the duplex region. In another embodiment, the 3'-terminal nucleotide of the antisense strand is an abasic nucleotide. In another embodiment, the 3'-terminal nucleotide of the sense strand is an abasic nucleotide. In another embodiment, the 5'-terminal nucleotide of the antisense strand is an abasic nucleotide. In another embodiment, the 5'-terminal nucleotide of the sense strand is an abasic nucleotide. In another embodiment, a siRNA has a number of abasic nucleotides selected from the group consisting of 1, 2, 3, 4, 5 and 6.

Modifications to Sugar Moiety:

Another secondary aspect relates to modifications to a sugar moiety. One or more nucleotides of an siRNA of the present invention may comprise a modified ribose moiety.

Modifications at the 2'-position wherein the 2'-OH is substituted include the non-limiting examples selected from the group consisting of alkyl, substituted alkyl, alkaryl-, aralkyl-, —F, —Cl, —Br, —CN, —CF3, —OCF3, —OCN, —O-alkyl, —S-alkyl, HS-alkyl-O, —O-alkenyl, —S-alkenyl, —N-alkenyl, —SO-alkyl, -alkyl-OSH, -alkyl-OH, —O-alkyl-OH, —O-alkyl-SH, —S-alkyl-OH, —S-alkyl-SH, -alkyl-5-alkyl, -alkyl-O-alkyl, —ONO2, —NO2, —N3, —NH2, alkylamino, dialkylamino-, aminoalkyl-, aminoalkoxy, aminoacid, aminoacyl-, —ONH2, —O-aminoalkyl, —O-aminoacid, —O-aminoacyl, heterocycloalkyl-, heterocycloalkaryl-, aminoalkylamino-, polyalkylamino-, substituted silyl-, methoxyethyl—(MOE), alkenyl and alkynyl. "Locked" nucleic acids (LNA) in which the 2' hydroxyl is connected, e.g., by a methylene bridge, to the 4' carbon of the same ribose sugar is further included as a 2' modification of the present invention. Preferred substitutents are 2'-methoxyethyl, 2'-OCH3,2'-O-allyl, 2'-C-allyl, and 2'-fluoro.

In one embodiment, the siRNA comprises 1-5 2'-modified nucleotides. In another embodiment, the siRNA comprises 5-10 2'-modified nucleotides. In another embodiment, the siRNA comprises 15-20 2'-modified nucleotides. In another embodiment, the siRNA comprises 20-25 2'-modified nucleotides. In another embodiment, the siRNA comprises 25-30 2'-modified nucleotides.

In one embodiment, the antisense strand comprises 1-2 2'-modified nucleotides. In one embodiment, the antisense strand comprises about 2-4 2'-modified nucleotides. In one embodiment, the antisense strand comprises about 4-6 2'-modified nucleotides. In one embodiment, the antisense strand comprises about 6-8 2'-modified nucleotides. In one embodiment, the antisense strand comprises about 8-10 2'-modified nucleotides. In one embodiment, the antisense strand comprises about 10-12 2'-modified nucleotides. In one embodiment, the antisense strand comprises about 12-14 2'-modified nucleotides. In one embodiment, the antisense strand comprises about 14-16 2'-modified nucleotides. In one embodiment, the antisense strand comprises about 16-18 2'-modified nucleotides. In one embodiment, the antisense strand comprises about 18-20 2'-modified nucleotides. In one embodiment, the antisense strand comprises about 22-24 2'-modified nucleotides. In one embodiment, the antisense strand comprises about 24-26 2'-modified nucleotides.

In one embodiment, the sense strand comprises 1-2 2'-modified nucleotides. In one embodiment, the sense strand comprises about 2-4 2'-modified nucleotides. In one embodiment, the sense strand comprises about 4-6 2'-modified nucleotides. In one embodiment, the sense strand comprises about 6-8 2'-modified nucleotides. In one embodiment, the sense strand comprises about 8-10 2'-modified nucleotides. In one embodiment, the sense strand comprises about 10-12 2'-modified nucleotides. In one embodiment, the sense strand comprises about 12-14 2'-modified nucleotides. In one embodiment, the sense strand comprises about 14-16 2'-modified nucleotides. In one embodiment, the sense strand comprises about 16-18 2'-modified nucleotides. In one embodiment, the sense strand comprises about 18-20 2'-modified nucleotides. In one embodiment, the sense strand comprises about 22-24 2'-modified nucleotides. In one embodiment, the sense strand comprises about 24-26 2'-modified nucleotides.

In one embodiment, the siRNA comprises 1-5 2'-OCH3 modified nucleotides. In another embodiment, the siRNA comprises 5-10 2'-OCH3 modified nucleotides. In another embodiment, the siRNA comprises 15-20 2'-OCH3 modified nucleotides. In another embodiment, the siRNA comprises 20-25 2'-OCH3 modified nucleotides. In another embodiment, the siRNA comprises 25-30 2'-OCH3 modified nucleotides.

In one embodiment, the antisense strand comprises 1-2 2'-OCH3 modified nucleotides. In one embodiment, the antisense strand comprises about 2-4 2'-OCH3 modified nucleotides. In one embodiment, the antisense strand comprises about 4-6 2'-OCH3 modified nucleotides. In one embodiment, the antisense strand comprises about 6-8 2'-OCH3 modified nucleotides. In one embodiment, the antisense strand comprises about 8-10 2'-OCH3 modified nucleotides. In one embodiment, the antisense strand comprises about 10-12 2'-OCH3 modified nucleotides. In one embodiment, the antisense strand comprises about 12-14 2'-OCH3 modified nucleotides. In one embodiment, the antisense strand comprises about 14-16 2'-OCH3 modified nucleotides. In one embodiment, the antisense strand comprises about 16-18 2'-OCH3 modified nucleotides. In one embodiment, the antisense strand comprises about 18-20 2'-OCH3 modified nucleotides. In one embodiment, the antisense strand comprises about 22-24 2'-OCH3 modified nucleotides. In one embodiment, the antisense strand comprises about 24-26 2'-OCH3 modified nucleotides.

In one embodiment, the sense strand comprises 1-2 2'-OCH3 modified nucleotides. In one embodiment, the sense strand comprises about 2-4 2'-OCH3 modified nucleotides. In one embodiment, the sense strand comprises about 4-6 2'-OCH3 modified nucleotides. In one embodiment, the sense strand comprises about 6-8 2'-OCH3 modified nucleotides. In one embodiment, the sense strand comprises about 8-10 2'-OCH3 modified nucleotides. In one embodiment, the sense strand comprises about 10-12 2'-OCH3 modified nucleotides. In one embodiment, the sense strand comprises about 12-14 2'-OCH3 modified nucleotides. In one embodiment, the sense strand comprises about 14-16 2'-OCH3 modified nucleotides. In one embodiment, the sense strand comprises about 16-18 2'-OCH3 modified nucleotides. In one embodiment, the sense strand comprises about 18-20 2'-OCH3 modified nucleotides. In one embodiment, the sense strand comprises about 22-24 2'-OCH3 modified nucleotides. In one embodiment, the sense strand comprises about 24-26 2'-OCH3 modified nucleotides.

In one embodiment, the siRNA duplex region comprises 1-5 2'-OCH3 modified nucleotides. In another embodiment, the siRNA duplex region comprises 5-10 2'-OCH3 modified nucleotides. In another embodiment, the siRNA duplex region comprises 15-20 2'-OCH3 modified nucleotides. In another embodiment, the siRNA duplex region comprises 20-25 2'-OCH3 modified nucleotides. In another embodiment, the siRNA duplex region comprises 25-30 2'-OCH3 modified nucleotides.

In one embodiment, the antisense duplex region comprises 1-2 2'-OCH3 modified nucleotides. In one embodiment, the antisense duplex region comprises about 2-4 2'-OCH3 modified nucleotides. In one embodiment, the antisense duplex region comprises about 4-6 2'-OCH3 modified nucleotides. In one embodiment, the antisense duplex region comprises about 6-8 2'-OCH3 modified nucleotides. In one embodiment, the antisense duplex region comprises about 8-10 2'-OCH3 modified nucleotides. In one embodiment, the antisense duplex region comprises about 10-12 2'-OCH3 modified nucleotides. In one embodiment, the antisense duplex region comprises about 12-14 2'-OCH3 modified nucleotides. In one embodiment, the antisense duplex region comprises about 14-16 2'-OCH3 modified nucleotides. In one embodiment, the antisense duplex region comprises about 16-18 2'-OCH3 modified nucleotides. In one embodiment, the antisense duplex region comprises about 18-20 2'-OCH3 modified nucleotides. In one embodiment, the antisense duplex region comprises about 22-24 2'-OCH3 modified nucleotides. In one embodiment, the antisense duplex region comprises about 24-26 2'-OCH3 modified nucleotides.

In one embodiment, the sense duplex region comprises 1-2 2'-OCH3 modified nucleotides. In another embodiment, the sense duplex region comprises about 2-4 2'-OCH3 modified nucleotides. In another embodiment, the sense duplex region comprises about 4-6 2'-OCH3 modified nucleotides. In another embodiment, the sense duplex region comprises about 6-8 2'-OCH3 modified nucleotides. In another embodiment, the sense duplex region comprises about 8-10 2'-OCH3 modified nucleotides. In another embodiment, the sense duplex region comprises about 10-12 2'-OCH3 modified nucleotides. In another embodiment, the sense duplex region comprises about 12-14 2'-OCH3 modified nucleotides. In another embodiment, the sense duplex region comprises about 14-16 2'-OCH3 modified nucleotides. In another embodiment, the sense duplex region comprises about 16-18 2'-OCH3 modified nucleotides. In another embodiment, the sense duplex region comprises about 18-20 2'-OCH3 modified nucleotides. In another embodiment, the sense duplex region comprises about 22-24 2'-OCH3 modified nucleotides. In another embodiment, the sense duplex region comprises about 24-26 2'-OCH3 modified nucleotides.

In one embodiment, the siRNA comprises an antisense strand 19 nucleotides in length and a sense strand 19 nucleotides in length, wherein said antisense strand comprises 2'-OCH3 modifications at nucleotides 1, 3, 5, 7, 9, 11, 13, 15, 17 and 19, and wherein said sense strand comprises 2'-OCH3 modifications at nucleotides 2, 4, 6, 8, 10, 12, 14, 16 and 18, wherein said antisense strand is numbered from 5'-3' and said sense strand is numbered from 3'-5'. In another embodiment, the siRNA comprises an antisense strand 20 nucleotides in length and a sense strand 20 nucleotides in length, wherein said antisense strand comprises 2'-OCH3 modifications at nucleotides 1, 3, 5, 7, 9, 11, 13, 15, 17 and 19, and wherein said sense strand comprises 2'-OCH3 modifications at nucleotides 2, 4, 6, 8, 10, 12, 14, 16, 18 and 20 wherein said antisense strand is numbered from 5'-3' and said sense strand is numbered from 3'-5'. In another embodiment, the siRNA comprises an antisense strand 21 nucleotides in length and a sense strand 21 nucleotides in length, wherein said antisense strand comprises 2'-OCH3 modifications at nucleotides 1, 3, 5, 7, 9, 11, 13, 15, 17, 19 and 21, and wherein said sense strand comprises 2'-OCH3 modifications at nucleotides 2, 4, 6, 8, 10, 12, 14, 16, 18 and 20, wherein said antisense strand is numbered from 5'-3' and said sense strand is numbered from 3'-5'. In another embodiment, the siRNA comprises an antisense strand 22 nucleotides in length and a sense strand 22 nucleotides in length, wherein said antisense strand comprises 2'-OCH3 modifications at nucleotides 1, 3, 5, 7, 9, 11, 13, 15, 17, 19 and 21, and wherein said sense strand comprises 2'-OCH3 modifications at nucleotides 2, 4, 6, 8, 10, 12, 14, 16, 18, 20 and 22, wherein said antisense strand is numbered from 5'-3' and said sense strand is numbered from 3'-5'. In another embodiment, the siRNA comprises an antisense strand 23 nucleotides in length and a sense strand 23 nucleotides in length, wherein said antisense strand comprises 2'-OCH3 modifications at nucleotides 1, 3, 5, 7, 9, 11, 13, 15, 17, 19, 21 and 23, and wherein said sense strand comprises 2'-OCH3 modifications at nucleotides 2, 4, 6, 8, 10, 12, 14, 16, 18, 20 and 22 wherein said antisense strand is numbered from 5'-3' and said sense strand is numbered from 3'-5'.

In another embodiment, the siRNA comprises an antisense strand 18-23 nucleotides in length and a sense strand 18-23 nucleotides in length, wherein said antisense strand comprises 2'-OCH3 modifications at nucleotides 3, 5, 7, 9, 11, 13, 15 and 17, and wherein said sense strand comprises 2'-OCH3 modifications at nucleotides 4, 6, 8, 10, 12, 14 and 16, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 5, 7, 9, 11, 13 and 15, and wherein said sense strand comprises 2'-OCH3 modifications at nucleotides 6, 8, 10, 12 and 14, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7, 9, 11, 13 and wherein said sense strand comprises 2'-OCH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7, 9 and 11, and wherein said sense strand comprises 2'-OCH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 7 and 9, and wherein said sense strand comprises 2'-OCH3 modifications at nucleotides 8 and 10, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-OCH3 modifications at nucleotides 9 and 11, and wherein said sense strand comprises 2'-OCH3 modifications at nucleotides 8 and 10, wherein said antisense strand is numbered from 5'-3' and said sense strand is numbered from 3'-5'.

In further embodiments, the siRNA comprises the following nucleotide sequences, wherein the sequences comprise 2'-OCH3 modifications on nucleotides indicated with a capital letter:

In another embodiment, the antisense strand comprises 1, 2, 3, 4, 5, 6, 7, 8, 9, 10, 11, 12, 13, 14, 15, 16, 17, 18, 19, 20, 21, 22, 23, 24 or 25 2'-deoxy nucleotides selected from the group consisting of:

In another embodiment, the sense strand comprises 1, 2, 3, 4, 5, 6, 7, 8, 9, 10, 11, 12, 13, 14, 15, 16, 17, 18, 19, 20, 21, 22, 23, 24 or 25 2'-deoxy nucleotides.

In another embodiment, the antisense strand comprises 1, 2, 3, 4, 5, 6, 7, 8, 9, 10, 11, 12, 13, 14, 15, 16, 17, 18, 19, 20, 21, 22, 23, 24 or 25 2'-fluoro nucleotides.

In another embodiment, the sense strand comprises 1, 2, 3, 4, 5, 6, 7, 8, 9, 10, 11, 12, 13, 14, 15, 16, 17, 18, 19, 20, 21, 22, 23, 24 or 25 2'-fluoro nucleotides.

In another embodiment, the pyrimidine nucleotides in the antisense strand are 2'-O-methylpyrimidine nucleotides.

In another embodiment, of the purine nucleotides in the antisense strand are 2'-O-methyl purine nucleotides.

In another embodiment, the pyrimidine nucleotides in the antisense strand are 2'-deoxy pyrimidine nucleotides.

In another embodiment, the purine nucleotides in the antisense strand are 2'-deoxy purine nucleotides.

In another embodiment, the pyrimidine nucleotides in the antisense strand are 2'-fluoro pyrimidine nucleotides.

In another embodiment, the purine nucleotides in the antisense strand are 2'-fluoro purine nucleotides.

In another embodiment, the pyrimidine nucleotides in the sense strand are 2'-O-methyl pyrimidine nucleotides.

In another embodiment, of the purine nucleotides in the sense strand are 2'-O-methyl purine nucleotides.

In another embodiment, the pyrimidine nucleotides in the sense strand are 2'-deoxy pyrimidine nucleotides.

In another embodiment, the purine nucleotides in the sense strand are 2'-deoxy purine nucleotides.

In another embodiment, the pyrimidine nucleotides in the sense strand are 2'-fluoro pyrimidine nucleotides.

In another embodiment, the purine nucleotides in the sense strand are 2'-fluoro purine nucleotides.

In another embodiment, the pyrimidine nucleotides in the antisense duplex region are 2'-O-methylpyrimidine nucleotides.

In another embodiment, of the purine nucleotides in the antisense duplex region are 2'-O-methyl purine nucleotides.

In another embodiment, the pyrimidine nucleotides in the antisense duplex region are 2'-deoxy pyrimidine nucleotides.

In another embodiment, the purine nucleotides in the antisense duplex region are 2'-deoxy purine nucleotides.

In another embodiment, the pyrimidine nucleotides in the antisense duplex region are 2'-fluoro pyrimidine nucleotides.

In another embodiment, the purine nucleotides in the antisense duplex region are 2'-fluoro purine nucleotides.

In another embodiment, the pyrimidine nucleotides in the sense duplex region are 2'-O-methylpyrimidine nucleotides.

In another embodiment, of the purine nucleotides in the sense duplex region are 2'-O-methyl purine nucleotides.

In another embodiment, the pyrimidine nucleotides in the sense duplex region are 2'-deoxy pyrimidine nucleotides.

In another embodiment, the purine nucleotides in the sense duplex region are 2'-deoxy purine nucleotides.

In another embodiment, the pyrimidine nucleotides in the sense duplex region are 2'-fluoro pyrimidine nucleotides.

In another embodiment, the purine nucleotides in the sense duplex region are 2'-fluoro purine nucleotides.

In another embodiment, the pyrimidine nucleotides in the antisense duplex flanking regions are 2'-O-methylpyrimidine nucleotides.

In another embodiment, of the purine nucleotides in the antisense duplex flanking regions are 2'-O-methyl purine nucleotides.

In another embodiment, the pyrimidine nucleotides in the antisense duplex flanking regions are 2'-deoxy pyrimidine nucleotides.

In another embodiment, the purine nucleotides in the antisense duplex flanking regions are 2'-deoxy purine nucleotides.

In another embodiment, the pyrimidine nucleotides in the antisense duplex flanking regions are 2'-fluoro pyrimidine nucleotides.

In another embodiment, the purine nucleotides in the antisense duplex flanking regions are 2'-fluoro purine nucleotides.

In another embodiment, the pyrimidine nucleotides in the sense duplex flanking regions are 2'-O-methylpyrimidine nucleotides.

In another embodiment, of the purine nucleotides in the sense duplex flanking regions are 2'-O-methyl purine nucleotides.

In another embodiment, the pyrimidine nucleotides in the sense duplex flanking regions are 2'-deoxy pyrimidine nucleotides.

In another embodiment, the purine nucleotides in the sense duplex flanking regions are 2'-deoxy purine nucleotides.

In another embodiment, the pyrimidine nucleotides in the sense duplex flanking regions are 2'-fluoro pyrimidine nucleotides.

In another embodiment, the purine nucleotides in the sense duplex flanking regions are 2'-fluoro purine nucleotides.

Pattern:

In one aspect, the antisense duplex region comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense duplex region is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense duplex region comprise a modified base. In another embodiment, the nucleotides of said modified groups comprise a modified phosphate backbone. In another embodiment, the nucleotides of said modified groups comprise a modified 2' position.

In another aspect, the sense duplex region comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense duplex region is identical. In another embodiment, each flanking group has an equal number of nucleotides. In another embodiment, each flanking group is identical. In another embodiment, the nucleotides of said modified groups in the sense duplex region comprise a modified base. In another embodiment, the nucleotides of said modified groups comprise a modified phosphate backbone. In another embodiment, the nucleotides of said modified groups comprise a modified 2' position.

In another aspect, the antisense duplex region and the sense duplex region each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense duplex region and the sense duplex region are identical. In another embodiment, each flanking group in the antisense duplex region and the sense duplex region each have an equal number of nucleotides. In another embodiment, each flanking group in the antisense duplex region and in the sense duplex region are identical. In another embodiment, the nucleotides of said modified groups in the antisense duplex region and the sense duplex region each comprise the same modified groups and the same flanking groups. In another embodiment, the nucleotides of said modified groups in the antisense duplex region and the sense duplex region each comprise a modified base. In another embodiment, the nucleotides of said modified groups in the antisense duplex region and the sense duplex region each comprise a modified phosphate backbone. In another embodiment, the nucleotides of said modified groups in the antisense duplex region and the sense duplex region each comprise a modified 2' position.

In one aspect, the antisense strand comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense strand is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense strand comprise a modified base. In another embodiment, the nucleotides of said modified groups comprise a modified phosphate backbone. In another embodiment, the nucleotides of said modified groups comprise a modified 2' position.

In another aspect, the sense strand comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense strand is identical. In another embodiment, each flanking group has an equal number of nucleotides. In another embodiment, each flanking group is identical. In another embodiment, the nucleotides of said modified groups in the sense strand comprise a modified base. In another embodiment, the nucleotides of said modified groups comprise a modified phosphate backbone. In another embodiment, the nucleotides of said modified groups comprise a modified 2' position.

In another aspect, the antisense strand and the sense strand each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense strand and the sense strand are identical. In another embodiment, each flanking group in the antisense strand and the sense strand each have an equal number of nucleotides. In another embodiment, each flanking group in the antisense strand and in the sense strand are identical. In another embodiment, the nucleotides of said modified groups in the antisense strand and the sense strand each comprise the same modified groups and the same flanking groups. In another embodiment, the nucleotides of said modified groups in the antisense strand and the sense strand each comprise a modified base. In another embodiment, the nucleotides of said modified groups in the antisense strand and the sense strand each comprise a modified phosphate backbone. In another embodiment, the nucleotides of said modified groups in the antisense strand and the sense strand each comprise a modified 2' position.

In another aspect, the modified groups and the flanking groups form a regular pattern on the antisense stand. In another aspect, the modified groups and the flanking groups form a regular pattern on the sense strand. In one embodiment, the modified groups and the flanking groups form a regular pattern on the both the antisense strand and the sense strand. In another embodiment, the modified groups and the flanking groups form a regular pattern on the antisense duplex region. In another aspect, the modified groups and the flanking groups form a regular pattern on the sense duplex region. In one embodiment, the modified groups and the flanking groups form a regular pattern on the both the antisense duplex region and the sense duplex region.

In another aspect, the pattern is a spatial or positional pattern. A spatial or positional pattern means that (a) nucleotide(s) are modified depending on their position within the nucleotide sequence of a double-stranded portion. Accordingly, it does not matter whether the nucleotide to be modified is a pyrimidine or a purine. Rather the position of a modified nucleotide is dependent upon: (a) its numbered position on a strand of nucleic acid, wherein the nucleotides are numbered from the 5'-end to the 3'-end with the 5'-end nucleotide of the strand being position one (both the antisense strand and sense strand are numbered from their respective 5'-end nucleotide), or (b) the position of the modified group relative to a flanking group. Thus, according to this embodiment, the modification pattern will always be the same, regardless of the sequence which is to be modified.

In another embodiment, the number of modified groups on the antisense strand is selected from 1, 2, 3, 4, 5, 6, 7, 8, 9, 10, 11, 12, 13 or 14. In another embodiment, the number of modified groups on the sense strand is selected from 1, 2, 3, 4, 5, 6, 7, 8, 9, 10, 11, 12, 13 or 14. In another embodiment, the number of flanking groups on the antisense strand of nucleic acid is selected from 1, 2, 3, 4, 5, 6, 7, 8, 9, 10, 11, 12, 13 or 14. In another embodiment, the number of flanking groups on the sense strand of nucleic acid is selected from 1, 2, 3, 4, 5, 6, 7, 8, 9, 10, 11, 12, 13 or 14. In one embodiment, the number of modified groups and the number of flanking groups on either or both the antisense strand and the sense strand are the same.

In another embodiment, the number of modified groups on the antisense duplex region is selected 1, 2, 3, 4, 5, 6, 7, 8, 9, 10, 11, 12, 13 or 14. In another embodiment, the number of modified groups on the sense duplex region is selected from 1, 2, 3, 4, 5, 6, 7, 8, 9, 10, 11, 12, 13 or 14. In another embodiment, the number of flanking groups on the antisense duplex region of nucleic acid is 1, 2, 3, 4, 5, 6, 7, 8, 9, 10, 11, 12, 13 or 14. In another embodiment, the number of flanking groups on the sense duplex region of nucleic acid is selected from 1, 2, 3, 4, 5, 6, 7, 8, 9, 10, 11, 12, 13 or 14. In one embodiment, the number of modified groups and the number of flanking groups on either or both the antisense duplex region and the sense duplex region are the same.

In one embodiment, the number of modified groups and the number of flanking groups on a strand or on a duplex region are the same. In another embodiment, the number of modified groups and the number of flanking groups on a strand or on a duplex region are the same, wherein the number is selected from 1, 2, 3, 4, 5, 6, 7, 8, 9, 10, 11, 12, 13 or 14.

In another embodiment, the number of nucleotides in a modified group is selected from 1, 2, 3, 4, 5, 6, 7, 8, 9, 10, 11, 12, 13 or 14. In another embodiment, the number of nucleotides in a flanking group is selected from 1, 2, 3, 4, 5, 6, 7, 8, 9, 10, 11, 12, 13 or 14.

In one embodiment, each modified group on both the antisense strand and the sense strand is identical. In one embodiment, each modified group on both the antisense duplex region and the sense duplex region is identical. In another embodiment, each modified group and each flanking group on both the antisense strand and the sense strand are identical. In one embodiment, each modified group and each flanking group on both the antisense duplex region and the sense duplex region are identical.

In one embodiment, each modified group, each modified group position, each flanking group and each flanking group position on both the antisense strand and the sense strand are identical. In one embodiment, each modified group, each modified group position, each flanking group and each flanking group position on both the antisense duplex region and the sense duplex region are identical. In another embodiment, the modified groups on the antisense strand are complementary with the modified groups on the sense strand (the modified groups on the antisense strand and the sense strand are perfectly aligned across from one another). In another embodiment, there are no mismatches in the modified groups such that each modified group on the antisense strand is base paired with each modified group on the sense strand. In another embodiment, each modified group on the sense strand is shifted by 1, 2, 3, 4 or 5 nucleotides relative to the modified groups on the antisense strand. For example, if each modified group on the sense strand is shifted by one nucleotide and a modified group started at position one on the antisense strand, a modified group on the sense strand would begin at position two. In another embodiment, the modified groups of the antisense strand do not overlap the modified groups of the sense strand, i.e., no nucleotide of a modified group on the antisense strand is base paired with a nucleotide of a modified group on the sense strand.

In one embodiment, deoxyribonucleotides at an end of a strand of nucleic acid are not considered when determining a position of a modified group, i.e., the positional numbering begins with the first ribonucleotide or modified ribonucleotide. In another embodiment, abasic nucleotides at an end of a strand of nucleic acid are not considered when determining a position of a modified group.

In one aspect, a modified group comprises a 5'-end nucleotide of either or both of the antisense strand and the sense strand. In another embodiment, a flanking group comprises the 5'-end nucleotide of either or both of the antisense strand and the sense strand. In another embodiment, the 5'-end nucleotide of either or both of the antisense strand and the sense strand is unmodified. In another embodiment, a modified group comprises the 5'-most nucleotide of either or both of the antisense duplex region and sense duplex region. In another embodiment, a flanking group comprises the 5'-most nucleotide of either or both of the antisense duplex region or the sense duplex region. In another embodiment, the 5'-most nucleotide of either or both of the antisense duplex region or the sense duplex region is unmodified. In another embodiment, the nucleotide at position 10 of the antisense strand is unmodified. In another embodiment, the nucleotide at position 10 of the sense strand is modified. In another embodiment, a modified group comprises the nucleotide at position 10 of the sense strand.

In one embodiment, the modification at the 2' position is selected from the group comprising amino, fluoro, methoxy, alkoxy and $C_1$-$C_3$-alkyl. In another embodiment, the modification is 2'-O-methyl.

In another aspect, each modified group consists of one nucleotide and each flanking group consists of one nucleotide. In one embodiment, each modified group on the antisense strand is aligned with a flanking group on the sense strand.

In another aspect, each modified group consists of one 2'-O-methyl modified nucleotide and each flanking group consists of one nucleotide. In one embodiment, each flanking group consists of one unmodified nucleotide. In one embodiment, each flanking group consists of one 2'-O-methyl modified nucleotide. In another embodiment, each modified group on both the antisense strand and the sense strand consists of one 2'-O-methyl modified nucleotide and each flanking group on both the antisense strand and the sense strand consists of one nucleotide, wherein no modified group on one strand is either aligned or both aligned and base paired with another modified group on the other strand and no flanking group on one strand is either aligned or both aligned and base paired with a flanking group on the other strand. In another embodiment, excluding any optional overhangs, each modified group on each strand is either aligned or both aligned and based paired with a flanking group on the other strand. In one embodiment, the flanking group is unmodified. In another embodiment, the nucleotide of position one on the antisense strand is 2'-O-methyl modified.

In another embodiment, the 5'-most nucleotide of the antisense duplex region is 2'-O-methyl modified.

Positional modification schemes are described in international patent application WO 2004/015107, incorporated by reference in its entirety.

Modifications to Phosphate Backbone:

Another secondary aspect relates to modifications to a phosphate backbone. All or a portion of the nucleotides of the siRNA of the invention may be linked through phosphodiester bonds, as found in unmodified nucleic acid. A siRNA of the present invention however, may comprise a modified phosphodiester linkage. The phosphodiester linkages of either the antisense stand or the sense strand may be modified to independently include at least one heteroatom selected from the group consisting of nitrogen and sulfur. In one embodiment, a phosphoester group connecting a ribonucleotide to an adjacent ribonucleotide is replaced by a modified group. In one embodiment, the modified group replacing the phosphoester group is selected from the group consisting of phosphothioate, methylphosphonate or phosphoramidate group.

In one embodiment, all of the nucleotides of the antisense strand are linked through phosphodiester bonds. In another embodiment, all of the nucleotides of the antisense duplex region are linked through phosphodiester bonds. In another embodiment, all of the nucleotides of the sense strand are linked through phosphodiester bonds. In another embodiment, all of the nucleotides of the sense duplex region are linked through phosphodiester bonds. In another embodiment, the antisense strand comprises a number of modified phosphoester groups selected from 1, 2, 3, 4, 5, 6, 7, 8, 9 or 10. In another embodiment, the antisense duplex region comprises a number of modified phosphoester groups selected from 1, 2, 3, 4, 5, 6, 7, 8, 9 or 10. In another embodiment, the sense strand comprises a number of modified phosphoester groups selected from 1, 2, 3, 4, 5, 6, 7, 8, 9 or 10. In another embodiment, the sense duplex region comprises a number of modified phosphoester groups selected from 1, 2, 3, 4, 5, 6, 7, 8, 9 or 10.

5' And 3' End Modifications:

Another secondary aspect relates to 5' and 3' modifications. The siRNA of the present invention may include nucleic acid molecules comprising one or more modified nucleotides, abasic nucleotides, acyclic or deoxyribonucleotide at the terminal 5'- or 3'-end on either or both of the sense or antisense strands. In one embodiment, the 5'- and 3'-end nucleotides of both the sense and antisense strands are unmodified. In another embodiment, the 5'-end nucleotide of the antisense strand is modified. In another embodiment, the 5'-end nucleotide of the sense strand is modified. In another embodiment, the 3'-end nucleotide of the antisense strand is modified. In another embodiment, the 3'-end nucleotide of the sense strand is modified. In another embodiment, the 5'-end nucleotide of the antisense strand and the 5'-end nucleotide of the sense strand are modified. In another embodiment, the 3'-end nucleotide of the antisense strand and the 3'-end nucleotide of the sense strand are modified. In another embodiment, the 5'-end nucleotide of the antisense strand and the 3'-end nucleotide of the sense strand are modified. In another embodiment, the 3'-end nucleotide of the antisense strand and the 5'-end nucleotide of the sense strand are modified. In another embodiment, the 3'-end nucleotide of the antisense strand and both the 5'- and 3'-end nucleotides of the sense strand are modified. In another embodiment, both the 5'- and 3'-end nucleotides of the antisense strand are modified. In another embodiment, both the 5'- and 3'-end nucleotides of the sense strand are modified.

In another embodiment, the 5'-end nucleotide of the antisense strand is phosphorylated. In another embodiment, the 5'-end nucleotide of the sense strand is phosphorylated. In another embodiment, the 5'-end nucleotides of both the antisense strand and the sense strand are phosphorylated. In another embodiment, the 5'-end nucleotide of the antisense strand is phosphorylated and the 5'-end nucleotide of the sense strand has a free hydroxyl group (5'-OH). In another embodiment, the 5'-end nucleotide of the antisense strand is phosphorylated and the 5'-end nucleotide of the sense strand is modified.

Modifications to the 5'- and 3'-end nucleotides are not limited to the 5' and 3' positions on these terminal nucleotides. Examples of modifications to end nucleotides include, but are not limited to, biotin, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described, e.g., in PCT patent application WO 99/54459, European patents EP 0 586 520 B1 or EP 0 618 925 B 1, incorporated by reference in their entireties. As used herein, “alkyl” means $C_1$-$C_{12}$-alkyl and “lower alkyl” means $C_1$-$C_6$-alkyl, including $C_1$-, $C_2$-, $C_3$-, $C_4$-, $C_5$- and $C_6$-alkyl.

In another aspect, the 5'-end of the antisense strand, the 5'-end of the sense strand, the 3'-end of the antisense strand or the 3'-end of the sense strand is covalently connected to a prodrug moiety. In one embodiment, the moiety is cleaved in an endosome. In another the moiety is cleaved in the cytoplasm.

Various possible non-limiting embodiments of the siRNA of the present invention having different kinds of end modification(s) are presented in the following Table.

Various embodiments of the interfering ribonucleic acid according to the present invention

| | | Antisense strand | Sense strand |
|---|---|---|---|
| 1.) | 5'-end | free OH | free OH |
| | 3'-end | free OH | free OH |
| 2.) | 5'-end | free OH | free OH |
| | 3'-end | end modification | end modification |
| 3.) | 5'-end | free OH | free OH |
| | 3'-end | free OH | end modification |
| 4.) | 5'-end | free OH | free OH |
| | 3'-end | end modification | free OH |
| 5.) | 5'-end | free OH | end modification |
| | 3'-end | free OH | free OH |
| 6.) | 5'-end | free OH | end modification |
| | 3'-end | end modification | free OH |
| 7.) | 5'-end | free OH | end modification |
| | 3'-end | free OH | end modification |
| 8.) | 5'-end | free OH | end modification |
| | 3'-end | end modification | end modification |

In another embodiment, the terminal 3' nucleotide or two terminal 3'-nucleotides on either or both of the antisense strand or sense strand is a 2'-deoxynucleotide. In another embodiment, the 2'-deoxynucleotide is a 2'-deoxy-pyrimidine. In another embodiment, the 2'-deoxynucleotide is a 2' deoxy-thymidine.

shRNA and Linked siRNA:

Another aspect relates to shRNA and linked siRNA. It is within the present invention that the double-stranded structure is formed by two separate strands, i.e. the antisense strand and the sense strand. However, it is also with in the present invention that the antisense strand and the sense strand are covalently linked to each other. Such linkage may occur between any of the nucleotides forming the antisense strand and sense strand, respectively. Such linkage can be formed by covalent or non-covalent linkages. Covalent linkage may be formed by linking both strands one or several times and at one or several positions, respectively, by a compound preferably selected from the group comprising methylene blue and bifunctinoal groups. Such bifunctional groups are preferably selected from the group comprising bis(2-chloroethyl)amine, N-acetyl-N'-(p-glyoxylbenzoyl)cystamine, 4-thiouracile and psoralene.

In one aspect, the antisense strand and the sense strand are linked by a loop structure. In another embodiment, of the loop structure is comprised of a non-nucleic acid polymer. In another embodiment, the non-nucleic acid polymer is polyethylene glycol. In another embodiment, the 5'-end of the antisense strand is linked to the 3'-terminus of the sense strand. In another embodiment, the 3'-end of the antisense strand is linked to the 5'-end of the sense strand.

In another aspect, the loop consists of a nucleic acid. As used herein, locked nucleic acid (LNA) (Elayadi and Corey (2001) Curr Opin Investig Drugs. 2(4):558-61) and peptide nucleic acid (PNA) (reviewed in Faseb J. (2000) 14:1041-1060) are regarded as nucleic acids and may also be used as loop forming polymers. In one embodiment, the nucleic acid is ribonucleic acid. In one embodiment, the 5'-terminus of the antisense strand is linked to the 3'-terminus of the sense strand. In another embodiment, the 3'-end of the antisense strand is linked to the 5'-terminus of the sense strand. The loop consists of a minimum length of four nucleotides or nucleotide analogues. In one embodiment, the loop consists of a length of nucleotides or nucleotide analogues selected from 4, 5, 6, 7, 8, 9, 10, 11, 12, 13, 14 or 15. In one embodiment, the length of the loop is sufficient for linking the two strands covalently in a manner that a back folding can occur through a loop structure or similar structure. The ribonucleic acid constructs may be incorporated into suitable vector systems. Preferably the vector comprises a promoter for the expression of RNAi. Preferably the respective promoter is pol III and more preferably the promoters are the U6, H1, 7SK promoter as described in Good et al. (1997) *Gene Ther,* 4, 45-54.

In another aspect, the nucleic acid according to the present invention comprises a phosphorothioate internucleotide linkage. In one embodiment, a phosphorothioate internucleotide linkage is within 5 nucleotides from the 3'-end or the 5'-end of either or both of the antisense strand and the sense strand. The antisense strand can comprise about one to about five phosphorothioate internucleotide linkages.

Combinations of Embodiments

In one embodiment, an overhang at the 3'-end of the sense strand is selected from consisting of 1, 2, 3, 4 and 5 nucleotides in length. In one embodiment, an overhang at the 5'-end of the antisense strand is selected from consisting of 1, 2, 3, 4 and 5 nucleotides in length.

In one embodiment, an overhang at the 5'-end of the sense strand is selected from consisting of 1, 2, 3, 4 and 5 nucleotides in length.

In one embodiment, the siRNA molecule is blunt-ended on both ends and has a length selected from the group consisting of 16, 17, 18, 19, 20, 21, 22, 23, 24, 25, 26, 27, 28 or 29 consecutive nucleotides.

In one embodiment, the siRNA molecule is blunt-ended on one end and the double stranded portion of the siRNA molecule has a length selected from the group consisting of 16, 17, 18, 19, 20, 21, 22, 23, 24, 25, 26, 27, 28 or 29 consecutive nucleotides.

In one embodiment, the siRNA molecule has overhangs on both ends and the double stranded portion of the siRNA molecule has a length selected from the group consisting of 16, 17, 18, 19, 20, 21, 22, 23, 24, 25, 26, 27, 28 or 29 consecutive nucleotides.

In one embodiment, the siRNA molecule comprises an overhang, said overhang comprising at least one deoxyribonucleotide. In one embodiment, the siRNA molecule comprises an overhang, said overhang comprising two deoxyribonucleotides.

In one embodiment, the siRNA molecule has overhangs on the 3'-end of the antisense strand and at the 3'-end of the sense strand, said overhangs comprising at least one deoxyribonucleotide. In one embodiment, the siRNA molecule has overhangs on the 3'-end of the antisense strand and at the 3'-end of the sense strand, said overhangs consisting two deoxyribonucleotides.

The nucleotide(s) forming the overhang may be (a) deoxyribonucleotide(s), (a) ribonucleotide(s) or a combination thereof. In one embodiment, the antisense strand and/or the sense strand comprise a TT dinucleotide at the 3' end.

Processes of Making:

The nucleic acid of the present invention can be produced using routine methods in the art including chemically synthesis or expressing the nucleic acid either in vitro (e.g., run off transcription) or in vivo. In one embodiment, the siRNA is produced using solid phase chemical synthesis. In another embodiment, the nucleic acid is produced using an expression vector. In one embodiment, the expression vector produced the nucleic acid of the invention in the target cell. Accordingly, such vector can be used for the manufacture of a medicament. Methods for the synthesis of the nucleic acid molecule described herein are known to the ones skilled in the art. Such methods are, among others, described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.,* 74, 59, Brennan et al., 1998, *Biotechnol Bioeng.,* 61, 33-45, and Brennan, U.S. Pat. No. 6,001,311 (each incorporated herein by reference in their entireties).

Surprisingly, it has been found that siRNAs targeting the following sequences of ANG2 have surprisingly high activity in terms of reducing the expression of ANG2. ANG2 expression showed to be upregulated upon infection with *Streptococcus pneumoniae* (pneumonia disease). Concomitantly, ANG1, the receptor activating ligand (counterpart to ANG2), and TIE2 expression were surprisingly downregulated, implying a concerted gene expression pattern upon the stimulus. To date, the spatial expression pattern, in particular, the distribution on the cellular level (alveolar and bronchial epithelial or endothelial) under induced as well as non-induced is not clear.

An initial screen for potent siRNA molecules revealed two out of eight molecules tested with similar high Ang2 silencing efficacy (SEQ ID NOs: 14 and 16). Surprisingly, 3'-end extension by four additional nucleotides on the antisense strand of SEQ ID Nos: 14 and 16 and the corresponding complementary sequences at the 5' end of the sense strand (SEQ ID NO:

15 and 17) gave rise to 23-mer molecules (SEQ ID NOs: 48 and 50 (antisense) and SEQ ID NOs: 49 and 51 (sense strand) which show differences in efficacy on ANG2 silencing after transfection experiments. More surprisingly, the newly generated 23-mer sequence (siRNA #9) reflecting 100% homology to the sense strand in the murine ANG2-mRNA, but not to the human homologous mRNA (one mismatch) was still capable of silencing ANG2 expression in human derived endothelial cell lines (HUVEC and HMVEC-L). In contrast, the sequence (siRNA #7), exhibiting full homology to human ANG2, showed unexpectedly no silencing efficacy (FIG. 14).

The regulation of vascular barrier function (vascular permeability) has a tremendous impact on the progression of pneumonia, or more general, acute lung injury, (ALI) and other inflammatory disease syndromes sustained by vascular leakage. In contrast, other scientific reports suggest either a contribution of ANG2 upregulation in pulmonary epithelial cells for the onset/progression of acute lung injury (Bhandari et al., 2006), or an autocrine protective/agonistic effect of induced ANG2 (Daly et al. 2006) rather than the presumed antagonistic action. Viewed in this light, we unexpectedly found that intravenous administration of liposomally formulated siRNA (AtuPLEX, Santel et al. 2006) resulted in down-regulation of ANG2 expression to some degree in lung tissue, most likely in pulmonary vascular endothelial cells, and give rise to improved vascular barrier function. This is in sharp contrast to reports where inhalation of non-formulated siRNA inhibited the progression of hypoxia induced acute lung injury. Although in accordance with the present invention, in principle, any part of the mRNA coding for ANG2 can be used for the design of such siRNA molecule and RNAi molecule, respectively, the present inventors have surprisingly found that the sequence starting with nucleotide positions set forth in the following tables provide siRNA molecules suitable to decreasing the expression of ANG2 mRNA.

| Position | |
|---|---|
| Human NM_001147.2 (SEQ ID NO: 1) | Mouse NM_007426.3 (SEQ ID NO: 70) |
| 738-756 | — |
| 758-776 | 702-720 |
| 859-877 | 803-821 |
| 1258-1276 | 1202-1220 |
| 1474-1492 | — |
| 1592-1610 | 1536-1554 |
| 1674-1692 | 1618-1636 |
| 1783-1801 | 1727-1745 |
| — | 754-772 |
| 810-828 | — |
| — | 1373-1391 |
| 1429-1447 | — |
| 738-756 | — |
| 758-776 | 702-720 |
| 859-877 | 803-821 |
| 1258-1276 | 1202-1220 |
| 1474-1492 | — |
| 1592-1610 | 1536-1554 |
| 1674-1692 | 1618-1636 |
| 1783-1801 | 1727-1745 |
| — | 754-772 |
| 810-828 | — |
| — | 1373-1391 |
| 1429-1447 | — |
| — | 2420-2442 |
| 2564-2586 | — |
| — | 2032-2054 |
| 2130-2152 | — |
| — | 2321-2343 |
| 2466-2488 | — |

-continued

| Position | |
|---|---|
| Human NM_001147.2 (SEQ ID NO: 1) | Mouse NM_007426.3 (SEQ ID NO: 70) |
| 2588-2610 | 2444-2466 |
| — | 2261-2283 |
| 2395-2417 | — |
| — | 278-300 |
| 334-356 | — |
| 1779-1801 | 1723-1745 |
| 1674-1696 | 1618-1640 |
| — | 2420-2442 |
| 2564-2586 | — |
| — | 2032-2054 |
| 2130-2152 | — |
| — | 2321-2343 |
| 2466-2488 | — |
| 2588-2610 | 2444-2466 |
| — | 2261-2283 |
| 2395-2417 | — |
| — | 278-300 |
| 334-356 | — |
| 1779-1801 | 1723-1745 |
| 1674-1696 | 1618-1640 |

Delivery/Formulations:

siRNA can be delivered to cells, both in vitro and in vivo, by a variety of methods known to those of skill in the art, including direct contact with cells ("naked" siRNA) or by in combination with one or more agents that facilitate targeting or delivery into cells. Such agents and methods include lipoplexes, liposomes, iontophoresis, hydrogels, cyclodextrins, nanocapsules, micro- and nanospheres and proteinaceous vectors (e.g., Bioconjugate Chem. (1999) 10:1068-1074 and WO 00/53722). The nucleic acid/vehicle combination may be locally delivered in vivo by direct injection or by use of an infusion pump. The siRNA of the invention can be delivered in vivo by various means including intravenous subcutaneous, intramuscular or intradermal injection or inhalation. The molecules of the instant invention can be used as pharmaceutical agents. Preferably, pharmaceutical agents prevent, modulate the occurrence, or treat (alleviate a symptom to some extent, preferably all of the symptoms) of a disease state in a subject.

There is also provided the use of a composition comprising surface-modified liposomes containing poly (ethylene glycol) lipids (PEG-modified, or long-circulating liposomes or stealth liposomes). These formulations offer a method for increasing stability of a liposome or lipoplex solutions by preventing their aggregation and fusion. The formulations also have the added benefit in vivo of resisting opsonization and elimination by the mononuclear phagocytic system (MPS or RES), thereby enabling longer blood circulation times and enhanced tissue exposure for the encapsulated drug. Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24780; Choi et al., International PCT Publication No. WO 96/10391; Ansell et al., International PCT Publication No. WO 96/10390; Holland et al., International PCT Publication No. WO 96/10392). Long-circulating liposomes also protect the siRNA from nuclease degradation.

The siRNA of the present invention may be formulated as pharmaceutical compositions. The pharmaceutical compositions may be used as medicaments or as diagnostic agents, alone or in combination with other agents. For example, one or more siRNAs of the invention can be combined with a delivery vehicle (e.g., liposomes) and excipients, such as carriers, diluents. Other agents such as preservatives and stabilizers can also be added. Methods for the delivery of nucleic acid molecules are known in the art and described, e.g., in Akhtar et al., 1992, Trends Cell Bio., 2, 139; Delivery Strategies for Antisense Oligonucleotide Therapeutics, ed. Akhtar, 1995, Maurer et al., 1999, Mol. Memb. Biol., 16, 129-140; Hofland and Huang, 1999, Handb. Exp. Pharmacol., 137, 165-192; and Lee et al., 2000, ACS Symp. Ser., 752, 184-192, U.S. Pat. No. 6,395,713 and PCT WO 94/02595 (each of which are incorporated herein by reference in their entireties). The siRNA of the present invention can also be administered in combination with other therapeutic compounds, either administrated separately or simultaneously, e.g., as a combined unit dose. In one embodiment, the invention includes a pharmaceutical composition comprising one or more siRNA according to the present invention in a physiologically/pharmaceutically acceptable excipient, such as a stabilizer, preservative, diluent, buffer, and the like.

Dosage levels for the medicament and pharmaceutical compositions of the invention can be determined by those skilled in the art by routine experimentation. In one embodiment, a unit dose contains between about 0.01 mg/kg and about 100 mg/kg body weight of siRNA. In one embodiment, the dose of siRNA is about 10 mg/kg and about 25 mg/kg body weight. In one embodiment, the dose of siRNA is about 1 mg/kg and about 10 mg/kg body weight. In one embodiment, the dose of siRNA is about 0.05 mg/kg and about 5 mg/kg body weight. In another embodiment, the dose of siRNA is about 0.1 mg/kg and about 5 mg/kg body weight.

In another embodiment, the dose of siRNA is about 0.1 mg/kg and about 1 mg/kg body weight. In another embodiment, the dose of siRNA is about 0.1 mg/kg and about 0.5 mg/kg body weight. In another embodiment, the dose of siRNA is about 0.5 mg/kg and about 1 mg/kg body weight.

In one aspect, the pharmaceutical composition is a sterile injectable aqueous suspension or solution. In one aspect, the pharmaceutical composition is in lyophilized form. In one embodiment, the pharmaceutical composition comprises lyophilized lipoplexes, wherein the lipoplexes comprises a siRNA of the present invention. In another embodiment, the pharmaceutical composition comprises an aqueous suspension of lipoplexes, wherein the lipoplexes comprises a siRNA of the present invention.

The pharmaceutical compositions and medicaments of the present invention may be administered to a subject (mammal) in the disclosed methods of treatment. In one embodiment, the mammal is selected from the group consisting humans, dogs, cats, horses, cattle, pig, goat, sheep, mouse, rat, hamster and guinea pig. In one embodiment, the mammal is a human. In another embodiment, the mammal is a non-human mammal.

In one embodiment, the present invention is related to lipoplexes comprising a siRNA according to the present invention. Such lipoplexes consist of siRNA and liposomes. Such lipoplexes may be used to deliver the siRNA of the invention to a target cell either in vitro or in vivo.

In one aspect, the lipoplex has a zeta-potential of about 40 to 55 mV, preferably about 45 to 50 mV. The size of the lipoplex according to the present invention is about 80 to 200 nm, about 100 to 140 nm or about 110 nm to 130 nm, as determined by dynamic light scattering (QELS) such as, e.g., by using an N5 submicron particle size analyzer from Beckman Coulter according to the manufacturer's recommendation.

In one embodiment, the liposome as forming part of the lipoplex is a positively charged liposome consisting of:

a) about 50 mol % β-arginyl-2,3-diaminopropionic acid-N-palmityl-N-oleyl-amide trihydrochloride, preferably β-(L-arginyl)-2,3-L-diaminopropionic acid-N-palmityl-N-oleyl-amide tri-hydrochloride, b) about 48 to 49 mol % 1,2-diphytanoyl-sn-glycero-3-phosphoethanolamine (DPhyPE), and c) about 1 to 2 mol % 1,2-distearoyl-sn-glycero-3-phosphoethanolamine-polyethyleneglycol, preferably N—(Carbonyl-methoxypolyethyleneglycol-2000)-1,2-distearoyl-sn-glycero-3-phosphoethanolamine sodium salt.

The lipoplex and lipid composition forming the liposomes is preferably in a carrier however, the lipoplex can also be present in a lyophilised form. The lipid composition contained in a carrier usually forms a dispersion. More preferably, the carrier is an aqueous medium or aqueous solution as also further characterised herein. The lipid composition typically forms a liposome in the carrier, whereby such liposome preferably also contains the carrier inside.

The lipid composition contained in the carrier and the carrier, respectively, preferably has an osmolarity of about 50 to 600 mosmole/kg, preferably about 250-350 mosmole/kg, and more preferably about 280 to 320 mosmole/kg.

The liposomes preferably are formed by the first lipid component and optionally also by the first helper lipid, preferably in combination with the first lipid component, preferably exhibit a particle size of about 20 to 200 nm, preferably about 30 to 100 nm, and more preferably about 40 to 80 nm. It is noted that the size of the particles follows a certain statistical distribution.

A further optional feature of the lipid composition in accordance with the present invention is that the pH of the carrier is preferably from about 4.0 to 6.0. However, also other pH ranges such as from 4.5 to 8.0, preferably from about 5.5 to 7.5 and more preferably about 6.0 to 7.0 are within the present invention.

For realizing these particular features various measures may be taken. For adjusting the osmolarity, for example, a sugar or a combination of sugars is particularly useful. Insofar, the lipid composition of the present invention may comprise one or several of the following sugars: sucrose, trehalose, glucose, galactose, mannose, maltose, lactulose, inulin and raffinose, whereby sucrose, trehalose, inulin and raffinose are particularly preferred. In a particularly preferred embodiment, the osmolarity mostly adjusted by the addition of sugar is about 300 mosmole/kg which corresponds to a sucrose solution of 270 mM or a glucose solution of 280 mM. Preferably the carrier is isotonic to the body fluid into which such lipid composition is to be administered. As used herein the term that the osmolarity is mostly adjusted by the addition of sugar means that at least about 80%, preferably at least about 90% of the osmolarity is provided by said sugar or a combination of said sugars.

If the pH of the lipid composition of the present invention is adjusted, this is done by using buffer substances which, as such, are basically known to the one skilled in the art. Preferably, basic substances are used which are suitable to compensate for the basic characteristics of the cationic lipids and more specifically of the ammonium group of the cationic head group. When adding basic substances such as basic amino acids and weak bases, respectively, the above osmolarity is to be taken into consideration. The particle size of such lipid composition and the liposomes formed by such lipid composition is preferably determined by dynamic light scattering such as by using an N5 submicron particle size analyzer from Beckman Coulter according to the manufacturer's recommendation.

If the lipid composition contains one or several nucleic acid(s), such lipid composition usually forms a lipoplex (liposome-nucleic acid complex). The more preferred concentration of the overall lipid content in the lipoplex in preferably isotonic 270 mM sucrose or 280 mM glucose is from about 0.01 to 100 mg/ml, preferably 0.01 to 40 mg/ml and more preferably 0.01 to 25 mg/ml. It is to be acknowledged that this concentration can be increased so as to prepare a reasonable stock, typically by a factor of 2 to 3. It is also within the present invention that based on this, a dilution is prepared, whereby such dilution is typically made such that the osmolarity is within the range specified above. More preferably, the dilution is prepared in a carrier which is identical or in terms of function and more specifically osmolarity similar to the carrier used in connection with the lipid composition or in which the lipid composition is contained. In the embodiment, of the lipid composition of the present invention whereby the lipid composition also comprises a nucleic acid, preferably a functional nucleic acid such as, but not limited to, a siRNA, the concentration of the functional nucleic acid, preferably of siRNA in the lipid composition is about 0.2 to 0.4 mg/ml, preferably 0.28 mg/ml, and the total lipid concentration is about 1.5 to 2.7 mg/ml, preferably 2.17 mg/ml. It is to be acknowledged that this mass ratio between the nucleic acid fraction and the lipid fraction is particularly preferred, also with regard to the charge ratio thus realized. In connection with any further concentration or dilution of the lipid composition of the present invention, it is preferred that the mass ratio and the charge ratio, respectively, realized in this particular embodiment, is preferably maintained despite such concentration or dilution.

Such concentration as used in, for example, a pharmaceutical composition, can be either obtained by dispersing the lipid in a suitable amount of medium, preferably a physiologically acceptable buffer or any carrier described herein, or can be concentrated by appropriate means. Such appropriate means are, for example, ultra filtration methods including cross-flow ultra-filtration. The filter membrane may exhibit a pore width of 1,000 to 300,000 Da molecular weight cut-off (MWCO) or 5 nm to 1 μm. Preferred is a pore width of about 10,000 to 100,000 Da MWCO. It will also be acknowledged by the one skilled in the art that the lipid composition more specifically the lipoplexes in accordance with the present invention may be present in a lyophilized form. Such lyophilized form is typically suitable to increase the shelve life of a lipoplex. The sugar added, among others, to provide for the appropriate osmolarity, is used in connection therewith as a cryo-protectant. In connection therewith it is to be acknowledged that the aforementioned characteristics of osmolarity, pH as well as lipoplex concentration refers to the dissolved, suspended or dispersed form of the lipid composition in a carrier, whereby such carrier is in principle any carrier described herein and typically an aqueous carrier such as water or a physiologically acceptable buffer, preferably an isotonic buffer or isotonic solution.

Diseases:

One aspect of the present invention provides a siRNA molecule that reduces the expression of ANG2 and that is useful for the treatment of human diseases and pathological conditions. The siRNA molecules can be used in combination with other therapeutic agents to enhance the therapeutic effects of a given treatment modality. In another aspect, the present invention provides reagents and methods useful for treating diseases and conditions characterized by undesirable or aberrant levels of ANG2 activity in a cell.

Another aspect of the present invention is using the materials and methods for the treatment of hyperproliferative conditions of the skin (e.g., psoriasis and/or contact dermatitis) or other hyperproliferative diseases. Another aspect of the present invention includes treating various retinopathies endometriosis, uterine fibroids, and other such conditions associated with dysfunctional vascular proliferation, such as endometrial microvascular growth, comprising the administration of siRNA molecules disclosed herein to a subject. Yet another aspect of the invention provides methods of treating inflammation (e.g., arthritis, rheumatoid arthritis, etc.) comprising the administration of a composition comprising a siRNA molecule as disclosed herein to a subject.

Non-limiting examples of human diseases and pathological conditions that can be treated as disclosed herein include: acute lung injury (ALI), acute respiratory distress syndrome (ARDS), artherosclerosis, hereditary hemorrhagic telangiectasia, cavernous hemangioma, angiogenesis induced obesity, transplant arteriopathy, psoriasis, diabetic retinopathy, inflammatory bowel and periodontal disease, ascites, endometriosis, menorrhagia, arthritis, pulmonary hypertension, pneumonia, pre-eclampsia, pulmonary fibrosis, emphysema, asthma, chronic obstructive pulmonary disease (COPD), pancreatitis, sepsis, thrombosis, ischemic heart disease, inflammation, multiple sclerosis, stroke and macular degeneration.

Example 1

Materials and Methods

Cell Lines

Murine B16V melanoma cells and endothelial MS-1 cells were obtained from ATCC/LGC Promochem and cultivated according to the manufacturer's recommendations. HUVECs (Lonza) were cultured in EGM-2 bullet kit medium containing EBM2+SingleQuots growth supplements.

Transfection of Cultured Cells and Quantification of mRNA Levels

Transfections of murine B16V melanoma and murine MS-1 endothelial cells with lipoplexed siRNA were carried out at indicated cell numbers and siRNA concentrations as previously described (Santel et al, 2006). 24 hours post transfection the cells were lysed and total RNA prepared (Invisorb Spin Cell RNA isolation kit, Invitek). Total RNA was subsequently used for mRNA quantification assays using the quantitative realtime RT-PCR approach (TaqMan, ABI). Normalized levels of the indicated mRNA were determined by the $2^{-(\Delta\Delta Ct)-}$ method showing expression levels for both the target and reference genes.

Systemic Delivery of siRNA Containing Lipoplexes

Systemic administration of siRNA lipoplexes to C57/Bl6 were performed by intravenous tail vein bolus injections of 200 μl solution on four consecutive days. The lipoplex solution contained siRNA at a final dose of 2.8 mg/kg complexed with 21.7 mg/kg total lipid (AtuFECT01:DPhyPE:DSPE-PEG) as described previously (Santel et al., 2006).

Lung Microvascular Leakage in Pneumococcal Pneumonia in Mice.

All animal procedures were approved by local authorities. C57/Bl6-mice were transnasally infected with $5\times10^6$ colony-forming units of *S. pneumoniae* (NCTC 7978) as described (Schmeck et al. 2004; Opitz et al., 2004). After intravenous application of human serum albumin (HSA), bronchoalveolar lavage (BAL) was performed, HSA concentration in BAL and serum was measured by enzyme linked immunosorbent assay (Bethyl, Montgomery, Tex.) (Matute-Bello et al., 2001), and the HSA BAL/serum ratio was calculated.

Isolated Perfused Mouse Lung (IPML).

Lungs of BALB/c mice were prepared as described. Briefly, anesthetized mice were tracheotomized and ventilated. After sternotomy and cannulation of left atrium and pulmonary artery, lungs were perfused with 37° C. sterile Krebs-Hensel eithydroxyethylamylopectine buffer (1 mL/min; Serag, Germany) and ventilated by negative pressure (−4.5 to −9.0 cm $H_2O$). Pulmonary arterial pressure (Ppa) and venous pressure were continuously monitored by pressure transducers and digitized. The areas under the Ppa curves (AUC) were calculated with Graph-Pad-4 Software (San Diego, Calif., USA).Recombinant PLY was prepared as described (Paton et al., 1993) and either infused into the pulmonary artery or intratracheally aerosolized using a microsprayer (Penn-Century, Philadelphia, Pa.). For measurement of alveolocapillary permeability, HSA was admixed to the perfusate (0.04%) before PLY application. Thirty minutes after PLY challenge, BAL was performed, and the HSA concentration was measured in BAL supernatant. In vivo data are expressed as mean+/−SEM. Differences were analyzed by one way analysis of variance followed by Student-Newman-Keuls' test.

Example 2

ANG-2 Specific siRNA Molecules

The siRNA molecules (AtuRNAi, see Tables 1 and 2.) which are directed to the mRNA encoding Angiopoietin-2 (Ang-2) and the various siRNA molecules directed to Luciferase and which were used in connection with the experiments and examples described herein, were synthesized by BioSpring (Frankfurt a. M., Germany) and are indicated in Table 1 in terms of the sequences of both the first strand and the second strand forming the double-stranded nucleic acid molecules of the present invention.

| | |
|---|---|
| Luc-23-2A (bolded nucleotides modified at the 2' position with an O-methyl group) | **u**c**g**a**a**g**u**a**u**u**c**c**g**c**g**u**a**c**g**u**g**a**u**- |
| Luc-23-2B (bolded nucleotides modified at the 2' position with an O-methyl group) | a**u**c**a**c**g**u**a**c**g**c**g**g**a**a**u**a**c**u**u**c**g**a- |

TABLE 1A

| Strand Designation and specificity | SEQ ID NO: | Strand | Sequence (5' -> 3') |
|---|---|---|---|
| B (h) | 3 | sense | gagcaaacgcggaaguuaa-P |
| B (hm) | 5 | sense | ugauguggaagcccaagua-P |
| B (hm) | 7 | sense | agaccagugaaauaaacaa-P |
| B (hm) | 9 | sense | aggccuacugugacaugga-P |
| B (h) | 11 | sense | aggcuuacucauuguauga-P |
| B (hm) | 13 | sense | ugauuuuagcacaaaggau-P |
| B (hm) | 15 | sense | gcaugugguccuuccaacu-P |
| B (hm) | 17 | sense | aggccacaaccaugaugau-P |
| B (m) | 19 | sense | cuccaacauucuauuucua-P |
| B (h) | 21 | sense | uuggaacacucccucucga-P |
| B (m) | 23 | sense | accgcuacgugcuuaagau-P |
| B (h) | 25 | sense | aacgcuaugugcuuaaaau-P |
| A (h) | 2 | antisense | uuaacuuccgcguuugcuc-P |
| A (hm) | 4 | antisense | uacuugggcuuccacauca-P |
| A (hm) | 6 | antisense | uuguuuauuucacuggucu-P |
| A (hm) | 8 | antisense | uccaugucacaguaggccu-P |
| A (h) | 10 | antisense | ucauacaaugaguaagccu-P |
| A (hm) | 12 | antisense | auccuuugugcuaaaauca-P |
| A (hm) | 14 | antisense | aguuggaaggaccacaugc-P |
| A (hm) | 16 | antisense | aucaucaugguuguggccu-P |
| A (m) | 18 | antisense | uagaaauagaauguuggag-P |
| A (h) | 20 | antisense | ucgagagggaguguuccaa-P |
| A (m) | 22 | antisense | aucuuaagcacguagcggu-P |
| A (h) | 24 | antisense | auuuuaagcacauagcguu-P |

TABLE 1B

| Strand Designation | SEQ ID NO: | Strand | (Sequence (5' -> 3') |
|---|---|---|---|
| B (m) | 27 | Sense | uuuucuuccuggcuguuaaauau-P |
| B (h) | 29 | Sense | uuuucugccugauuguuaaauau-P |
| B (m) | 31 | Sense | cgugggaguucagcaguaaauaa-P |
| B (h) | 33 | Sense | ugugcaaguuuaucaguaaauaa-P |
| B (m) | 35 | Sense | uggcuggcuacuauuuacuauau-P |
| B (h) | 37 | Sense | aaauacguauuucaaauuuauau-P |
| B (hmr) | 39 | Sense | aagguauuuuuaguaauuaaaua-P |
| B (m) | 41 | Sense | gugcuuuacauguucauuugaaa-P |

TABLE 1B-continued

| Strand Designation | SEQ ID NO: | Strand | (Sequence (5' -> 3') |
|---|---|---|---|
| B (h) | 43 | Sense | ugcuuuaaauuuuuauuucaaaa-P |
| B (m) | 45 | Sense | ggcagaucauuuuccuaacuuuu-P |
| B (h) | 47 | Sense | ggcagauuguuuucuuuacucug-P |
| B (hm) | 49 | Sense | cucaaggccacaaccaugaugau-P |
| B (hmr) | 51 | Sense | gcaugugguccuuccaacuugaa-P |
| A (m) | 26 | antisense | auauuuaacagccaggaagaaaa-P |
| A (h) | 28 | antisense | auauuuaacaaucaggcagaaaa-P |
| A (m) | 30 | antisense | uuauuuacugcugaacucccacg-P |
| A (h) | 32 | antisense | uuauuuacugauaaacuugcaca-P |
| A (m) | 34 | antisense | auauaguaaauaguagccagcca-P |
| A (h) | 36 | antisense | auauaaaauuugaaauacguauuu-P |
| A (hmr) | 38 | antisense | uauuuaauuacuaaaaauaccuu-P |
| A (m) | 40 | antisense | uuucaaaugaacauguaaagcac-P |
| A (h) | 42 | antisense | uuuugaaauaaaaauuuaaagca-P |
| A (m) | 44 | antisense | aaaaguuaggaaaaugaucugcc-P |
| A (h) | 46 | antisense | cagaguaaagaaaacaaucugcc-P |
| A (hm) | 48 | antisense | aucaucaugguuguggccuugag-P |
| A (hmr) | 50 | antisense | uucaaguuggaaggaccacaugc-P |

TABLE 2

| Strand Designation | SEQ ID NO: | Strand | Sequence (5' -> 3') |
|---|---|---|---|
| B (h) | 73 | Sense | ccccuacguguccaaugcugugc-P |
| B (h) | 75 | Sense | ggaacacucccucucgacaaaca-P |
| B (h) | 77 | Sense | ccagaccagugaaauaaacaaau-P |
| B(h) | 79 | Sense | ccaucauugaagaacuagaaaaa-P |
| B (h) | 81 | Sense | ggagacaguuaauaacuuacuga-P |
| B (h) | 83 | Sense | agacugugcugaaguauucaaau-P |
| B (h) | 85 | Sense | acaccacgaauggcaucuacacg-P |
| B (h) | 87 | Sense | cacguuaacauucccuaauucua-P |
| B (h) | 89 | Sense | aggacuuggaaagaauauaaagu-P |
| B (h) | 91 | Sense | aaaauacaccuuaaagacuggga-P |
| B (h) | 93 | Sense | ggaagggaaugaggcuuacucau-P |
| B (h) | 95 | Sense | ugaugcaugugguccuuccaacu-P |
| B (h) | 97 | Sense | aauaaguucaacggcauuaaaug-P |
| B (h) | 99 | Sense | aggcucaggcuauucgcucaagg-P |
| B (h) | 101 | Sense | aggccacaaccaugaugauccga-P |
| B (h) | 103 | Sense | ccgaccagcagauuucuaaacau-P |

TABLE 2-continued

| Strand Designation | SEQ ID NO: | Strand | Sequence (5' -> 3') |
|---|---|---|---|
| A (h) | 74 | Antisense | gcacagcauuggacacguagggg-P |
| A (h) | 76 | Antisense | uguuugucgagagggaguguucc-P |
| A (h) | 78 | Antisense | auuuguuuauuucacuggucugg-P |
| A (h) | 80 | Antisense | uuuuucuaguucuucaaugaugg-P |
| A (h) | 82 | Antisense | ucaguaaguuauuaacugucucc-P |
| A (h) | 84 | Antisense | auuugaauacuucagcacagucu-P |
| A (h) | 86 | Antisense | cguguagaugccauucguggugu-P |
| A (h) | 88 | Antisense | uagaauuagggaauguuaacgug-P |
| A (h) | 90 | Antisense | acuuuauauucuuuccaaguccu-P |
| A (h) | 92 | Antisense | ucccagucuuuaagguguauuuu-P |
| A (h) | 94 | Antisense | augaguaagccucauucccuucc-P |
| A (h) | 96 | Antisense | aguuggaaggaccacaugcauca-P |
| A (h) | 98 | Antisense | cauuuaaugccguugaacuuauu-P |
| A (h) | 100 | Antisense | ccuugagcgaauagccugagccu-P |
| A (h) | 102 | Antisense | ucggaucaucaugguuguggccu-P |
| A (h) | 104 | Antisense | auguuuagaaaucugcuggucgg-P |

"A" stands for the antisense strand which is also referred to herein as the first strand; "B" stands for the sense strand which is also referred to herein as the second strand. Please note that any sequence indicated in the instant application is presented in 5'→3' direction, if not explicitly indicated to the contrary.

In certain embodiments, the antisense strands (as set forth in the Tables above) can be modified at the 2' position (e.g., with a 2'-O-methyl group) on one or more odd numbered nucleotide (or on each odd numbered nucleotide) and one or more even numbered nucleotides remain unmodified (e.g., a OH group is present at the 2' position on each of the unmodified nucleotides, for example each of the unmodified nucleotides is unmodified). Sense strands can be modified on one or more even numbered nucleotide (or on each even numbered nucleotide) at the 2' position (e.g., with a 2'-O-methyl group) and one or more odd numbered nucleotides can remain unmodified (e.g., a OH group is present at the 2' position on each of the unmodified nucleotides, for example each of the odd numbered nucleotides is unmodified).

Alternative embodiments provide for antisense strands (as set forth above) that are modified at the 2' position (e.g., with a 2'-O-methyl group) on one or more even numbered nucleotide (or on each even numbered nucleotide) and sense strands are modified on one or more odd numbered nucleotide (or on each odd numbered nucleotide) at the 2' position (e.g., with a 2'-O-methyl group). One or more unmodified nucleotide is present in both the sense and antisense strands in these alternative embodiments (e.g., the unmodified nucleotides have aan OH group at the 2' position in each of these alternative embodiments). In certain embodiments, each odd numbered nucleotide is unmodified in the antisense strand and each even numbered nucleotide is unmodified in the sense strand for the alternative embodiments discussed in this paragraph.

Example 3

Lipoplex Formulation of Ang2 Specific siRNA Molecules

Lipoplex formulations containing Ang2 specific siRNA molecules are also referred to as siRNA lipoplexes or siRNA$^{Ang2}$-lipoplexes herein. The proprietary cationic lipid AtuFECT01 (β-L-arginyl-2,3-L-diaminopropionic acid-N-palmityl-N-oleyl-amide trihydrochloride, Silence Therapeutics AG), the neutral phospholipid 1,2-diphytanoyl-sn-glycero-3-phosphoethanolamine (DPhyPE) (Avanti Polar Lipids Inc., Alabaster, Ala.) and the PEGylated lipid N—(Carbonyl-methoxypolyethyleneglycol-2000)-1,2-distearoyl-sn-glycero-3-phospho-ethanolamine sodium salt (DSPE-PEG) (Lipoid GmbH, Ludwigshafen, Germany) were mixed in a molar ratio of 50/49/1 by lipid film re-hydration in 300 mM sterile RNase-free sucrose solution to a total lipid concentration of 4.34 mg/ml. Such formulation was in case of the experiments for IPML and *S. pneumoniae* infection 2.8 mg/kg siRNA complexed with 21.7 mg/kg which were injected by i.v. bolus on four consecutive days. For in vitro studies lipoplexes were generated by mixing AtuFECT01-DPhyPE at 1 μg/ml.

Example 4

Characterization of siRNA$^{ANG2}$-Lipoplexes

The Ang2 specific siRNA molecules of example 2 which were formulated as lipoplexes in accordance with example 3, were tested for their capacity to inhibit Ang2 mRNA expression in B16V, MS-1 and HUVEC, respectively. For such purpose the cultured cells were transfected with the listed siRNA$^{Ang2}$-lipolexes of Table 1A, B, or with the controls, at a final concentration of 20 nM for 48 hours. Cells were harvested and corresponding total RNA subjected to TaqMan real-time PCR analysis. Further details may be taken from example 1. As controls lipoplexes containing a luciferase specific siRNA molecule consisting of strands LUC-B and LUC-A were used. PTEN served as loading control. The results of the TaqMan-Analysis are indicated in FIG. 3, 6, 7, 10, 12, 13.

As may be taken from FIG. 3, lipoplexes containing any of the siRNA molecules formed by SEQ ID NOs: 4 and 5; SEQ ID NOs: 14 and 15; SEQ ID NOs: 14 and 15; SEQ ID NOs: 16 and 17; SEQ ID NOs: 18 and 19; and SEQ ID NOs: 22 and 23 were particularly effective in inhibiting the expression of Ang-2 in both B16V and MS-1 cells, whereas those Ang-2-specific lipoplexes containing any siRNA molecules formed by SEQ ID NOs: 6 and 7; SEQ ID NOs: 8 and 9; or SEQ ID NOs: 10 and 11 were inactive or only active to certain extent in one of the tested cell lines (FIG. 3).

The siRNAs formed by SEQ ID NOS: 14 and 15 or SEQ ID Nos: 16 and 17 were the most potent in both cell lines. Extension of these siRNA constructs, at the 3'-end of antisense gave rise to effective 23-mer siRNA molecules (formed by SEQ ID NOs: 48 and 49 and SEQ ID NOs: 50 and 51). The siRNA formed by SEQ ID NOs: 48 and 49 were found to be the most potent (FIG. 7) in both this assay and when tested in human cell lines (FIG. 14) (although the sequence of the antisense-strand does not show full complementary to human ANG2 mRNA (in contrast to siRNA No. 64 and 65). Other siRNA sequences were compared to a previously published siRNA sequence (FIG. 9: Ang2-Bhandari_A+B: 19-mer with 3'-TT-overhangs; Bhandari et al., 2006), For this purpose, the published sequence was synthesized as 19-mer dsRNA including deoxy-TT overhangs and two blunt-ended 23-mer variants thereof by extending the 19-mer sequence complementary to ANG2-mRNA by four additional complementary bases at the 3' and 5'-end, respectively (FIG. 9). The resulting two blunt-ended 23-mers (Ang2-Bhandari_A+B and Ang2-Bhandari_Atu23_A+B; FIG. 9) were chemically stabilized with 2'-O-methyl modification as mentioned, synthesized and tested side by side in a transfections experiment with the siRNA molecule formed by SEQ ID NOs: 48 and 49. The siRNA molecule formed by SEQ ID NOs: 48 and 49 was equal (FIG. 10) if not even more potent than the published sequence (“Bhandari” 19-mer TT) or derivatives thereof (blunt-ended, modified, extended 23-mers: FIG. 9), as revealed by determination of mRNA levels by TaqMan-PCR. Another in vitro screen with additional 8 newly designed 23-mer targeting mouse Ang2 (ANGT2 molecules, FIG. 11) gave surprisingly rise to another more potent siRNA when compared to other 23-mer siRNA including the ANG2 siRNA molecule #9 (see FIGS. 11 and 12). The better potency was underlined in a side-by-side comparison titration experiment (FIG. 12B). From this example it may be taken that different siRNA molecules targeting different regions of the Ang-2 mRNA show different activities in terms of knockdown of the target mRNA.

Example 5

Improved Pulmonary Vascular Barrier Function in PLY- or *S. pneumoniae* Infection Stimulated Lungs Through Intravenous siRNA$^{Ang2}$-Lipoplex Increased microvascular permeability of the lung is a hallmark event during the onset and progression of ALI (Acute Lung Injury) or its more severe form ARDS (Acute respiratory distress syndrome) (Aird, 2003; Ware 2006, Maniatis and Orfanos, 2008). Mice were treated intravenously (low pressure bolus tail vein injection) with a 19-mer siRNA$^{Ang2}$-lipoplex on four consecutive days. For control, siRNA$^{Luc}$-lipoplex and an unrelated siRNA$^{Target2}$-lipoplex were applied in parallel. Pulmonary vascular permeability was measured afterwards in isolated pneumolysin (PLY)-stimulated lungs (ex vivo isolated perfused mouse lungs system, FIG. 4-5). In contrast to control samples, PLY dramatically increased microvascular permeability of HSA. However, in contrast to the control animals treated with siRNA$^{Luc}$ or siRNA$^{target2}$-lipoplex, mean vascular permeability in the lung from siRNA$^{Ang2}$-treated animals was significantly lower, suggesting protection of the vasculature from the PLY insult (FIG. 5). Similar results were obtained in vivo when mice were challenged with Pneumococcus lung infection (=pneumonia: after inhalation of pathogenic *S. pneumoniae*) after Ang2-siRNA-lipoplex treatment (FIG. 5, 6); again in contrast to animals from the control groups, Ang2-lipoplex treatment protected from vascular leakage. This finding was supported in a further experiment, in which the intravenous treatment with siRNA$^{Ang2}$-lipoplex has a protective effect on vascular permeability upon *S. pneumoniae* infection was compared to unrelated siRNA$^{Luc}$/siRNA$^{target2}$-lipoplex control (FIG. 6A). The functionality of the lipoplex in triggering RNAi mediated downregulation of Ang2 expression was confirmed in cell culture before the in vivo experiment was carried out (FIG. 6B). Besides the improved barrier function in lungs from siRNA$^{Ang2}$-lipoplex treated mice, target specific knockdown of Ang2-mRNA expression in the corresponding samples was observed (FIG. 6C). The 3'-extended variant of siRNA molecule #7 (see FIG. 2), namely siRNA molecule #9 (see FIG.

11), showed the same protective effect in another ex vivo IPML experiment as described above (FIG. 8).

Example 6

Characterisation of 19-Mer siRNA and their Corresponding 3'-Extended 23-mer Variants The initial 19-mer lead siRNA molecules siRNA No. 7 and 8 (see also FIG. 2) and their corresponding 3'-extended 23-mer variants were further characterized by titration with a transfection experiment in HUVEC. As indicated in FIG. 15, that—as described above—both 19-mer molecules (perfect match to both mouse and human mRNA) exhibit clear dose-dependent silencing activity in comparison to untreated samples, whereas the corresponding 23-mers 8 as indicated in FIG. 15) show clear differences in potency in the cultured human cells. The 23-mer siRNA No. 9 carrying one mismatch to the human Ang-2 mRNA was more potent that the 23-mer siRNA.

Example 7

Characterization of 23-mer siRNA Molecules Targeting Human mRNA of Ang-2

Another set of 16 23-mer siRNA molecules (AtuRNAi molecule number 11-26) was designed and synthesized (FIG. 16: SEQ ID 73-104), targeting the human mRNA-sequence of Ang-2. The siRNA molecule No. 26 was the human variant of the mouse siRNA molecule No. 9 (SEQ. ID. 68, 69), carrying one mismatch to the mouse siRNA variant. These siRNA were tested for RNAi efficacy by transfection in human endothelial cells (HUVEC) at the indicated conditions (FIG. 17) and Ang2 mRNA levels assessed by qRT-PCR. New human lead siRNAs were identified (No. 13, 19, 21, 23, 24, 25; FIG. 18) and further characterized in an additional transfection experiment and compared with previously identified human and mouse siRNA lead molecules (No. 4—SEQ ID 8, 9), the mouse specific siRNA No. 5—negative control) as well as the variants of the initial leads 19-mer siRNA No. 7, and the mouse and human 23-mer variant thereof. In conclusion the screen of human siRNA revealed novel 23-mer siRNA molecules exhibiting similar mRNA suppression efficacy in the transfection experiment.

Example 8

Expression Levels of the Components for the Tie2-Ang System During Development of Pneumonia in Mice after Infection with *Streptococcus pneumoniae*

As indicated in FIG. 19 A, changes in the expression levels of the components for the Tie2-Ang system were observed during development of pneumonia in mice after infection with *Streptococcus pneumoniae*. In this experiment, bacteria were given by inhalation and progression of pneumonia monitored over 48 h. After each indicated time point a cohort of n=6 animals from infected and non-infected mice were sacrificed and the lung tissue dissected. Total RNA from respective samples was isolated and analyzed by TaqMan PCR in order to determine mRNA levels of Tie2, Ang1, Ang2, and PTEN in corresponding samples. The mean value for the each group was plotted over time, demonstrating a decrease of mRNA levels for Ang1 and Tie2 in infected mice when compared to non-infected mice over time. Surprisingly, the mRNA level for Ang2 rose over time in comparison to non-infected control.

Tie-2 protein levels, for which an antibody is available, decreased over time as shown by Western blot with protein extracts from indicated mice (FIG. 19 B).

REFERENCES

Aird, W. C. 2003. The role of the endothelium in severe sepsis and multiple organ dysfunction syndrome. *Blood.* 101: 3765-77.

Bhandari, V., R. Choo-Wing, C. G. Lee, Z. Zhu, J. H. Nedrelow, G. L. Chupp, X. Zhang, M. A. Matthay, L. B. Ware, R. J. Horner, P. J. Lee, A. Geick, A. R. de Fougerolles, and J. A. Elias. 2006. Hyperoxia causes angiopoietin 2-mediated acute lung injury and necrotic cell death. *Nat Med.* 12:1286-93.

Daly, C., E. Pasnikowski, E. Burova, V. Wong, T. H. Aldrich, J. Griffiths, E. Ioffe, T. J. Daly, J. P. Fandl, N. Papadopoulos, D. M. McDonald, G. Thurston, G. D. Yancopoulos, and J. S. Rudge. 2006. Angiopoietin-2 functions as an autocrine protective factor in stressed endothelial cells. *Proc Natl Acad Sci USA.* 103:15491-6.

Fiedler, U., and H. G. Augustin. 2006. Angiopoietins: a link between angiogenesis and inflammation. *Trends Immunol.* 27:552-8.

Maniatis, N. A., and S. E. Orfanos. 2008. The endothelium in acute lung injury/acute respiratory distress syndrome. *Curr Opin Crit Care.* 14:22-30.

Matute-Bello, G., C. W. Frevert, O. Kajikawa, S. J. Skerrett, R. B. Goodman, D. R. Park, and T. R. Martin. 2001. Septic shock and acute lung injury in rabbits with peritonitis: failure of the neutrophil response to localized infection. *Am J Respir Crit Care Med.* 163:234-43.

Opitz, B., A. Puschel, B. Schmeck, A. C. Hocke, S. Rosseau, S. Hammerschmidt, R. R. Schumann, N. Suttorp, and S. Hippenstiel. 2004. Nucleotide-binding oligomerization domain proteins are innate immune receptors for internalized *Streptococcus pneumoniae. J Biol Chem.* 279:36426-32.

Parikh, S. M., T. Mammoto, A. Schultz, H. T. Yuan, D. Christiani, S. A. Karumanchi, and V. P. Sukhatme. 2006. Excess circulating angiopoietin-2 may contribute to pulmonary vascular leak in sepsis in humans. *PLoS Med.* 3:e46.

Paton, J. C., J. K. Morona, S. Harrer, D. Hansman, and R. Morona. 1993. Immunization of mice with *Salmonella typhimurium* C5 aroA expressing a genetically toxoided derivative of the pneumococcal toxin pneumolysin. *Microb Pathog.* 14:95-102.

Santel, A., M. Aleku, O. Keil, J. Endruschat, V. Esche, B. Durieux, K. Loffler, M. Fechtner, T. Rohl, G. Fisch, S. Dames, W. Arnold, K. Giese, A. Klippel, and J. Kaufmann. 2006a. RNA interference in the mouse vascular endothelium by systemic administration of siRNA-lipoplexes for cancer therapy. *Gene Ther.* 13:1360-70.

Santel, A., M. Aleku, O. Keil, J. Endruschat, V. Esche, G. Fisch, S. Dames, K. Loffler, M. Fechtner, W. Arnold, K. Giese, A. Klippel, and J. Kaufmann. 2006b. A novel siRNA-lipoplex technology for RNA interference in the mouse vascular endothelium. *Gene Ther.* 13:1222-34.

Schmeck, B., J. Zahlten, K. Moog, V. van Laak, S. Huber, A. C. Hocke, B. Opitz, E. Hoffmann, M. Kracht, J. Zerrahn, S. Hammerschmidt, S. Rosseau, N. Suttorp, and S. Hippenstiel. 2004. *Streptococcus pneumoniae*-induced p38 MAPK-dependent phosphorylation of RelA at the interleukin-8 promotor. *J Biol Chem.* 279:53241-7.

Ware, L. B. 2006. Pathophysiology of acute lung injury and the acute respiratory distress syndrome. *Semin Respir Crit Care Med.* 27:337-49.

The features of the present invention disclosed in the specification, the claims, the sequence listing and/or the drawings may both separately and in any combination thereof be material for realizing the invention in various forms thereof.

We claim:

1. A siRNA comprising an antisense strand between 19 and 25 nucleotides in length and a sense strand between 19 and 25 nucleotides in length, wherein one or more alternating nucleotides on the sense and/or antisense strands are modified, wherein said antisense strand and said sense strand have a duplex region length consisting of 16, 17, 18, or 19 nucleotides, wherein the duplex region is perfectly complementary or contains 1, 2, 3, 4, or 5 nucleotides that do not base pair and said siRNA comprises the antisense and sense combination of SEQ ID NOs: 14 and 15.

2. The siRNA of claim 1, wherein said duplex region is 16 nucleotides in length and is perfectly complementary.

3. The siRNA of claim 1, wherein said duplex region is 17 nucleotides in length and is perfectly complementary.

4. The siRNA of claim 1, wherein said duplex region is 18 nucleotides in length and is perfectly complementary.

5. The siRNA of claim 1, wherein said duplex region is 19 nucleotides in length and is perfectly complementary.

6. The siRNA of claim 1, wherein said siRNA:

a) is blunt ended at both ends;

b) has an overhang at one end and a blunt end at the other; or c) has an overhang at both ends.

7. The siRNA of claim 1, wherein said alternating nucleotides on both the sense and antisense strands are modified with an O-methyl group at the 2' position.

8. The siRNA of claim 7, wherein each of the odd numbered nucleotides is modified in the antisense strand and each of the even numbered nucleotides is modified in the sense strand.

9. A lipoplex comprising a siRNA of claim 1 and a liposome.

10. The lipoplex of claim 9, wherein the liposome consists of:

a) about 50 mol % β-arginyl-2,3-diaminopropionic acid-N-palmityl-N-oleyl-amide trihydrochloride;

b) about 48 to 49 mol % 1,2-diphytanoyl-sn-glycero-3-phosphoethanolamine (DPhyPE); and c) about 1 to 2 mol % 1,2-distearoyl-sn-glycero-3-phosphoethanolamine-polyethylen-glycol.

11. A vector comprising a promoter operably linked to a nucleic acid encoding or comprising an antisense strand between 19 and 25 nucleotides in length or a sense strand between 19 and 25 nucleotides in length, said antisense and sense strands comprising SEQ ID NOs: 14 and 15.

12. A cell comprising a vector according to claim 11, provided that if the cell is a human cell, said human cell is an isolated cell.

13. A composition comprising a siRNA of claim 1 and a physiologically acceptable excipient.

14. A method for inhibiting angiopoietin (ANG2) expression in a subject comprising the administration of a composition comprising an siRNA molecule of claim 1 to a subject in an amount effective to inhibit the expression of ANG2.

15. A method for improving pulmonary vascular barrier function in a subject comprising the administration of a therapeutically effective amount of a composition comprising an siRNA molecule of claim 1 to a subject.

16. The siRNA of claim 2, wherein said siRNA:

a) is blunt ended at both ends;

b) has an overhang at one end and a blunt end at the other; or c) has an overhang at both ends.

17. The siRNA of claim 3, wherein said siRNA:

a) is blunt ended at both ends;

b) has an overhang at one end and a blunt end at the other; or c) has an overhang at both ends.

18. The siRNA of claim 4, wherein said siRNA:

a) is blunt ended at both ends;

b) has an overhang at one end and a blunt end at the other; or c) has an overhang at both ends.

19. The siRNA of claim 5, wherein said siRNA:

a) is blunt ended at both ends;

b) has an overhang at one end and a blunt end at the other; or c) has an overhang at both ends.

20. The siRNA of claim 1, wherein said duplex region is 16 nucleotides in length and has 1, 2, 3, 4 or 5 nucleotides that do not base pair.

21. The siRNA of claim 1, wherein said duplex region is 17 nucleotides in length and has 1, 2, 3, 4 or 5 nucleotides that do not base pair.

22. The siRNA of claim 1, wherein said duplex region is 18 nucleotides in length and has 1, 2, 3, 4 or 5 nucleotides that do not base pair.

23. The siRNA of claim 1, wherein said duplex region is 19 nucleotides in length and has 1, 2, 3, 4 or 5 nucleotides that do not base pair.

24. The vector of claim 11, wherein said promoter is pol III, U6, H1 or 7SK.

* * * * *

UNITED STATES PATENT AND TRADEMARK OFFICE

CERTIFICATE OF CORRECTION

PATENT NO. : 8,829,179 B2
APPLICATION NO. : 13/201917
DATED : September 9, 2014
INVENTOR(S) : Ansgar Santel, Jorg Kaufmann and Martin Witzenrath It is certified that error appears in the above-identified patent and that said Letters Patent is hereby corrected as shown below:

In the Specification

Column 15,
Line 34, "consisting of:" should read --consisting of.--.

Column 34,
Line 62, "have aan OH" should read --have an OH--.

Signed and Sealed this
Twenty-first Day of April, 2015

Michelle K. Lee
*Director of the United States Patent and Trademark Office*

SEQUENCE LISTING

<160> NUMBER OF SEQ ID NOS: 110

<210> SEQ ID NO 1
<211> LENGTH: 2269
<212> TYPE: RNA
<213> ORGANISM: Homo sapiens

<400> SEQUENCE: 1
uggguuggug uuuaucuccu cccagccuug agggagggaa caacacugua ggaucugggg 60
agagaggaac aaaggaccgu gaaagcugcu cuguaaaagc ugacacagcc cucccaagug 120
agcaggacug uucuucccac ugcaaucuga caguuuacug caugccugga gagaacacag 180
caguaaaaac cagguuugcu acuggaaaaa gaggaaagag aagacuuuca uugacggacc 240
cagccauggc agcguagcag cccugcguuu cagacggcag cagcucggga cucuggacgu 300
guguuugccc ucaaguuugc uaagcugcug guuuauuacu gaagaaagaa uguggcagau 360
uguuuucuuu acucugagcu gugaucuugu cuuggccgca gccuauaaca acuuucggaa 420
gagcauggac agcauaggaa agaagcaaua ucagguccag caugggucccu gcagcuacac 480 uuuccuccug ccagagaugg acaacugccg cucuuccucc agccccuacg uguccaaugc 540
ugugcagagg gacgcgccgc ucgaauacga ugacucggug cagaggcugc aagugcugga 600
gaacaucaug gaaaacaaca cucaguggcu aaugaagcuu gagaauuaua uccaggacaa 660
caugaagaaa gaaaugguag agauacagca gaaugcagua cagaaccaga cggcugugau 720
gauagaaaua gggacaaacc uguugaacca aacagcugag caaacgcgga aguuaacuga 780
uguggaagcc caaguauuaa aucagaccac gagacuugaa cuucagcucu uggaacacuc 840
ccucucgaca aacaaauugg aaaaacagau uuuggaccag accagugaaa uaaacaaauu 900
gcaagauaag aacaguuucc uagaaaagaa ggugcuagcu auggaagaca agcacaucau 960
ccaacuacag ucaauaaaag aagagaaaga ucagcuacag guguuaguau ccaagcaaaa 1020
uuccaucauu gaagaacuag aaaaaaaaau agugacugcc acggugaaua auucaguucu 1080
ucaaaagcag caacaugauc ucauggagac aguuaauaac uuacugacua ugauguccac 1140
aucaaacuca gcuaaggacc ccacuguugc uaaagaagaa caaaucagcu ucagagacug 1200
ugcugaagua uucaaaucag gacacaccac aaauggcauc uacacguuaa cauucccuaa 1260
uucuacagaa gagaucaagg ccuacuguga cauggaagcu ggaggaggcg gguggacaau 1320
uauucagcga cgugaggaug gcagcguuga uuuucagagg acuuggaaag aauauaaagu 1380
gggauuuggu aacccuucag gagaauauug gcugggaaau gaguuuguuu cgcaacugac 1440
uaaucagcaa cgcuaugugc uuaaaauaca ccuuaaagac ugggaaggga augaggcuua 1500
cucauuguau gaacauuucu aucucucaag ugaagaacuc aauuauagga uucaccuuaa 1560
aggacuuaca gggacagccg gcaaaauaag cagcaucagc caaccaggaa augauuuuag 1620
cacaaaggau ggagacaacg acaaauguau uugcaaaugu ucacaaaugc uaacaggagg 1680
cuggugguuu gaugcaugug guccuuccaa cuugaacgga auguacuauc cacagaggca 1740
gaacacaaau aaguucaacg gcauuaaaug guacuacugg aaaggcucag gcuauucgcu 1800
caaggccaca accaugauga uccgaccagc agauuucuaa acaucccagu ccaccugagg 1860
aacugucucg aacuauuuuc aaagacuuaa gcccagugca cugaaaguca cggcugcgca 1920
cuguguccuc uuccaccaca gagggcgugu gcucggugcu gacgggaccc acaugcucca 1980
gauuagagcc uguaaacuuu aucacuuaaa cuugcaucac uuaacggacc aaagcaagac 2040
ccuaaacauc cauaauugug auuagacaga acaccuaugc aaagaugaac ccgaggcuga 2100
gaaucagacu gacaguuuac agacgcugcu gucacaacca agaauguuau gugcaaguuu 2160
aucaguaaau aacuggaaaa cagaacacuu auguuauaca auacagauca ucuuggaacu 2220
gcauucuucu gagcacuguu uauacacugu guaaauaccc auauguccu 2269

<210> SEQ ID NO 2
<211> LENGTH: 19
<212> TYPE: RNA
<213> ORGANISM: Artificial Sequence
<220> FEATURE:
<223> OTHER INFORMATION: antisense siRNA

<400> SEQUENCE: 2
uuaacuuccg cguuugcuc 19

<210> SEQ ID NO 3
<211> LENGTH: 19
<212> TYPE: RNA
<213> ORGANISM: Artificial sequence
<220> FEATURE:
<223> OTHER INFORMATION: sense siRNA

<400> SEQUENCE: 3
gagcaaacgc ggaaguuaa 19

<210> SEQ ID NO 4
<211> LENGTH: 19
<212> TYPE: RNA
<213> ORGANISM: Artificial sequence
<220> FEATURE:
<223> OTHER INFORMATION: antisense siRNA

<400> SEQUENCE: 4
uacuugggcu uccacauca 19

<210> SEQ ID NO 5
<211> LENGTH: 19
<212> TYPE: RNA
<213> ORGANISM: Artificial sequence
<220> FEATURE:
<223> OTHER INFORMATION: sense siRNA

<400> SEQUENCE: 5
ugauguggaa gcccaagua 19

<210> SEQ ID NO 6
<211> LENGTH: 19
<212> TYPE: RNA
<213> ORGANISM: Artificial sequence
<220> FEATURE:
<223> OTHER INFORMATION: antisense siRNA

<400> SEQUENCE: 6
uuguuuauuu cacuggucu 19

<210> SEQ ID NO 7

<211> LENGTH: 19
<212> TYPE: RNA
<213> ORGANISM: Artificial sequence
<220> FEATURE:
<223> OTHER INFORMATION: sense siRNA

<400> SEQUENCE: 7
agaccaguga aauaaacaa 19

<210> SEQ ID NO 8
<211> LENGTH: 19
<212> TYPE: RNA
<213> ORGANISM: Artificial sequence
<220> FEATURE:
<223> OTHER INFORMATION: antisense siRNA

<400> SEQUENCE: 8
uccaugucac aguaggccu 19

<210> SEQ ID NO 9
<211> LENGTH: 19
<212> TYPE: RNA
<213> ORGANISM: Artificial sequence
<220> FEATURE:
<223> OTHER INFORMATION: sense siRNA

<400> SEQUENCE: 9
aggccuacug ugacaugga 19

<210> SEQ ID NO 10
<211> LENGTH: 19
<212> TYPE: RNA
<213> ORGANISM: Artificial sequence
<220> FEATURE:
<223> OTHER INFORMATION: antisense siRNA

<400> SEQUENCE: 10
ucauacaaug aguaagccu 19

<210> SEQ ID NO 11
<211> LENGTH: 19
<212> TYPE: RNA
<213> ORGANISM: Artificial sequence
<220> FEATURE:
<223> OTHER INFORMATION: sense siRNA

<400> SEQUENCE: 11
aggcuuacuc auuguauga 19

<210> SEQ ID NO 12
<211> LENGTH: 19
<212> TYPE: RNA
<213> ORGANISM: Artificial sequence
<220> FEATURE:
<223> OTHER INFORMATION: antisense siRNA

<400> SEQUENCE: 12
auccuuugug cuaaaauca 19

<210> SEQ ID NO 13
<211> LENGTH: 19
<212> TYPE: RNA
<213> ORGANISM: Artificial sequence
<220> FEATURE:
<223> OTHER INFORMATION: sense siRNA

<400> SEQUENCE: 13
ugauuuuagc acaaaggau 19

<210> SEQ ID NO 14
<211> LENGTH: 19
<212> TYPE: RNA
<213> ORGANISM: Artificial sequence
<220> FEATURE:
<223> OTHER INFORMATION: antisense siRNA

<400> SEQUENCE: 14
aguuggaagg accacaugc 19

<210> SEQ ID NO 15
<211> LENGTH: 19
<212> TYPE: RNA
<213> ORGANISM: Artificial sequence
<220> FEATURE:
<223> OTHER INFORMATION: sense siRNA

<400> SEQUENCE: 15
gcaugugguc cuuccaacu 19

<210> SEQ ID NO 16
<211> LENGTH: 19
<212> TYPE: RNA
<213> ORGANISM: Artificial sequence
<220> FEATURE:
<223> OTHER INFORMATION: antisense siRNA

<400> SEQUENCE: 16
aucaucaugg uuguggccu 19

<210> SEQ ID NO 17
<211> LENGTH: 19
<212> TYPE: RNA
<213> ORGANISM: Artificial sequence
<220> FEATURE:
<223> OTHER INFORMATION: sense siRNA

<400> SEQUENCE: 17
aggccacaac caugaugau 19

<210> SEQ ID NO 18
<211> LENGTH: 19
<212> TYPE: RNA
<213> ORGANISM: Artificial sequence
<220> FEATURE:
<223> OTHER INFORMATION: antisense siRNA

<400> SEQUENCE: 18
uagaaauaga auguuggag 19

<210> SEQ ID NO 19
<211> LENGTH: 19
<212> TYPE: RNA
<213> ORGANISM: Artificial sequence
<220> FEATURE:
<223> OTHER INFORMATION: sense siRNA

<400> SEQUENCE: 19
cuccaacauu cuauuucua 19

<210> SEQ ID NO 20
<211> LENGTH: 19
<212> TYPE: RNA

<213> ORGANISM: Artificial sequence
<220> FEATURE:
<223> OTHER INFORMATION: antisense siRNA

<400> SEQUENCE: 20
ucgagaggga guguuccaa 19

<210> SEQ ID NO 21
<211> LENGTH: 19
<212> TYPE: RNA
<213> ORGANISM: Artificial sequence
<220> FEATURE:
<223> OTHER INFORMATION: sense siRNA

<400> SEQUENCE: 21
uuggaacacu cccucucga 19

<210> SEQ ID NO 22
<211> LENGTH: 19
<212> TYPE: RNA
<213> ORGANISM: Artificial sequence
<220> FEATURE:
<223> OTHER INFORMATION: antisense siRNA

<400> SEQUENCE: 22
aucuuaagca cguagcggu 19

<210> SEQ ID NO 23
<211> LENGTH: 19
<212> TYPE: RNA
<213> ORGANISM: Artificial sequence
<220> FEATURE:
<223> OTHER INFORMATION: sense siRNA

<400> SEQUENCE: 23
accgcuacgu gcuuaagau 19

<210> SEQ ID NO 24
<211> LENGTH: 19
<212> TYPE: RNA
<213> ORGANISM: Artificial sequence
<220> FEATURE:
<223> OTHER INFORMATION: antisense siRNA

<400> SEQUENCE: 24
auuuuaagca cauagcguu 19

<210> SEQ ID NO 25
<211> LENGTH: 19
<212> TYPE: RNA
<213> ORGANISM: Artificial sequence
<220> FEATURE:
<223> OTHER INFORMATION: sense siRNA

<400> SEQUENCE: 25
aacgcuaugu gcuuaaaau 19

<210> SEQ ID NO 26
<211> LENGTH: 23
<212> TYPE: RNA
<213> ORGANISM: Artificial sequence
<220> FEATURE:
<223> OTHER INFORMATION: antisense siRNA

<400> SEQUENCE: 26
auauuuaaca gccaggaaga aaa 23

```
<210> SEQ ID NO 27
<211> LENGTH: 23
<212> TYPE: RNA
<213> ORGANISM: Artificial sequence
<220> FEATURE:
<223> OTHER INFORMATION: sense siRNA

<400> SEQUENCE: 27

uuuucuuccu ggcuguuaaa uau                                              23


<210> SEQ ID NO 28
<211> LENGTH: 23
<212> TYPE: RNA
<213> ORGANISM: Artificial sequence
<220> FEATURE:
<223> OTHER INFORMATION: antisense siRNA

<400> SEQUENCE: 28

auauuuaaca aucaggcaga aaa                                              23


<210> SEQ ID NO 29
<211> LENGTH: 23
<212> TYPE: RNA
<213> ORGANISM: Artificial sequence
<220> FEATURE:
<223> OTHER INFORMATION: sense siRNA

<400> SEQUENCE: 29

uuuucugccu gauuguuaaa uau                                              23


<210> SEQ ID NO 30
<211> LENGTH: 23
<212> TYPE: RNA
<213> ORGANISM: Artificial sequence
<220> FEATURE:
<223> OTHER INFORMATION: antisense siRNA

<400> SEQUENCE: 30

uuauuuacug cugaacuccc acg                                              23


<210> SEQ ID NO 31
<211> LENGTH: 23
<212> TYPE: RNA
<213> ORGANISM: Artificial sequence
<220> FEATURE:
<223> OTHER INFORMATION: sense siRNA

<400> SEQUENCE: 31

cgugggaguu cagcaguaaa uaa                                              23


<210> SEQ ID NO 32
<211> LENGTH: 23
<212> TYPE: RNA
<213> ORGANISM: Artificial sequence
<220> FEATURE:
<223> OTHER INFORMATION: antisense siRNA

<400> SEQUENCE: 32

uuauuuacug auaaacuugc aca                                              23


<210> SEQ ID NO 33
<211> LENGTH: 23
<212> TYPE: RNA
<213> ORGANISM: Artificial sequence
<220> FEATURE:
```

-continued

```
<223> OTHER INFORMATION: sense siRNA

<400> SEQUENCE: 33

ugugcaaguu uaucaguaaa uaa                                              23


<210> SEQ ID NO 34
<211> LENGTH: 23
<212> TYPE: RNA
<213> ORGANISM: Artificial sequence
<220> FEATURE:
<223> OTHER INFORMATION: antisense siRNA

<400> SEQUENCE: 34

auauaguaaa uaguagccag cca                                              23


<210> SEQ ID NO 35
<211> LENGTH: 23
<212> TYPE: RNA
<213> ORGANISM: Artificial sequence
<220> FEATURE:
<223> OTHER INFORMATION: sense siRNA

<400> SEQUENCE: 35

uggcuggcua cuauuuacua uau                                              23


<210> SEQ ID NO 36
<211> LENGTH: 23
<212> TYPE: RNA
<213> ORGANISM: Artificial sequence
<220> FEATURE:
<223> OTHER INFORMATION: antisense siRNA

<400> SEQUENCE: 36

auauaaauuu gaaauacgua uuu                                              23


<210> SEQ ID NO 37
<211> LENGTH: 23
<212> TYPE: RNA
<213> ORGANISM: Artificial sequence
<220> FEATURE:
<223> OTHER INFORMATION: sense siRNA

<400> SEQUENCE: 37

aaauacguau uucaaauuua uau                                              23


<210> SEQ ID NO 38
<211> LENGTH: 23
<212> TYPE: RNA
<213> ORGANISM: Artificial sequence
<220> FEATURE:
<223> OTHER INFORMATION: antisense siRNA

<400> SEQUENCE: 38

uauuuaauua cuaaaaauac cuu                                              23


<210> SEQ ID NO 39
<211> LENGTH: 23
<212> TYPE: RNA
<213> ORGANISM: Artificial sequence
<220> FEATURE:
<223> OTHER INFORMATION: sense siRNA

<400> SEQUENCE: 39

aagguauuuu uaguaauuaa aua                                              23
```

<210> SEQ ID NO 40
<211> LENGTH: 23
<212> TYPE: RNA
<213> ORGANISM: Artificial sequence
<220> FEATURE:
<223> OTHER INFORMATION: antisense siRNA

<400> SEQUENCE: 40
uuucaaauga acauguaaag cac 23

<210> SEQ ID NO 41
<211> LENGTH: 23
<212> TYPE: RNA
<213> ORGANISM: Artificial sequence
<220> FEATURE:
<223> OTHER INFORMATION: sense siRNA

<400> SEQUENCE: 41
gugcuuuaca uguucauuug aaa 23

<210> SEQ ID NO 42
<211> LENGTH: 23
<212> TYPE: RNA
<213> ORGANISM: Artificial sequence
<220> FEATURE:
<223> OTHER INFORMATION: antisense siRNA

<400> SEQUENCE: 42
uuuugaaaua aaaauuuaaa gca 23

<210> SEQ ID NO 43
<211> LENGTH: 23
<212> TYPE: RNA
<213> ORGANISM: Artificial sequence
<220> FEATURE:
<223> OTHER INFORMATION: sense siRNA

<400> SEQUENCE: 43
ugcuuuaaau uuuuauuuca aaa 23

<210> SEQ ID NO 44
<211> LENGTH: 23
<212> TYPE: RNA
<213> ORGANISM: Artificial sequence
<220> FEATURE:
<223> OTHER INFORMATION: antisense siRNA

<400> SEQUENCE: 44
aaaaguuagg aaaaugaucu gcc 23

<210> SEQ ID NO 45
<211> LENGTH: 23
<212> TYPE: RNA
<213> ORGANISM: Artificial sequence
<220> FEATURE:
<223> OTHER INFORMATION: sense siRNA

<400> SEQUENCE: 45
ggcagaucau uuuccuaacu uuu 23

<210> SEQ ID NO 46
<211> LENGTH: 23
<212> TYPE: RNA
<213> ORGANISM: Artificial sequence
<220> FEATURE:
<223> OTHER INFORMATION: antisense siRNA

<400> SEQUENCE: 46
cagaguaaag aaaacaaucu gcc 23

<210> SEQ ID NO 47
<211> LENGTH: 23
<212> TYPE: RNA
<213> ORGANISM: Artificial sequence
<220> FEATURE:
<223> OTHER INFORMATION: sense siRNA

<400> SEQUENCE: 47
ggcagauugu uuucuuuacu cug 23

<210> SEQ ID NO 48
<211> LENGTH: 23
<212> TYPE: RNA
<213> ORGANISM: Artificial sequence
<220> FEATURE:
<223> OTHER INFORMATION: antisense siRNA

<400> SEQUENCE: 48
aucaucaugg uuguggccuu gag 23

<210> SEQ ID NO 49
<211> LENGTH: 23
<212> TYPE: RNA
<213> ORGANISM: Artificial sequence
<220> FEATURE:
<223> OTHER INFORMATION: sense siRNA

<400> SEQUENCE: 49
cucaaggcca caaccaugau gau 23

<210> SEQ ID NO 50
<211> LENGTH: 23
<212> TYPE: RNA
<213> ORGANISM: Artificial sequence
<220> FEATURE:
<223> OTHER INFORMATION: antisense siRNA

<400> SEQUENCE: 50
uucaaguugg aaggaccaca ugc 23

<210> SEQ ID NO 51
<211> LENGTH: 23
<212> TYPE: RNA
<213> ORGANISM: Artificial sequence
<220> FEATURE:
<223> OTHER INFORMATION: sense siRNA

<400> SEQUENCE: 51
gcaugugguc cuuccaacuu gaa 23

<210> SEQ ID NO 52
<211> LENGTH: 23
<212> TYPE: RNA
<213> ORGANISM: Artificial sequence
<220> FEATURE:
<223> OTHER INFORMATION: antisense siRNA

<400> SEQUENCE: 52
auauuuaaca gccaggaaga aaa 23

<210> SEQ ID NO 53
<211> LENGTH: 23

<212> TYPE: RNA
<213> ORGANISM: Artificial sequence
<220> FEATURE:
<223> OTHER INFORMATION: sense siRNA

<400> SEQUENCE: 53
uuuucuuccu ggcuguuaaa uau 23

<210> SEQ ID NO 54
<211> LENGTH: 23
<212> TYPE: RNA
<213> ORGANISM: Artificial sequence
<220> FEATURE:
<223> OTHER INFORMATION: antisense siRNA

<400> SEQUENCE: 54
uuauuuacug cugaacuccc acg 23

<210> SEQ ID NO 55
<211> LENGTH: 23
<212> TYPE: RNA
<213> ORGANISM: Artificial sequence
<220> FEATURE:
<223> OTHER INFORMATION: sense siRNA

<400> SEQUENCE: 55
cgugggaguu cagcaguaaa uaa 23

<210> SEQ ID NO 56
<211> LENGTH: 23
<212> TYPE: RNA
<213> ORGANISM: Artificial sequence
<220> FEATURE:
<223> OTHER INFORMATION: antisense siRNA

<400> SEQUENCE: 56
auauaguaaa uaguagccag cca 23

<210> SEQ ID NO 57
<211> LENGTH: 23
<212> TYPE: RNA
<213> ORGANISM: Artificial sequence
<220> FEATURE:
<223> OTHER INFORMATION: sense siRNA

<400> SEQUENCE: 57
uggcuggcua cuauuuacua uau 23

<210> SEQ ID NO 58
<211> LENGTH: 23
<212> TYPE: RNA
<213> ORGANISM: Artificial sequence
<220> FEATURE:
<223> OTHER INFORMATION: antisense siRNA

<400> SEQUENCE: 58
uauuuaauua cuaaaaauac cuu 23

<210> SEQ ID NO 59
<211> LENGTH: 23
<212> TYPE: RNA
<213> ORGANISM: Artificial sequence
<220> FEATURE:
<223> OTHER INFORMATION: sense siRNA

<400> SEQUENCE: 59
aagguauuuu uaguaauuaa aua 23

<210> SEQ ID NO 60
<211> LENGTH: 23
<212> TYPE: RNA
<213> ORGANISM: Artificial sequence
<220> FEATURE:
<223> OTHER INFORMATION: antisense siRNA

<400> SEQUENCE: 60
uuucaaauga acauguaaag cac 23

<210> SEQ ID NO 61
<211> LENGTH: 23
<212> TYPE: RNA
<213> ORGANISM: Artificial sequence
<220> FEATURE:
<223> OTHER INFORMATION: sense siRNA

<400> SEQUENCE: 61
gugcuuuaca uguucauuug aaa 23

<210> SEQ ID NO 62
<211> LENGTH: 23
<212> TYPE: RNA
<213> ORGANISM: Artificial sequence
<220> FEATURE:
<223> OTHER INFORMATION: antisense siRNA

<400> SEQUENCE: 62
aaaaguuagg aaaaugaucu gcc 23

<210> SEQ ID NO 63
<211> LENGTH: 23
<212> TYPE: RNA
<213> ORGANISM: Artificial sequence
<220> FEATURE:
<223> OTHER INFORMATION: sense siRNA

<400> SEQUENCE: 63
ggcagaucau uuuccuaacu uuu 23

<210> SEQ ID NO 64
<211> LENGTH: 23
<212> TYPE: RNA
<213> ORGANISM: Artificial sequence
<220> FEATURE:
<223> OTHER INFORMATION: antisense siRNA

<400> SEQUENCE: 64
aucaucaugg uuguggccuu gag 23

<210> SEQ ID NO 65
<211> LENGTH: 23
<212> TYPE: RNA
<213> ORGANISM: Artificial sequence
<220> FEATURE:
<223> OTHER INFORMATION: sense siRNA

<400> SEQUENCE: 65
cucaaggcca caaccaugau gau 23

<210> SEQ ID NO 66
<211> LENGTH: 23
<212> TYPE: RNA
<213> ORGANISM: Artificial sequence
<220> FEATURE:
<223> OTHER INFORMATION: antisense siRNA

<400> SEQUENCE: 66
uucaaguugg aaggaccaca ugc 23

<210> SEQ ID NO 67
<211> LENGTH: 23
<212> TYPE: RNA
<213> ORGANISM: Artificial sequence
<220> FEATURE:
<223> OTHER INFORMATION: sense siRNA

<400> SEQUENCE: 67
gcaugugguc cuuccaacuu gaa 23

<210> SEQ ID NO 68
<211> LENGTH: 23
<212> TYPE: RNA
<213> ORGANISM: Artificial sequence
<220> FEATURE:
<223> OTHER INFORMATION: antisense siRNA

<400> SEQUENCE: 68
aguuggaagg accacaugcg uca 23

<210> SEQ ID NO 69
<211> LENGTH: 23
<212> TYPE: RNA
<213> ORGANISM: Artificial sequence
<220> FEATURE:
<223> OTHER INFORMATION: sense siRNA

<400> SEQUENCE: 69
ugacgcaugu gguccuucca acu 23

<210> SEQ ID NO 70
<211> LENGTH: 2475
<212> TYPE: RNA
<213> ORGANISM: Mus musculus

<400> SEQUENCE: 70
gauacugaca cuguagacuc aggggagaaa caaagagucc gugcagaccu cuggagugag 60
cagggcugcu ccuuccucuc aggacagcuc cgagugugcc ggggagaaga gaagagaaga 120
gacaggcacu gggaaagagc cugcugcggg acggagaagg cucucacuga uggacuuauu 180
cacacggcac agcccugugc cuuagacagc agcugagagc ucaggacgca aguuugcuga 240
acucacaguu uagaacccaa aaagagagag agaauguggc agaucauuuu ccuaacuuuu 300
ggcugggauc uugucuuggc cucagccuac aguaacuuua ggaagagcgu ggacagcaca 360
ggcagaaggc aguaccaggu ccagaacgga cccugcagcu acacguuccu gcugccggag 420
accgacagcu gccgaucuuc cuccagcccc uacaugucca augccgugca gagggaugca 480
ccccucgacu acgacgacuc agugcaaagg cugcaggugc uggagaacau ucuagagaac 540
aacacacagu ggcugaugaa gcuggagaau uacauucagg acaacaugaa gaaggagaug 600
guggagaucc aacagaaugu ggugcagaac cagacagcug ugaugauaga gauuggaacc 660
agcuugcuga accagacagc agcacaaacu cggaaacuga cugaugugga agcccaagua 720
cuaaaccaga cgacaagacu cgagcugcag cuucuccaac auucuauuuc uaccaacaaa 780
uuggaaaagc agauuuugga ucagaccagu gaaauaaaca agcuacaaaa uaagaacagc 840

```
uuccuagaac agaaaguucu ggacauggag ggcaagcaca gcgagcagcu acaguccaug    900

aaggagcaga aggacgagcu ccaggugcug guguccaagc agagcucugu cauugacgag    960

cuggagaaga agcuggugac agccacgguc aacaacucgc uccuucagaa gcagcagcau   1020

gaccuaaugg agaccgucaa cagcuugcug accaugaugu caucacccaa cuccaagagc   1080

ucgguugcua uccguaaaga agagcaaacc accuucagag acugugcgga aaucuucaag   1140

ucaggacuca ccaccagugg caucuacaca cugaccuucc ccaacuccac agaggagauc   1200

aaggccuacu gugacaugga cgugggugga ggagggugga cagucaucca acaccgagaa   1260

gauggcagug uggacuucca gaggacgugg aaagaauaca aagagggcuu cgggagcccu   1320

cugggagagu acuggcuggg caaugaguuu gucucccagc ugaccggucc gcaccgcuac   1380

gugcuuaaga uccagcugaa ggacugggaa ggcaacgagg cgcauucgcu guaugaucac   1440

uucuaccucg cuggugaaga guccaacuac aggauucacc uuacaggacu cacggggacc   1500

gcgggcaaaa uaaguagcau cagccaacca ggaagugauu uuagcacaaa ggauucggac   1560

aaugacaaau gcaucugcaa guguucccag augcucucag gaggcuggug guuugacgca   1620

ugugguccuu ccaacuugaa uggacaguac uacccacaaa aacagaauac aaauaaguuu   1680

aacgguauca aguggguacua cuggaagggg uccggcuacu cgcucaaggc cacaaccaug   1740

augauccggc cagcagauuu cuaaaugccu gccuacacua ccagaagaac uugcugcauc   1800

caaagauuaa cuccaaggca cugagagaca ccaaugcaua gcagccccuu uccacaucag   1860

gaagugcucc ugggggguggg gagggucugu guguaccaga cugaagcgca ucacuuaagc   1920

cugcaccgcu aaccaaccaa aggcacugca gucuggagaa acacuucugg gaagguugug   1980

gcugaggauc agaaggacag cgugcagacu cugucacagg gaagaauguu ccgugggagu   2040

ucagcaguaa auaacuggaa aacagaacac uuagauggug cagauaaauc uugggaccac   2100

auuccucuaa gcacgguuuc uagagugaau acauucacag cucggcuguc acaaugacaa   2160

ggccgugucc ucgcacugug gcagccagua uccagggacu ucuaagugguu gggcacaggu   2220

uaucaucugg agaagcacac auucauuguu uuccucuugg gugcuuuaca uguucauuug   2280

aaaacaacac auuuaccuau cuugauggcu uaguuuuuaa uggcuggcua cuauuuacua   2340

uauggcaaaa augcccacau cucuggaaua accaccaaau aagcgccaug uuggugaaug   2400

cggagacugu acuauuuugu uuucuuccug gcuguuaaau augaagguau uuuuaguaau   2460

uaaauauaag uuauu                                                    2475
```

<210> SEQ ID NO 71
<211> LENGTH: 5267
<212> TYPE: RNA
<213> ORGANISM: Homo sapiens

<400> SEQUENCE: 71

```
aaagugauug auucggauac ugacacugua ggaucugggg agagaggaac aaaggaccgu     60

gaaagcugcu cuguaaaagc ugacacagcc cucccaagug agcaggacug uucuucccac    120

ugcaaucuga caguuuacug caugccugga gagaacacag caguaaaaac cagguuugcu    180

acuggaaaaa gaggaaagag aagacuuuca uugacggacc cagccauggc agcguagcag    240

cccugcguuu uagacggcag cagcucggga cucuggacgu guguuugccc ucaaguuugc    300

uaagcugcug guuuauuacu gaagaaagaa uguggcagau uguuuucuuu acucugagcu    360

gugaucuugu cuuggccgca gccuauaaca acuuucggaa gagcauggac agcauaggaa    420

agaagcaaua ucagguccag caugggucuu gcagcuacac uuuccuccug ccagagaugg    480
```

```
acaacugccg cucuuccucc agccccuacg uguccaaugc ugugcagagg gacgcgccgc    540
ucgaauacga ugacucggug cagaggcugc aagugcugga gaacaucaug gaaaacaaca    600
cucaguggcu aaugaagcuu gagaauuaua uccaggacaa caugaagaaa gaaaugguag    660
agauacagca gaaugcagua cagaaccaga cggcugugau gauagaaaua gggacaaacc    720
uguugaacca aacagcggag caaacgcgga aguuaacuga uguggaagcc caaguauuaa    780
aucagaccac gagacuugaa cuucagcucu uggaacacuc ccucucgaca aacaaauugg    840
aaaaacagau uuuggaccag accagugaaa uaaacaaauu gcaagauaag aacaguuucc    900
uagaaaagaa ggugcuagcu auggaagaca agcacaucau ccaacuacag ucaauaaaag    960
aagagaaaga ucagcuacag guguuaguau ccaagcaaaa uuccaucauu gaagaacuag   1020
aaaaaaaaau agugacugcc acggugaaua auucaguucu ucagaagcag caacaugauc   1080
ucauggagac aguuaauaac uuacugacua ugauguccac aucaaacucu aaggacccca   1140
cuguugcuaa agaagaacaa aucagcuuca gagacugugc ugaaguauuc aaaucaggac   1200
acaccacgaa uggcaucuac acguuaacau ucccuaauuc uacagaagag aucaaggccu   1260
acugugacau ggaagcugga ggaggcgggu ggacaauuau ucagcgacgu gaggauggca   1320
gcguugauuu ucagaggacu uggaaagaau auaaaguggg auuugguaac ccuucaggag   1380
aauauuggcu gggaaaugag uuuguuucgc aacugacuaa ucagcaacgc uaugugcuua   1440
aaauacaccu uaaagacugg gaagggaaug aggcuuacuc auuguaugaa cauuucuauc   1500
ucucaaguga agaacucaau uauaggauuc accuuaaagg acuuacaggg acagccggca   1560
aaauaagcag caucagccaa ccaggaaaug auuuuagcac aaaggaugga gacaacgaca   1620
aauguauuug caaauguuca caaaugcuaa caggaggcug gugguuugau gcaugugguc   1680
cuuccaacuu gaacggaaug uacuauccac agaggcagaa cacaaauaag uucaacggca   1740
uuaaauggua cuacuggaaa ggcucaggcu auucgcucaa ggccacaacc augaugaucc   1800
gaccagcaga uuucuaaaca ucccagucca ccugaggaac ugucucgaac uauuuucaaa   1860
gacuuaagcc cagugcacug aaagucacgg cugcgcacug uguccucuuc caccacagag   1920
ggcgugugcu cggugcugac gggacccaca ugcuccagau uagagccugu aaacuuuauc   1980
acuuaaacuu gcaucacuua acggaccaaa gcaagacccu aaacauccau aauugugauu   2040
agacagaaca ccuaugcaaa gaugaacccg aggcugagaa ucagacugac aguuuacaga   2100
cgcugcuguc acaaccaaga auguuaugug caaguuuauc aguaaauaac uggaaaacag   2160
aacacuuaug uuauacaaua cagaucaucu uggaacugca uucuucugag cacuguuuau   2220
acacugugua aauacccaua uguccugaau ucaccaucac uaucacaauu aaaaggaaga   2280
aaaaaacucu cuaagccaua aaaagacaua uucagggaua uucugagaag ggguuacuag   2340
aaguuuaaua uuuggaaaaa caguuagugc auuuuuacuc caucucuuag gugcuuuaaa   2400
uuuuuauuuc aaaaacagcg uauuuacauu uauguugaca gcuuaguuau aaguuaaugc   2460
ucaaauacgu auuucaaauu uauaugguag aaacuuccag aaucucugaa auuaucaaca   2520
gaaacgugcc auuuuaguuu auaugcagac cguacuauuu uuuucugccu gauuguuaaa   2580
uaugaaggua uuuuuaguaa uuaaauauaa cuuauuaggg gauaugccua uguuuaacuu   2640
uuaugauaau auuuacaauu uuauaauuug uuuccaaaag accuaauugu gccuugugau   2700
aaggaaacuu cuuacuuuua augaugagga aaauuauaca uuucauucua ugacaaagaa   2760
acuuuacuau cuucucacua uucuaaaaca gagguucuguu uucuuuccua guaagauaua   2820
```

-continued

```
uuuuuauaga acuagacuac aauuuaauuu cugguugaga aaagccuucu auuuaagaaa   2880
uuuacaaagc uauaugucuc aagauucacc cuuaaauuua cuuaaggaaa aaaauaauug   2940
acacuaguaa guuuuuuuau gucaaucagc aaacugaaaa aaaaaaaagg guuucaaagu   3000
gcaaaaacaa aaucugaugu ucauaauaua uuuaaauauu uaccaaaaau uugagaacac   3060
agggcugggc gcaguggcuc acaccuauaa ucccaguaca uugguaggca aggugggcag   3120
aucaccugag gucaggaguu caagaccagc cuggacaaca uggugaaacc cugucucuac   3180
uaaauaauac aaaaauuagc caggcgugcu ggcgggcacc uguaauccca gcuacucggg   3240
aggcugaggc agggagaauu gcuugcacca gggagguaga gguugcagug agccaagauc   3300
gcaccacugc acuccagccg gggcaacaga gcaagacucc aucucaaaaa aaaaaaaaaa   3360
aaaagaaaga aaagaaaauu ugagaacaca gcuuuauacu cgggacuaca aaaccauaaa   3420
cuccuggagu uuuaacuccu uuugaaauuu ucauaguaca auuaauacua augaacauuu   3480
guguaaagcu uuauaauuua aaggcaauuu cucauauauu cuuuucugaa ucauuugcaa   3540
ggaaguucag aguccagucu guaacuagca ucuacuauau gucugucuuc accuuacagu   3600
guucuaccau uauuuuuucu uuauuccauu ucaaaaucua auuuauuuua ccccaacuuc   3660
uccccaccac uugacguagu uuuagaacac acagguguug cuacauauuu ggagucaaug   3720
auggacucug gcaaagucaa ggcucuguuu uauuuccacc aaggugcacu uuuccaacaa   3780
cuauuuaacu aguuaagaac cucccuaucu uagaacugua ucuacuuuau auuuaagaag   3840
guuuuaugaa uucaacaacg guaucauggc cuuguaucaa guugaaaaac aacugaaaau   3900
aagaaaauuu cacagccucg aaagacaaca acaaguuucu aggauaucuc aaugacaaga   3960
gugauggaua cuuagguagg gaaacgcuaa ugcaggaaaa acuggcaaca acacaauuua   4020
uaucaauucu cuuuguaggc aggugauaaa aaauucaagg acaaaucuca uuaugucauu   4080
gugcaucaua uauaaucucu uaugagcgag aaugggggga auuuguguuu uuacuuuaca   4140
cuucaauucc uuacacggua uuucaaacaa acaguuuugc ugagaggagc uuuugucucu   4200
ccuuaagaaa auguuuauaa agcugaaagg aaaucaaaca guaaucuuaa aaaugaaaac   4260
aaaacaaccc aacaaccuag auaacuacag ugaucaggga gcacaguuca acuccuuguu   4320
auguuuuagu cauauggccu acucaaacag cuaaauaaca acaccagugg cagauaaaaa   4380
ucaccauuua ucuuucagcu auuaaucuuu ugaaugaaua aacugugaca aacaaauuaa   4440
cauuuuugaa caugaaaggc aacuucugca caauccugua uccaagcaaa cuuuaaauua   4500
uccacuuaau uauuacuuaa ucuuaaaaaa aauuagaacc cagaacuuuu caaugaagca   4560
uuugaaaguu gaaguggaau uuaggaaagc cauaaaaaua uaaauacugu uaucacagca   4620
ccagcaagcc auaaucuuua uaccuaucag uucuauuucu auuaacagua aaaacauuaa   4680
gcaagauaua agacuaccug cccaagaauu cagucuuuuu ucauuuuugu uuuucucagu   4740
ucugaggaug uuaaucguca aauuuucuuu ggacugcauu ccucacuacu uuuugcacaa   4800
uggucucacg uucucacauu uguucucgcg aauaaauuga uaaaaggugu uaaguucugu   4860
gaaugucuuu uuaauuaugg gcauaauugu gcuugacugg auaaaaacuu aaguccaccc   4920
uuauguuuau aauaauuucu ugagaacagc aaacugcauu uaccaucgua aaacaacauc   4980
ugacuuacgg gagcugcagg gaagugguga gacaguucga acggcuccuc agaaauccag   5040
ugacccaauu cuaaagacca uagcaccugc aagugacaca acaagcagau uuauuauaca   5100
uuuauuagcc uuagcaggca auaaaccaag aaucacuuug aagacacagc aaaaagugau   5160
acacuccgca gaucugaaau agauguguuc ucagacaaca aagucccuuc agaaucuuca   5220
```

```
uguugcauaa auguuaugaa uauuaauaaa aaguugauug agaaaaa                5267


<210> SEQ ID NO 72
<211> LENGTH: 5114
<212> TYPE: RNA
<213> ORGANISM: Homo sapiens

<400> SEQUENCE: 72

aaagugauug auucggauac ugacacugua ggaucugggg agagaggaac aaaggaccgu     60

gaaagcugcu cuguaaaagc ugacacagcc cucccaagug agcaggacug uucuucccac    120

ugcaaucuga caguuuacug caugccugga gagaacacag caguaaaaac cagguuugcu    180

acuggaaaaa gaggaaagag aagacuuuca uugacggacc cagccauggc agcguagcag    240

cccugcguuu uagacggcag cagcucggga cucuggacgu guguuugccc ucaaguuugc    300

uaagcugcug guuuauuacu gaagaaagaa uguggcagau uguuuucuuu acucugagcu    360

gugaucuugu cuuggccgca gccuauaaca acuuucggaa gagcauggac agcauaggaa    420

agaagcaaua ucagguccag cauggguccu gcagcuacac uuuccuccug ccagagaugg    480

acaacugccg cucuuccucc agccccuacg uguccaaugc ugugcagagg gacgcgccgc    540

ucgaauacga ugacucggug cagaggcugc aagugcugga gaacaucaug gaaaacaaca    600

cucaguggcu aaugaaggua uuaaaucaga ccacgagacu ugaacuucag cucuuggaac    660

acucccucuc gacaaacaaa uuggaaaaac agauuuugga ccagaccagu gaaauaaaca    720

aauugcaaga uaagaacagu uuccuagaaa agaaggugcu agcuauggaa gacaagcaca    780

ucauccaacu acagucaaua aaagaagaga aagaucagcu acaggugua guauccaagc     840

aaaauuccau cauugaagaa cuagaaaaaa aaauagugac ugccacggug aauaauucag    900

uucuucagaa gcagcaacau gaucucaugg agacaguuaa uaacuuacug acuaugaugu    960

ccacaucaaa cucagcuaag gaccccacug uugcuaaaga agaacaaauc agcuucagag   1020

acugugcuga aguauucaaa ucaggacaca ccacgaaugg caucuacacg uuaacauucc   1080

cuaauucuac agaagagauc aaggccuacu gugacaugga agcuggagga ggcgggugga   1140

caauuauuca gcgacgugag gauggcagcg uugauuuuca gaggacuugg aaagaauaua   1200

aagugggauu ugguaacccu ucaggagaau auuggcuggg aaaugaguuu guuucgcaac   1260

ugacuaauca gcaacgcuau gugcuuaaaa uacaccuuaa agacugggaa gggaaugagg   1320

cuuacucauu guaugaacau uucuaucucu caagugaaga acucaauuau aggauucacc   1380

uuaaaggacu uacagggaca gccggcaaaa uaagcagcau cagccaacca ggaaaugauu   1440

uuagcacaaa ggauggagac aacgacaaau guauuugcaa auguucacaa augcuaacag   1500

gaggcuggug guuugaugca ugugguccuu ccaacuugaa cggaauguac uauccacaga   1560

ggcagaacac aaauaaguuc aacggcauua aaugguacua cuggaaaggc ucaggcuauu   1620

cgcucaaggc cacaaccaug augauccgac cagcagauuu cuaaacaucc caguccaccu   1680

gaggaacugu cucgaacuau uuucaaagac uuaagcccag ugcacugaaa gucacggcug   1740

cgcacugugu ccucuuccac cacagagggc gugugcucgg ugcugacggg acccacaugc   1800

uccagauuag agccuguaaa cuuuaucacu uaaacuugca ucacuuaacg gaccaaagca   1860

agacccuaaa cauccauaau ugugauuaga cagaacaccu augcaaagau gaacccgagg   1920

cugagaauca gacugacagu uuacagacgc ugcugucaca accaagaaug uuaugugcaa   1980

guuuaucagu aaauaacugg aaaacagaac acuuauguua uacaauacag aucaucuugg   2040
```

```
aacugcauuc uucugagcac uguuuauaca cuguguaaau acccauaugu ccugaauuca   2100
ccaucacuau cacaauuaaa aggaagaaaa aaacucucua agccauaaaa agacauauuc   2160
agggauauuc ugagaagggg uuacuagaag uuuaauauuu ggaaaaacag uuagugcauu   2220
uuuacuccau cucuuaggug cuuuaaauuu uuauuucaaa aacagcguau uuacauuuau   2280
guugacagcu uaguuauaag uuaaugcuca aauacguauu ucaaauuuau augguagaaa   2340
cuuccagaau cucugaaauu aucaacagaa acgugccauu uuaguuuaua ugcagaccgu   2400
acuauuuuuu ucugccugau uguuaaauau gaagguauuu uuaguaauua aauauaacuu   2460
auuaggggau augccuaugu uuaacuuuua ugauaaauau uacaauuuua uaauuuguuu   2520
ccaaaagacc uaauugugcc uugugauaag gaaacuucuu acuuuuaaug augaggaaaa   2580
uuauacauuu cauucuauga caaagaaacu uuacuaucuu cucacuauuc uaaaacagag   2640
gucuguuuuc uuuccuagua agauauauuu uuauagaacu agacuacaau uuaauuucug   2700
guugagaaaa gccuucuauu uaagaaauuu acaaagcuau augucucaag auucacccuu   2760
aaauuuacuu aaggaaaaaa auaauugaca cuaguaaguu uuuuuauguc aaucagcaaa   2820
cugaaaaaaa aaaaaggguu ucaaagugca aaaacaaaau cugauguuca uaauauauuu   2880
aaauauuuac caaaaauuug agaacacagg gcugggcgca guggcucaca ccuauaaucc   2940
caguacauug guaggcaagg ugggcagauc accugagguc aggaguucaa gaccagccug   3000
gacaacaugg ugaaacccug ucucuacuaa auaauacaaa aauuagccag gcgugcuggc   3060
gggcaccugu aaucccagcu acucgggagg cugaggcagg gagaauugcu ugcaccaggg   3120
agguagaggu ugcagugagc caagaucgca ccacugcacu ccagccgggg caacagagca   3180
agacuccauc ucaaaaaaaa aaaaaaaaaa agaaagaaaa gaaaauuuga gaacacagcu   3240
uuauacucgg gacuacaaaa ccauaaacuc cuggaguuuu aacuccuuuu gaaauuuuca   3300
uaguacaauu aauacuaaug aacauuugug uaaagcuuua uaauuuaaag gcaauuucuc   3360
auauauucuu uucugaauca uuugcaagga aguucagagu ccagucugua acuagcaucu   3420
acuauauguc ugucuucacc uuacaguguu cuaccauuau uuuuucuuua uuccauuuca   3480
aaaucuaauu uauuuuaccc caacuucucc ccaccacuug acguaguuuu agaacacaca   3540
gguguugcua cauauuugga gucaaugaug gacucuggca aagucaaggc ucuguuuuau   3600
uuccaccaag gugcacuuuu ccaacaacua uuuaacuagu uaagaaccuc ccuaucuuag   3660
aacuguaucu acuuuauauu uaagaagguu uuaugaauuc aacaacggua ucauggccuu   3720
guaucaaguu gaaaaacaac ugaaaauaag aaaauuucac agccucgaaa gacaacaaca   3780
aguuucuagg auaucucaau gacaagagug auggauacuu agguagggaa acgcuaaugc   3840
aggaaaaacu ggcaacaaca caauuuauau caauucucuu uguaggcagg ugauaaaaaa   3900
uucaaggaca aaucucauua ugucauugug caucauauau aaucucuuau gagcgagaau   3960
ggggggaauu uguguuuuua cuuuacacuu caauuccuua cacgguauuu caaacaaaca   4020
guuuugcuga gaggagcuuu ugucucuccu uaagaaaaug uuuauaaagc ugaaaggaaa   4080
ucaaacagua aucuuaaaaa ugaaaacaaa acaacccaac aaccuagaua acuacaguga   4140
ucagggagca caguucaacu ccuuguuaug uuuuagucau auggccuacu caaacagcua   4200
aauaacaaca ccaguggcag auaaaaauca ccauuuaucu uucagcuauu aaucuuuuga   4260
augaauaaac ugugacaaac aaauuaacau uuuugaacau gaaaggcaac uucugcacaa   4320
uccuguaucc aagcaaacuu uaaauuaucc acuuaauuau uacuuaaucu uaaaaaaaau   4380
uagaacccag aacuuuucaa ugaagcauuu gaaaguugaa guggaauuua ggaaagccau   4440
```

```
aaaaauauaa auacuguuau cacagcacca gcaagccaua aucuuuauac cuaucaguuc   4500

uauuucuauu aacaguaaaa acauuaagca agauauaaga cuaccugccc aagaauucag   4560

ucuuuuuuca uuuuuguuuu ucucaguucu gaggauguua aucgucaaau uuucuuugga   4620

cugcauuccu cacuacuuuu ugcacaaugg ucucacguuc ucacauuugu ucucgcgaau   4680

aaauugauaa aagguguuaa guucugugaa ugucuuuuua auuaugggca uaauugugcu   4740

ugacuggaua aaaacuuaag uccacccuua uguuuauaau aauuucuuga gaacagcaaa   4800

cugcauuuac caucguaaaa caacaucuga cuuacgggag cugcagggaa guggugagac   4860

aguucgaacg gcuccucaga aauccaguga cccaauucua aagaccauag caccugcaag   4920

ugacacaaca agcagauuua uuauacauuu auuagccuua gcaggcaaua aaccaagaau   4980

cacuuugaag acacagcaaa aagugauaca cuccgcagau cugaaauaga uguguucuca   5040

gacaacaaag ucccuucaga aucuucaugu ugcauaaaug uuaugaauau uaauaaaaag   5100

uugauugaga aaaa                                                      5114
```

<210> SEQ ID NO 73
<211> LENGTH: 23
<212> TYPE: RNA
<213> ORGANISM: Artificial sequence
<220> FEATURE:
<223> OTHER INFORMATION: sense siRNA

<400> SEQUENCE: 73
ccccuacgug uccaaugcug ugc 23

<210> SEQ ID NO 74
<211> LENGTH: 23
<212> TYPE: RNA
<213> ORGANISM: Artificial sequence
<220> FEATURE:
<223> OTHER INFORMATION: antisense siRNA

<400> SEQUENCE: 74
gcacagcauu ggacacguag ggg 23

<210> SEQ ID NO 75
<211> LENGTH: 23
<212> TYPE: RNA
<213> ORGANISM: Artificial sequence
<220> FEATURE:
<223> OTHER INFORMATION: sense siRNA

<400> SEQUENCE: 75
ggaacacucc cucucgacaa aca 23

<210> SEQ ID NO 76
<211> LENGTH: 23
<212> TYPE: RNA
<213> ORGANISM: Artificial sequence
<220> FEATURE:
<223> OTHER INFORMATION: antisense siRNA

<400> SEQUENCE: 76
uguuugucga gagggagugu ucc 23

<210> SEQ ID NO 77
<211> LENGTH: 23
<212> TYPE: RNA
<213> ORGANISM: Artificial sequence
<220> FEATURE:

<223> OTHER INFORMATION: sense siRNA

<400> SEQUENCE: 77
ccagaccagu gaaauaaaca aau 23

<210> SEQ ID NO 78
<211> LENGTH: 23
<212> TYPE: RNA
<213> ORGANISM: Artificial sequence
<220> FEATURE:
<223> OTHER INFORMATION: antisense siRNA

<400> SEQUENCE: 78
auuuguuuau uucacugguc ugg 23

<210> SEQ ID NO 79
<211> LENGTH: 23
<212> TYPE: RNA
<213> ORGANISM: Artificial sequence
<220> FEATURE:
<223> OTHER INFORMATION: sense siRNA

<400> SEQUENCE: 79
ccaucauuga agaacuagaa aaa 23

<210> SEQ ID NO 80
<211> LENGTH: 23
<212> TYPE: RNA
<213> ORGANISM: Artificial sequence
<220> FEATURE:
<223> OTHER INFORMATION: antisense siRNA

<400> SEQUENCE: 80
uuuuucuagu ucuucaauga ugg 23

<210> SEQ ID NO 81
<211> LENGTH: 23
<212> TYPE: RNA
<213> ORGANISM: Artificial sequence
<220> FEATURE:
<223> OTHER INFORMATION: sense siRNA

<400> SEQUENCE: 81
ggagacaguu aauaacuuac uga 23

<210> SEQ ID NO 82
<211> LENGTH: 23
<212> TYPE: RNA
<213> ORGANISM: Artificial sequence
<220> FEATURE:
<223> OTHER INFORMATION: antisense siRNA

<400> SEQUENCE: 82
ucaguaaguu auuaacuguc ucc 23

<210> SEQ ID NO 83
<211> LENGTH: 23
<212> TYPE: RNA
<213> ORGANISM: Artificial sequence
<220> FEATURE:
<223> OTHER INFORMATION: sense siRNA

<400> SEQUENCE: 83
agacugugcu gaaguauuca aau 23

```
<210> SEQ ID NO 84
<211> LENGTH: 23
<212> TYPE: RNA
<213> ORGANISM: Artificial sequence
<220> FEATURE:
<223> OTHER INFORMATION: antisense siRNA

<400> SEQUENCE: 84

auuugaauac uucagcacag ucu                                              23


<210> SEQ ID NO 85
<211> LENGTH: 23
<212> TYPE: RNA
<213> ORGANISM: Artificial sequence
<220> FEATURE:
<223> OTHER INFORMATION: sense siRNA

<400> SEQUENCE: 85

acaccacgaa uggcaucuac acg                                              23


<210> SEQ ID NO 86
<211> LENGTH: 23
<212> TYPE: RNA
<213> ORGANISM: Artificial sequence
<220> FEATURE:
<223> OTHER INFORMATION: antisense siRNA

<400> SEQUENCE: 86

cguguagaug ccauucgugg ugu                                              23


<210> SEQ ID NO 87
<211> LENGTH: 23
<212> TYPE: RNA
<213> ORGANISM: Artificial sequence
<220> FEATURE:
<223> OTHER INFORMATION: sense siRNA

<400> SEQUENCE: 87

cacguuaaca uucccuaauu cua                                              23


<210> SEQ ID NO 88
<211> LENGTH: 23
<212> TYPE: RNA
<213> ORGANISM: Artificial sequence
<220> FEATURE:
<223> OTHER INFORMATION: antisense siRNA

<400> SEQUENCE: 88

uagaauuagg gaauguuaac gug                                              23


<210> SEQ ID NO 89
<211> LENGTH: 23
<212> TYPE: RNA
<213> ORGANISM: Artificial sequence
<220> FEATURE:
<223> OTHER INFORMATION: sense siRNA

<400> SEQUENCE: 89

aggacuugga aagaauauaa agu                                              23


<210> SEQ ID NO 90
<211> LENGTH: 23
<212> TYPE: RNA
<213> ORGANISM: Artificial sequence
<220> FEATURE:
<223> OTHER INFORMATION: antisense siRNA
```

<400> SEQUENCE: 90
acuuuauauu cuuuccaagu ccu 23

<210> SEQ ID NO 91
<211> LENGTH: 23
<212> TYPE: RNA
<213> ORGANISM: Artificial sequence
<220> FEATURE:
<223> OTHER INFORMATION: sense siRNA

<400> SEQUENCE: 91
aaaauacacc uuaaagacug gga 23

<210> SEQ ID NO 92
<211> LENGTH: 23
<212> TYPE: RNA
<213> ORGANISM: Artificial sequence
<220> FEATURE:
<223> OTHER INFORMATION: antisense siRNA

<400> SEQUENCE: 92
ucccagucuu uaagguguau uuu 23

<210> SEQ ID NO 93
<211> LENGTH: 23
<212> TYPE: RNA
<213> ORGANISM: Artificial sequence
<220> FEATURE:
<223> OTHER INFORMATION: sense siRNA

<400> SEQUENCE: 93
ggaagggaau gaggcuuacu cau 23

<210> SEQ ID NO 94
<211> LENGTH: 23
<212> TYPE: RNA
<213> ORGANISM: Artificial sequence
<220> FEATURE:
<223> OTHER INFORMATION: antisense siRNA

<400> SEQUENCE: 94
augaguaagc cucauucccu ucc 23

<210> SEQ ID NO 95
<211> LENGTH: 23
<212> TYPE: RNA
<213> ORGANISM: Artificial sequence
<220> FEATURE:
<223> OTHER INFORMATION: sense siRNA

<400> SEQUENCE: 95
ugaugcaugu gguccuucca acu 23

<210> SEQ ID NO 96
<211> LENGTH: 23
<212> TYPE: RNA
<213> ORGANISM: Artificial sequence
<220> FEATURE:
<223> OTHER INFORMATION: antisense siRNA

<400> SEQUENCE: 96
aguuggaagg accacaugca uca 23

<210> SEQ ID NO 97
<211> LENGTH: 23

<212> TYPE: RNA
<213> ORGANISM: Artificial sequence
<220> FEATURE:
<223> OTHER INFORMATION: sense siRNA

<400> SEQUENCE: 97
aauaaguuca acggcauuaa aug 23

<210> SEQ ID NO 98
<211> LENGTH: 23
<212> TYPE: RNA
<213> ORGANISM: Artificial sequence
<220> FEATURE:
<223> OTHER INFORMATION: antisense siRNA

<400> SEQUENCE: 98
cauuuaaugc cguugaacuu auu 23

<210> SEQ ID NO 99
<211> LENGTH: 23
<212> TYPE: RNA
<213> ORGANISM: Artificial sequence
<220> FEATURE:
<223> OTHER INFORMATION: sense siRNA

<400> SEQUENCE: 99
aggcucaggc uauucgcuca agg 23

<210> SEQ ID NO 100
<211> LENGTH: 23
<212> TYPE: RNA
<213> ORGANISM: Artificial sequence
<220> FEATURE:
<223> OTHER INFORMATION: antisense siRNA

<400> SEQUENCE: 100
ccuugagcga auagccugag ccu 23

<210> SEQ ID NO 101
<211> LENGTH: 23
<212> TYPE: RNA
<213> ORGANISM: Artificial sequence
<220> FEATURE:
<223> OTHER INFORMATION: sense siRNA

<400> SEQUENCE: 101
aggccacaac caugaugauc cga 23

<210> SEQ ID NO 102
<211> LENGTH: 23
<212> TYPE: RNA
<213> ORGANISM: Artificial sequence
<220> FEATURE:
<223> OTHER INFORMATION: antisense siRNA

<400> SEQUENCE: 102
ucggaucauc augguugugg ccu 23

<210> SEQ ID NO 103
<211> LENGTH: 23
<212> TYPE: RNA
<213> ORGANISM: Artificial sequence
<220> FEATURE:
<223> OTHER INFORMATION: sense siRNA

<400> SEQUENCE: 103

```
ccgaccagca gauuucuaaa cau                                               23


<210> SEQ ID NO 104
<211> LENGTH: 23
<212> TYPE: RNA
<213> ORGANISM: Artificial sequence
<220> FEATURE:
<223> OTHER INFORMATION: antisense siRNA

<400> SEQUENCE: 104

auguuuagaa aucugcuggu cgg                                               23


<210> SEQ ID NO 105
<211> LENGTH: 23
<212> TYPE: RNA
<213> ORGANISM: Artificial Sequence
<220> FEATURE:
<223> OTHER INFORMATION: antisense strand of Ang2_Bhandari_A3

<400> SEQUENCE: 105

auuuacugcu gaacucccac gga                                               23


<210> SEQ ID NO 106
<211> LENGTH: 23
<212> TYPE: RNA
<213> ORGANISM: Artificial Sequence
<220> FEATURE:
<223> OTHER INFORMATION: sense strand of Ang2_Bhandari_B3

<400> SEQUENCE: 106

uccgugggag uucagcagua aau                                               23


<210> SEQ ID NO 107
<211> LENGTH: 21
<212> TYPE: DNA
<213> ORGANISM: Artificial Sequence
<220> FEATURE:
<223> OTHER INFORMATION: antisense strand of Ang2_Bhandari_A

<400> SEQUENCE: 107

auuuacugcu gaacucccat t                                                 21


<210> SEQ ID NO 108
<211> LENGTH: 21
<212> TYPE: DNA
<213> ORGANISM: Artificial Sequence
<220> FEATURE:
<223> OTHER INFORMATION: sense strand of Ang2_Bhandari_B

<400> SEQUENCE: 108

ugggaguuca gcaguaaaut t                                                 21


<210> SEQ ID NO 109
<211> LENGTH: 23
<212> TYPE: RNA
<213> ORGANISM: Artificial Sequence
<220> FEATURE:
<223> OTHER INFORMATION: antisense strand of Ang2_Bhandari_Atu23_A

<400> SEQUENCE: 109

aguuauuuac ugcugaacuc cca                                               23


<210> SEQ ID NO 110
<211> LENGTH: 23
<212> TYPE: RNA
<213> ORGANISM: Artificial Sequence
```

-continued

```
<220> FEATURE:
<223> OTHER INFORMATION: sense strand of Ang2_Bhandari_Atu23_B

<400> SEQUENCE: 110

ugggaguuca gcaguaaaua acu                                          23
```